(12) United States Patent
Giacobini et al.

(10) Patent No.: US 12,208,130 B2
(45) Date of Patent: Jan. 28, 2025

(54) TREATMENT OF WOMEN AFFECTED WITH POLYCYSTIC OVARY SYNDROME

(71) Applicants: INSTITUT NATIONAL DE LA SANTE ET DE LA RECHERCHE MEDICALE (INSERM), Paris (FR); UNIVERSITÉ DE LILLE, Lille (FR); CENTRE HOSPITALIER REGIONAL UNIVERSITAIRE DE LILLE, Lille (FR)

(72) Inventors: Paolo Giacobini, Lille (FR); Vincent Prevot, Lille (FR)

(73) Assignees: INSTITUT NATIONAL DE LA SANTE ET DE LA RECHERCHE MEDICALE (INSERM), Paris (FR); UNIVERSITÉ DE LILLE, Lille (FR); CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 855 days.

(21) Appl. No.: 16/490,228

(22) PCT Filed: Mar. 14, 2018

(86) PCT No.: PCT/EP2018/056330
§ 371 (c)(1),
(2) Date: Aug. 30, 2019

(87) PCT Pub. No.: WO2018/177746
PCT Pub. Date: Oct. 4, 2018

(65) Prior Publication Data
US 2022/0257695 A1      Aug. 18, 2022

(30) Foreign Application Priority Data

Mar. 31, 2017  (EP) .................................... 17305385
Jul. 21, 2017  (EP) .................................... 17305971

(51) Int. Cl.
*A61K 38/09*    (2006.01)
*A61K 31/7105*  (2006.01)
*A61K 45/06*    (2006.01)

(52) U.S. Cl.
CPC .......... *A61K 38/09* (2013.01); *A61K 31/7105* (2013.01); *A61K 45/06* (2013.01)

(58) Field of Classification Search
CPC ..... A61K 38/09; A61K 31/7105; A61K 45/06
See application file for complete search history.

(56) References Cited

U.S. PATENT DOCUMENTS

2008/0194666 A1*  8/2008  Jabbour ................. A61K 31/40
                                                        514/408
2009/0197813 A1*  8/2009  Garnick ................. A61P 15/08
                                                        514/9.9

OTHER PUBLICATIONS

Ludwig et al (Arch.Gynecol.Obstet., 2001, 265, 175-182) (Year: 2001).*
Reissmann et al (Human Reproduction Update, 2000, vol. 6, No. 4, 322-331) (Year: 2000).*
Cardone et al [Fertility and Sterility, 2003, vol. 80, Suppl. 1, Jul. 2003, S25-S31] (Year: 2003).*
Coccia et al [European Journal of Obstetrics & Gynecology and Reproductive Biology, 2004, 1155, S44-S56] (Year: 2004).*
Coccia et al [European Journal of Obstetrics & Gynecology and Reproductive Biology, 2004, 115S, S44-S56] (Year: 2004).*
Finas et al [Expert Opin. Pharmacother., 2006, 7, 15, 2155-2168] (Year: 2006).*
Bruno et al [Ther Deliv, Nov. 2013, 4(11), 1443-1467] (Year: 2013).*
Kolibianakis E et al: "Reproductive outcome of polycystic ovarian syndrome patients treated with GnRH antagonists and recombinant FSH for IVF/ICSI", Reproductive Biomedicine Online, Elsevier, Amsterdam, NL, vol. 7, No. 3, Jan. 1, 2003, pp. 313-318.
X. Yan et al: "Prenatal androgen excess enhances stimulation of the GNRH pulse in pubertal female rats", Journal of Endocrinology, vol. 222, No. 1, Jun. 11, 2014, pp. 73-85.
S. D. Sullivan et al: "Prenatal androgens alter GABAergic drive to gonadotropin-releasing hormone neurons: Implications for a common fertility disorder", Proceedings National Academy of Sciences PNAS, vol. 101, No. 18, May 4, 2004, pp. 7129-7134.
Nicols Crisosto et al: "Improvement of hyperandrogenism and hyperinsulinemia during pregnancy in women with polycystic ovary syndrome: possible effect in the ovarian follicular mass of their daughters", Fertility and Sterility, Elsevier Science Inc, New York, NY, USA, vol. 97, No. 1, Oct. 6, 2011, pp. 218-224.

(Continued)

*Primary Examiner* — Sudhakar Katakam
(74) *Attorney, Agent, or Firm* — WC&F IP

(57) ABSTRACT

The present invention relates to the field of therapeutic treatment of polycystic ovary syndrome (PCOS). Polycystic ovary syndrome, PCOS, is the most common female reproductive disorder against which no therapeutic solution is available, beyond changes in the lifestyle. The inventors have now shown by using in vivo preclinical models, that individuals affected with PCOS have an abnormal elevated production of GnRH and that this elevated production of GnRH was transmitted to their offspring that also develop PCOS. Further, by examining AMH levels in a cohort of pregnant PCOS and control women, the inventors have found that AMH concentrations are significantly higher in PCOS women as compared to healthy women during the second trimester of gestation. These unexpected findings has allowed conceiving both prevention and treatment therapeutic strategies based on the administration of GnRH antagonists. Especially, the present invention relates to a gonadotropin-releasing hormone (GnRH) antagonist for its use in a woman affected with polycystic ovary syndrome (PCOS) for preventing the occurrence of PCOS in the offspring of the said woman. Even more interestingly, the present invention relates to a gonadotropin-releasing hormone (GnRH) antagonist for its use to rescue ovulation and fertility in postpuberal PCOS affected individuals.

5 Claims, 44 Drawing Sheets

Specification includes a Sequence Listing.

(56) References Cited

OTHER PUBLICATIONS

Andrea Messina et al: "A microRNA switch regulates the rise in hypothalamic GnRH production before puberty", Nature Neuroscience, vol. 19, No. 6, Jan. 1, 2016, pp. 835-844.
Tata, B. et al., "Elevated prenatal anti-Müllerian hormone reprograms the fetus and induces polycystic ovary syndrome in adulthood", Nature Medicine 24:6, 2018.

* cited by examiner

Pregnant mothers (E19.5)

Placenta E19.5

Dams (E19.5)

Dams (E19.5)

Placenta E19.5

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
cacctgcacg ttgccctt                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic primer

<400> SEQUENCE: 2
tggatggtgt ggccaatg                                                 18
```

TREATMENT OF WOMEN AFFECTED WITH POLYCYSTIC OVARY SYNDROME

FIELD OF THE INVENTION

The present invention relates to the field of therapeutic treatment of polycystic ovary syndrome (PCOS). Notably, this invention relates to the prevention of the occurrence of PCOS in the offspring of pregnant women affected with PCOS.

BACKGROUND OF THE INVENTION

Polycystic ovary syndrome, PCOS, is the most common female reproductive disorder, affecting up to 10% of women worldwide (Ehrmann, 2005, The New England journal of medicine, Vol. 352: 1223-1236; Norman et al., 2007, Lancet, Vol. 370: 685-697; Goodarzi et al., 2011, Nature reviews. Endocrinology Vol. 7: 219-231; Jayasena et al., 2014, Nature reviews. Endocrinology, Vol. 10: 624-636).

The cardinal abnormalities in PCOS women are excessive ovarian androgen secretion and disrupted reproductive cycles. Most women who are diagnosed with PCOS also exhibit accelerated LH secretion, which is suggestive of rapid gonadotropin-releasing hormone (GnRH) release (Ehrmann, 2005, The New England journal of medicine, Vol. 352: 1223-1236; Goodarzi et al., 2011, Nature reviews. Endocrinology Vol. 7: 219-231) and increased circulating levels of Anti-Mullerian Hormone (AMH) (Cook et al., 2002, Fertility and sterility, Vol. 77 141-146); Pigny et al., 2006, The Journal of clinical endocrinology and metabolism, Vol. 91: 941-945 (2006).

While the exact origin of PCOS is unknown, data from clinical and animal studies suggest that it may originate in utero and that environmental influences, such as hormonal imbalances during fetal life, could be important etiological factors in PCOS (Roland et al., 2014, Frontiers in neuroendocrinology; Puttabyatappa et al., 2015, Molecular and cellular endocrinology).

Treatment of PCOS can be costly to the health care system. Key non-infertility treatments include: oral contraceptives (for hormonal normalization), endometrial ablation (for anovulatory bleeding), insulin sensitizing agents, antihypertensive agents, statins, and treatments for severe acne and hirsutism.

Many women with PCOS may also require infertility treatment during their lifetime. Treatment for PCOS infertility typically follows a step-wise approach. For example, clomiphene citrate is generally the first-line treatment with second-line treatment being either gonadotropin administration or ovarian drilling (also sometimes referred to as ovarian diathermy). If these treatments are unsuccessful, in vitro fertilization (IVF) is attempted. In infertility treatment, multiple pregnancies and live births is often considered an undesirable result due to the associated perinatal and neonatal morbidity and the associated elevated costs. Furthermore, ovarian hyperstimulation syndrome (OHSS) may be more common in women with PCOS undergoing gonadotropin or IVF treatment. While OHSS is often mild and easily treated, more severe cases may require aggressive treatment. Methods of ovarian stimulation of PCOS women for the purpose of a subsequent in vitro fertilization, which methods include a step of blocking the production of LH, are disclosed in the art. Such methods are notably illustrated by the US patent application n° US 2009/0197813, which discloses such a method including a step of blocking LH by administration of a GnRH antagonist.

Familial clustering and twin studies have shown that PCOS has a strong heritable component (McAllister et al., Trends in endocrinology and metabolism: TEM Vol.: 26, 118-124). Nevertheless, the mutations that have been identified so far do not account for the frequency of all cases, implying that environmental factors, such as prenatal androgen excess, might also play important roles in the onset of this disease (Sir-Petermann et al. 2007, The Journal of clinical endocrinology and metabolism, Vol. 92: 4637-4642). Indeed, women with PCOS are likely to be hyperandrogenic during pregnancy (Sir-Petermann et al. 2007, The Journal of clinical endocrinology and metabolism, Vol. 92: 4637-4642; Sir-Petermann et al., Human reproduction, Vol. 17: 2573-2579) and endocrine alterations during gestation may contribute to increased risk for their female offspring to also develop PCOS. Although the mechanism of the elevation of androgens in PCOS remains enigmatic, increased ovarian androgen production is at the heart of one of the major issues in studying the pathophysiology of PCOS, i.e., whether this increase has developmental origins (Catteau-Jonard et al., Frontiers of hormone research, Vol. 40: 22-27 (2013) and whether it can be induced by environmental determinants. The prenatal androgen administration late in gestation (PNA) has been used to generate animal models in species ranging from rodents to ungulates to primates that bear many phenotypic similarities with PCOS (Roland et al., 2014, Frontiers in neuroendocrinology).

There is thus a need for designing efficient therapeutic strategies for preventing and treating PCOS.

SUMMARY OF THE INVENTION

This invention relates to a gonadotropin-releasing hormone (GnRH) antagonist for its use in a pregnant woman affected with polycystic ovary syndrome (PCOS) for preventing the occurrence of PCOS in the offspring of the said pregnant woman This invention also pertains to a therapeutic strategy to induce ovulation and restore menstrual cyclicity in adult PCOS affected individuals.

In some embodiments, the said GnRH antagonist is the sole active ingredient.

In some embodiments, the said GnRH antagonist is selected in a group comprising degarelix, ganirelix, cetrorelix and abarelix.

In some other embodiments, the said GnRH antagonist is selected in a group of micro-RNAs comprising miR155 and miR200.

This invention also concerns a gonadotropin-releasing hormone (GnRH) antagonist for its use for preventing or treating polycystic ovary syndrome PCOS in a female individual.

It notably relates to a gonadotropin-releasing hormone (GnRH) antagonist for its use for preventing polycystic ovary syndrome PCOS in a pre-puberal female individual.

It also pertains to a gonadotropin-releasing hormone (GnRH) antagonist for its use for treating polycystic ovary syndrome PCOS in a post-puberal female individual.

In some embodiments, the said GnRH antagonist is the sole active ingredient.

In some embodiments, wherein the said GnRH antagonist is comprised in a pharmaceutical composition adapted to its administration to a pre-puberal female individual.

In some embodiments, the said GnRH antagonist is comprised in a pharmaceutical composition adapted to its administration to a post-puberal female individual.

DESCRIPTION OF THE FIGURES

(FIG. 1A) Scatter-plot showing the circulating AMH levels in control pregnant women and in PCOS pregnant patients. (FIG. 1B) Scatter-plot showing the circulating AMH levels in control pregnant women and in PCOS pregnant patients stratified by the body mass index (BMI) of the patients and classified it into lean and obese subjects. (FIG. 1C) Scatter-plot showing the circulating AMH levels in PCOS pregnant patients stratified by their BMI and androgen levels (normoandrogenic or with signs of biochemical and/or clinical hyperandrogenism). (FIG. 1D) Scatter-plot showing the circulating AMH levels in control pregnant women and in PCOS pregnant patients stratified by their age. The horizontal line in each plot corresponds to the median value. The vertical line represents the 25th-75th percentile range. Comparisons between groups, matched by BMI, androgen levels and age, were performed using Mann-Whitney U test. The significance level was set at $P<0.05$. $*P<0.05$, $P<0.005$, $*P<0.0005$.

FIGS. 2A-2E-3. Prenatal AMH treatment disrupts estrous cyclicity, ovarian morphology and fertility in adult offspring. (FIG. 2A) Schematic of experimental design whereby pregnant dams were subjected to different treatments by intraperitoneal (i.p.) injections during the late gestational period (embryonic days (E) 16.5-E18.5). Pregnant dams were treated with i.p. injections of four different treatments, which are designated as the following: Control, PBS, 0.01M, pH 7.4 (n=14); Prenatal anti-Müillerian hormone-treated (PAMH), PBS containing human recombinant AMH (n=19); Prenatal AMH+Cetrorelix (PAMH+GnRH antag), PBS containing both human recombinant AMH and cetrorelix acetate (n=10); Cetrorelix-treated (GnRH antag), PBS containing cetrorelix acetate (n=4). (FIG. 2B) Quantitative analysis of ovarian cyclicity in adult (P60-P90) offspring mice (control, n=14; PAMH, n=19; PAMH+GnRH antag, n=10; GnRH antag, n=4). Vaginal cytology was assessed for 16 days. PAMH animals spent significantly more days in the Metestrus/Diestrus phase (M/D) and less in Proestrus (P) and Estrus (E) as compared with the other treatment groups (Kruskal-Wallis test, $*P<0.0001$). Bars from left to right in each group: Control, PAMH, PAMH+GnRH antag, GnRH antag. (FIGS. 2C-1, 2C-2, 2C-3) Representation of estrous cyclicity in one female mouse of each of the four treatments during 16 consecutive days (4-cycles). (FIGS. 2D-1, 2D-2, 2D-3) Quantitative analysis of corpora lutea, late antral follicles and atretic follicles in the ovaries of Control (n=7, age: P90) and PAMH mice (n=8, age: P90). Data are represented as mean±s.e.m (two-tailed Student's t-test; corpora lutea, $t_{(13)}=4.879$, $P<0.001$; late antral follicles, $t_{(13)}=4.637$, $P<0.001$; atretic follicles, $t_{(13)}=0.226$, P=0.82). Data were combined from two independent experiments. In FIGS. 2D-1, 2D-2 and 2D-3: left bar: Control; right bar: PAMH.). (FIGS. 2E-1, 2E-2, 2E-3) Fertility tests of the adult offspring mice (P90). Bars from left to right in each FIGS. 2E-1, 2E-2 and 2E-3: Control, PAMH, PAMH+ GnRH antag, GnRH antag Matings were performed for 90 days. Control females were paired with control males (n=7), PAMH females were paired with PAMH males (n=7), PAMH+GnRH antag females were paired with PAMH+ GnRH antag males (n=6), and GnRH antag females were paired with GnRH antag males (n=4). Female PAMH mice exhibit impaired fertility. Data are represented as mean±s.e.m. One-way ANOVA and Tukey's multiple comparison post hoc test: time to first litter, $F_{(3,20)}=14.73$, $*P<0.0001$; fertility index, $F_{(3,20)}=7.069$, $*P<0.05$, $P<0.005$; number of pups/litter, $F_{(3,20)}=30.71$, $*P<0.0001$.

FIGS. 3A-3J-4. Prenatal AMH treatment leads to hyperandrogenism and elevation in LH secretion/pulsatility. (FIG. 3A) Anogenital distance (AGD) was measured over post-natal days (P) 30, 35, 40, 50, and 60 in adult female control (n=6-14), PAMH (n=11-19), PAMH+GnRH antag (n=10), and GnRH antag (n=4) mice. AGD was significantly longer in PAMH females as compared to other groups throughout post-natal development. One-way ANOVA and Tukey's multiple comparison post hoc test, $F_{(19-183)}=130.1$, $***P<0.0001$ among treatment groups and ages (P30, $F_{(3, 43)}=84.48$, $*P<0.05$, $***P<0.0001$; P35, $F_{(3, 43)}=116.9$, $*P<0.05$, $***P<0.0001$; P40, $F_{(3, 43)}=207.5$, $*P<0.05$, $*P<0.0001$; P50, $F_{(3,27)}=72.69$, $*P<0.0001$; P60, $F_{(3,27)}=110.5$, $*P<0.0001$). Bars from left to right in each group: Control, PAMH, PAMH+GnRH antag, GnRH antag. (FIG. 3B) Plasma testosterone was measured in adult females (P60) in diestrus. PAMH mice (n=5) have higher testosterone levels as compared to control (n=5) and PAMH+GnRH antag (n=5) littermates. One-way ANOVA and Tukey's multiple comparison post hoc test, $F_{(2,12)}=28.67$, $*P<0.0001$. Bars from left to right: Control, PAMH, PAMH+GnRH antag. (FIG. 3C) Plasma LH was measured in adult females (P60) in diestrus. Mean circulating LH levels were significantly higher in adult (P60) PAMH (n=10) females as compared to control (n=8) and PAMH+GnRH antag (n=9) female littermates. One-way ANOVA and Tukey's multiple comparison post hoc test, $F_{(2,24)}=257.3$, $*P<0.05$, $***P<0.0001$. Bars from left to right: Control, PAMH, PAMH+GnRH antag. (FIG. 3D) Schematic representation of tail-tip blood sampling in adult diestrus female mice (3-4 months old). (FIG. 3E) Tail blood was collected every 10 min for 2 h and LH measured from 10 a.m-12 p.m in adult (P60) diestrus females (Control, n=8; PAMH, n=10; PAMH+GnRH antag, n=9; One-way ANOVA and Tukey's multiple comparison post hoc test, $F_{(2,24)}=57.06$, $*P<0.05$, $*P<0.0001$). Bars from left to right: Control, PAMH, PAMH+GnRH antag. (FIGS. 2F-1, 2F-2, 2F-3) Representative graphs for LH pulsatility over 2-hr in one female adult (P60) mouse of each treatment. Asterisks in (FIG. 3F) indicate the number of LH pulses/2-hr. (FIG. 3G) Mean circulating testosterone and LH levels were analyzed in pregnant PBS-treated (n=4) and AMH-treated (n=4) dams at embryonic day (E) 19.5 of gestation. Testosterone levels in pregnant-dams at E1 9.5 were significantly higher in AMH-treated animals as compared to control (Unpaired Student's t-test, $t_{(6)}=8.347$, $P<0.005$). AMH-treated pregnant dams also exhibited significantly higher LH levels at E19.5 compared to control-treated pregnant dams (Unpaired Student's t-test, $t_{(6)}=4.031$, $*P<0.05$). (FIG. 3H) Relative mRNA expression of placental Cyp191a (aromatase) in control (n=4) and AMH (n=4)-treated pregnant animals at E19.5. Cyp191a expression in the placenta is higher in AMH-treated pregnant dams as compared to control-treated pregnant dams (Unpaired Student's t-test, $t_{(6)}=5.414$, $**P<0.005$). Values are expressed as relative to the mean of each treatment. All values are expressed as mean±s.e.m. (FIGS. 3I-1, 3I-2, 3I-3, 3I-4) Dams were injected from E16.5 to E18.5 with either PBS (vehicle, n=9-11), AMH (n=8-10), AMH+GnRH antag (n=5) and trunk blood was collected at E19.5 for hormonal measurements by ELISA. Data were combined from at least two independent experiments. In FIGS. 3I-1, 3I-2, 3I-3, 3I-4: left bar: vehicle; middle bar: AMH; right bar: AMH+GnRH antagonist. (FIGS. 3J-1, 3J-2, 3J-3, 3J-4)) Real-time PCR analysis of expression levels of AMHR2, CYP191A (cytochrome P450 family 19A1, aromatase), CYP11A1 (cytochrome P450 family 11A1), HSD3B1 (3beta-hydroxysteroid dehydrogenase/delta(5)-delta(4)isomerase type I or hydroxy-delta-5-steroid dehydrogenase) mRNA in the placenta of E19.5 dams. Dams were injected i.p. from E16.5 to E18.5 with either PBS (vehicle, n=8-17), AMH (n=7-11), or AMH+ GnRH antag (n=8-13). Data were combined from three independent experiments. Throughout, data are displayed as mean±s.e.m. Statistics were computed with one-way ANOVA followed by Tukey's multiple comparison post hoc test. *P<0.05, P<0.001 and *P<0.0001; n.s: not significant. In FIGS. 3J-1, 3J-2, 3J-3, 3J-4: left bar: vehicle; middle bar: AMH; right bar: AMH+GnRH antagonist.

FIGS. 4A-4C-2. Prenatal AMH treatment increases perinatal T levels in females and masculinizes their brain. (FIG. 4A) Plasma T and LH levels were measured in pups 2 hours after birth (males, n=5; control females, n=5; PAMH females, n=4; PAMH females+GnRH antag, n=6). (FIG. 4B) TH immunoreactive (-ir) neurons in the AVPV were quantified in these animal groups (n=3 per sex and treatment). The number of AVPV TH-ir neurons are represented as the mean±s.e.m. (One-way ANOVA and Tukey's multiple comparisons post-hoc test, $F_{(2,6)}$=231.1, ***P<0.0001). In FIG. 4B: left bar: male; middle bar: control female; right bar: PAMH female. (FIGS. 4C-1, 4C-2)

The number of BNST and MeA VP-ir neurons are represented as the mean±s.e.m. (One-way ANOVA and Tukey's multiple comparisons post-hoc test: BNST, $F_{(2,6)}$=185.2; MeA, $F_{(2,6)}$=351.7,* P<0.05, P<0.005, *P<0.0001). In FIGS. 4C-1, 4C-2, left bar: male; middle bar: control female; right bar: PAMH female.

(FIG. 5A) The GnRH dendritic spine density was analyzed in adult (P60) diestrus control and PAMH GnRH:: GFP females. Two sections with the largest number of GnRH neurons (levels of the rPOA containing the OVLT) where chosen from each animal, where the full extent of GFP-labeled GnRH neurons (n=10-12 neurons/treatment) were imaged and analyzed using confocal microscopy. Spine density was quantified for the soma and each 15 μm portion of the primary GnRH neuronal dendrite. The number of spines on the GnRH soma was significantly higher in PAMH females compared to control (Unpaired Student's t-test, t (18)=7.5434, *P<0.0001, n=10 neurons/treatment), as well as along the primary GnRH dendrite (Unpaired Student's t-test, 15 μm, t (22)=9.08, *P<0.0001, n=12 neurons/treatment; 30 μm, t (22)=6.92, *P<0.0001, n=12 neurons/treatment; 45 μm, t (22)=5.252, *P<0.0001, n=12 neurons/treatment). In FIG. 5A, light gray: control; dark grey: PAMH. (FIG. 5B) Quantification of the number of vGaT-immunoreactive punctae adjacent to GnRH neuron soma and along the primary GnRH neuronal dendrite is expressed as vGaT appositions/μm. vGaT contacts were defined as positive when vGaT immunolabeling was directly apposed onto the GnRH neuronal dendrites without any black pixels between the GnRH dendritic spine. The number of vGaT appositions/μm was higher in PAMH females as compared with control females (n=10 neurons/animal and treatment) at both the levels of the GnRH soma (Unpaired Student's t-test, t test, $t_{(18)}$=16.4, *P<0.0001) and along the entire length of the GnRH dendrite (0-45 μm; Unpaired Student's t-test: 15 μm, $t_{(18)}$=7.341; *P<0.0001, 30 μm; t(18)=9.929, P<0.0001; 45 μm; t(18)=16.4, ***P<0.0001). (FIGS. 5C to 5G) Electrophysiological recordings were analyzed in diestrus adult (3-4 months) control (n=4) and PAMH (n=4) GnRH::GFP female diestrus mice. In FIG. 5B, light gray: control; dark grey: PAMH. (FIG. 5C) Whole-cell current-clamp recording showing the typical spontaneous burst firing of a GnRH neuron from control mouse. The bottom trace shows an expanded time scale of that recording. (FIG. 5D) Same experiment as in (FIG. 5C) but in a GnRH neuron from PAMH mouse. Note the increased firing frequency of spontaneous action potentials in this cell compared to that in the GnRH neuron from control mouse in (FIG. 5C). (FIG. 5E) Average firing rate of GnRH neurons recorded from control (n=9 cells from 4 animals) and PAMH mice (n=8 cells from 4 animals) was higher in PAMH females as compared to control (Unpaired Student's t-test, t (15)=2.982, *P<0.005). (FIG. 5F) Average resting membrane potential (RMP) of GnRH neurons recorded from control (n=10 cells from 4 animals) and PAMH mice (n=8 cells from 4 animals) was not significant between PAMH and control (Unpaired Student's t-test, t (16)=1.143, P=0.2700, ns). (FIG. 5G) Average input resistance (Rin) of GnRH neurons recorded from control (n=6 cells from 4 animals) and PAMH mice (n=7 cells from 4 animals) was not found significant between PAMH and control (Unpaired Student's t-test, t (11)=0.3685, P=0.7195, ns, not significant).

Figure 1A:
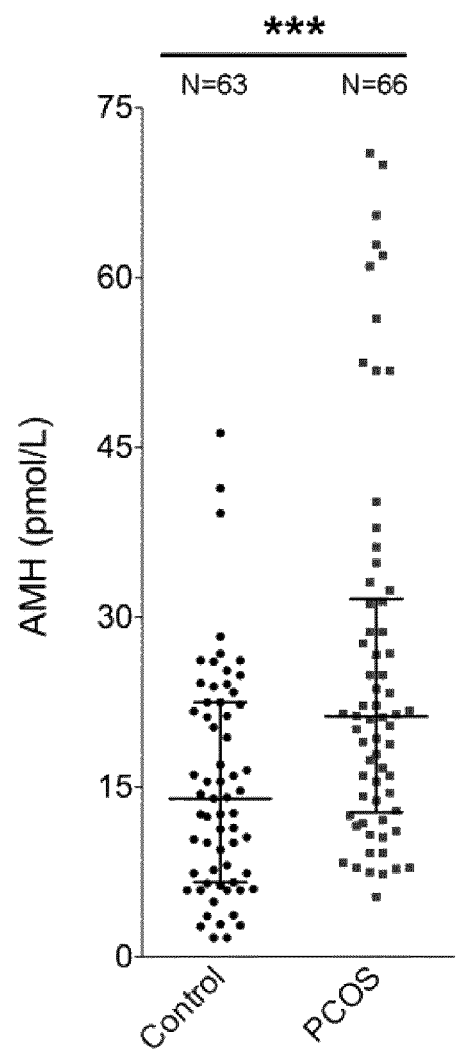
FIGS. 1A-1D. AMH levels during the second trimester of gestation are higher in PCOS women than control women. Blood samples were derived from 63 control and 66 PCOS pregnant women at gestational week 16-19 and AMH concentration was measured by ELISA.

All values are represented as mean±s.e.m. OVLT, organum vasculosum lamina terminalis; rPOA, rostral Pre-Optic Area.

FIG. 6A-6G. Postnatal GnRH antagonist treatment of PAMH mice restores the PCOS-like neuroendocrine phenotype. (FIG. 6A) Schematic of experimental design whereby vaginal cytology (estrous cyclicity) in PAMH adult (P60-P90, n=5) was analyzed for 12 days before and after postnatal intraperitoneal (i.p.) injections with 0.5 mg $Kg^{-1}$ cetrorelix acetate (PAMH+GnRH antag). Injections were administered every 2 days over 12 days and, on the first diestrus at the end of the treatment, trunk blood was collected for hormonal analysis. (FIG. 6B) Representation of estrous cyclicity of a female PAMH mouse before postnatal GnRH antagonist treatment (no treatment) and during postnatal GnRH antagonist treatment (PAMH+GnRH antag). Days of treatment are denoted by arrows. (FIG. 6C) Quantitative analysis of the % of completed estrous cycles in control (prenatal PBS-treated, n=19), PAMH (prenatal AMH-treated, n=19), and PAMH mice postnatally treated with GnRH antagonist (PAMH+GnRH antag, n=5). The horizontal line in each scatter plot corresponds to the median value. The vertical line represents the 25th-75th percentile range. Comparisons between treatment groups were performed using Kruskal-Wallis test followed by Dunn's post hoc analysis test (control vs PAMH ***P<0.0001; control vs PAMH+GnRH antag, P>0.999; PAMH vs PAMH+GnRH antag, *P=0.015). (FIG. 6D) Scatter plot representing the percentage (%) of time spent in each estrous cycle. The horizontal line in each scatter plot corresponds to the median value. The vertical line represents the $25^{th}$-$75^{th}$ percentile range. The percentage (%) of time spent in each estrous cycle was quantified in control, PAMH and PAMH+GnRH antag animals groups, as described above. Comparisons between treatment groups were performed using Kruskal-Wallis test followed by Dunn's post hoc analysis test (M/D: control vs PAMH ***P<0.0001; control vs PAMH+GnRH antag, P>0.999; PAMH vs PAMH+GnRH antag, *P=0.0051; E: control vs PAMH ***P<0.0001; control vs PAMH+

GnRH antag, P>0.999; PAMH vs PAMH+GnRH antag, *P=0.014; P: control vs PAMH *P<0.0001; control vs PAMH+GnRH antag, P>0.999; PAMH vs PAMH+GnRH antag, P=0.0007). In FIG. 6D, (●): control; light grey point: PAMH; "○": PAMH+GnRH antagonist. (FIG. 6E) Representative photomicrographs of ovaries from adult (P60-P90) control, PAMH and PAMH+GnRH antag mice. Ovary sections (5 µm thick) were stained with haematoxylin-eosin. (FIG. 6F) Mean T levels were measured in diestrus adult control (n=7), PAMH (n=5) and PAMH+GnRH antag (n=5) animals. Comparisons between treatment groups were performed using One-way ANOVA and Tukey's multiple comparisons post-hoc test, F (2,14)=29.24, *P<0.0001. (FIG. 6G) Mean LH levels were measured in diestrus adult control (n=9), PAMH (n=10) and PAMH+GnRH antag (n=5) animals. Comparisons between treatment groups were performed using One-way ANOVA and Tukey's multiple comparisons post-hoc test, $F_{(2,21)}$=65.78, *P<0.0001. Abbreviations: M/D, Metestrus/Diestrus; E, Estrus; P, Proestrus; A, atretic follicles; CL, corpora lutea; AF, antral follcicles.

Figure 7A:
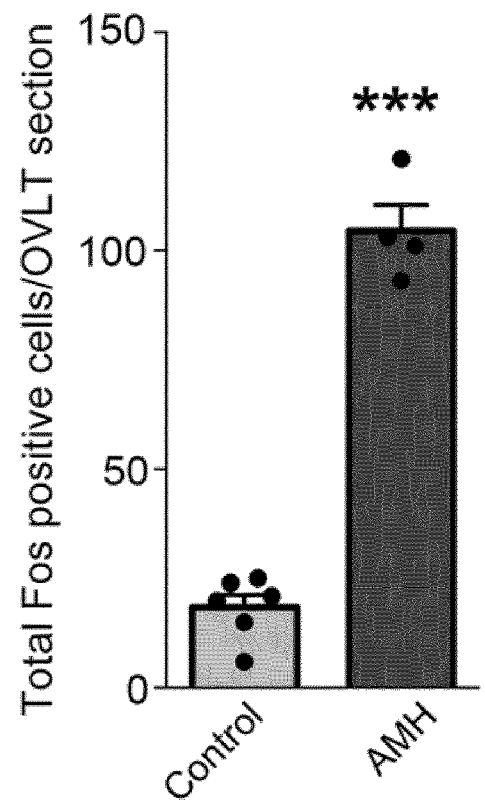
Figure 7B:
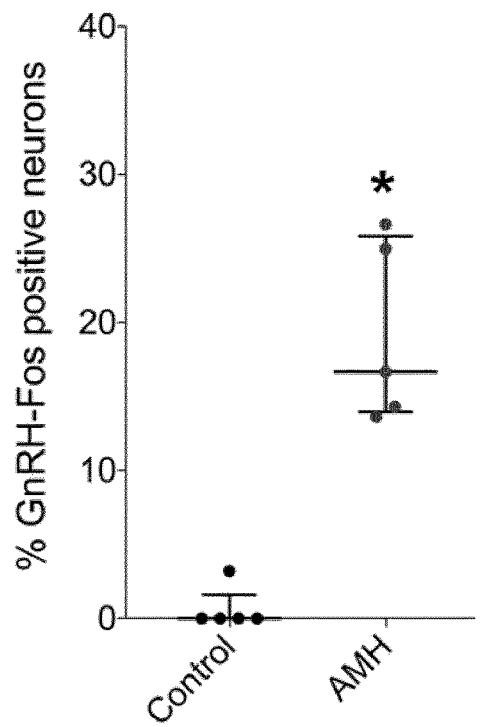

FIGS. 7A-7B. Peripheral AMH administration induces Fos expression in the OVLT area including GnRH neurons. Female adult mice (P60-90) were injected (i.p.) with PBS (control) or AMHc in diestrus and sacrificed 90 min later. (FIG. 7A) The total number of Fos positive cells was quantified in the OVLT sections of control (n=6) and AMH-treated animals (n=4). Control females exhibit less Fos immunoreactive cells/OVLT section as compared to AMH-treated mice (Unpaired Student's t-test $t_{(8)}$=14.57, *** P<0.0001). (FIG. 7B) Scatter plot representing the percentage (%) of GnRH neurons expressing Fos in the OVLT sections. The horizontal line in each scatter plot corresponds to the median value. The vertical line represents the $25^{th}$-$75^{th}$ percentile range. Comparisons between treatment groups (n=5 per animal group) were performed using Mann-Whitney U test, * P=0.007. OVLT, organum vasculosum laminae terminalis.

FIGS. 8A-8D. Prenatal AMH treatment disrupts puberty onset and estrous cyclicity cyclicity but not body mass of the offspring. (FIGS. 8A, 8B, 8C, 8D) Parameters of pubertal onset and estrous cyclicity in female control (n=14), PAMH (n=17-19), PAMH+GnRH antag (n=10), and GnRH antag (n=4) animals. (FIG. 8A) Age of vaginal opening (VO) and (FIG. 8B) Age of first estrus were compared using a one-way ANOVA and Tukey's multiple comparison post hoc analyses, respectively: F (3, 43)=48.37, * P<0.0001; F (3, 41)=112.6, * P<0.0001. Bars from left to right in each FIGS. 8A, 8B: Control, PAMH, PAMH+GnRH antag, GnRH antag (FIG. 8C) Percentage (%) of completed estrous cycles over 16 days (4 cycles) was analyzed using a nonparametric Kruskal-Wallis test followed by a Dunn's multiple comparison post-hoc analysis: Kruskal-Wallis statistic=35.55, *P<0.05, P<0.005, *P<0.0001. Bars from left to right in each FIG. 8C: Control, PAMH, PAMH+ GnRH antag, GnRH antag (FIG. 8D) Body mass (gr) was measured in female offspring at each post-natal age (P) until P60 and compared using a one-way ANOVA and Tukey's multiple comparison post hoc analyses for each age and treatment: P30, F (3, 43)=1.338, P=0.2747; P35, F (3, 43)=0.4268, P=0.7348; P40, F (3, 43)=0.4171, P=0.7416; P50, F (3, 27)=2.158, P=0.1162; P60, F (3, 27)=5.45, P=0.0046; * P<0.05, **, P<0.005. Asterisks represent significant differences (mean±s.e.m): *P<0.05, P<0.005, *, P<0.0001. Bars from left to right in FIG. 8D: Control, PAMH, PAMH+GnRH antag, GnRH antag.

FIGS. 9A-9F: Prenatal AMH treatment does not alter body weight of the dams and pups at birth but increases litter loss. Dams were injected from E16.5 to E18.5 with either PBS (vehicle, n=8-11), AMH (n=10), AMH+GnRH antag (n=8-10). Body weight (grams: g); (FIG. 9A), subcutaneous fat mass (FIG. 9B) and perigonadal fat mass (FIG. 9C) was measured in dams at gestational day 19.5. (FIG. 9D) Dams were injected from E16.5 to E18.5 with either PBS (vehicle, n=9), AMH (n=9), AMH+GnRH antag (n=9). Dams were sacrificed one day later and the number of aborted embryos per litter was calculated. (FIGS. 9E, 9F) Dams were injected from E16.5 to E18.5 with either PBS (vehicle, n=3), AMH (n=3), AMH+GnRH antag (n=3). The number of pups per litter (FIG. 9E) and the weight of the pups at birth (FIG. 9F) was calculated for each treatment group (vehicle, n=12 pups; AMH, n=11 pups; AMH+GnRH antag, n=12 pups). Values are represented as the mean±s.e.m. Statistics were computed with one-way ANOVA followed by Tukey's multiple comparison post hoc test. *P<0.05, **P<0.001; n.s.: not significant (P>0.05). Data were combined from three independent experiments. FIGS. 9A to 9F: left bar: vehicle; middle bar: AMH; right bar: AMH+GnRH antagonist.

FIGS. 10A-10H. Postnatal GnRH antagonist treatment of PAMH mice restores the PCOS-like neuroendocrine phenotype.

Figure 10A:
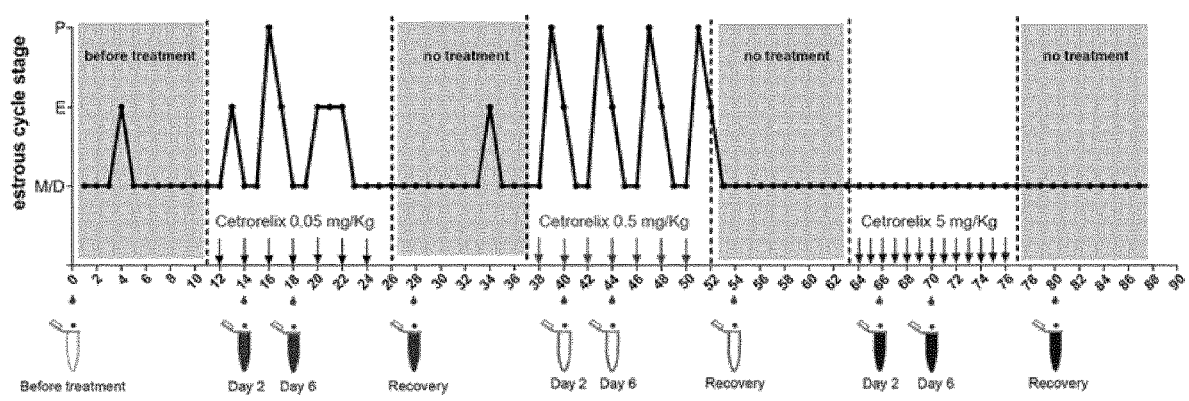
Figure 10B:
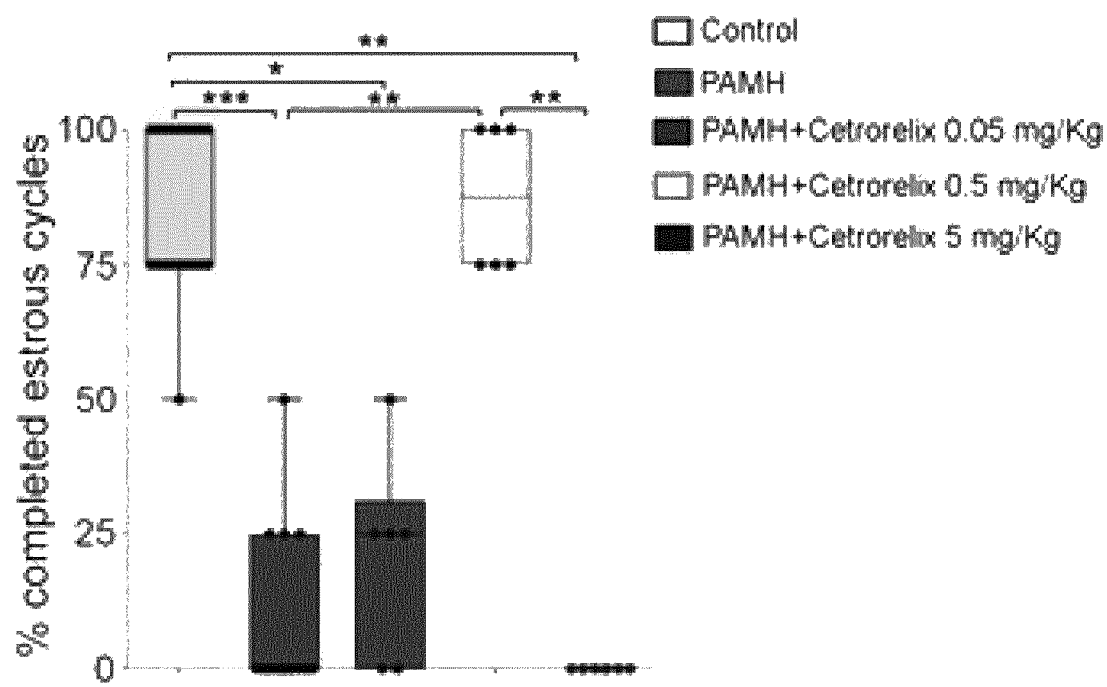
Figure 10C:
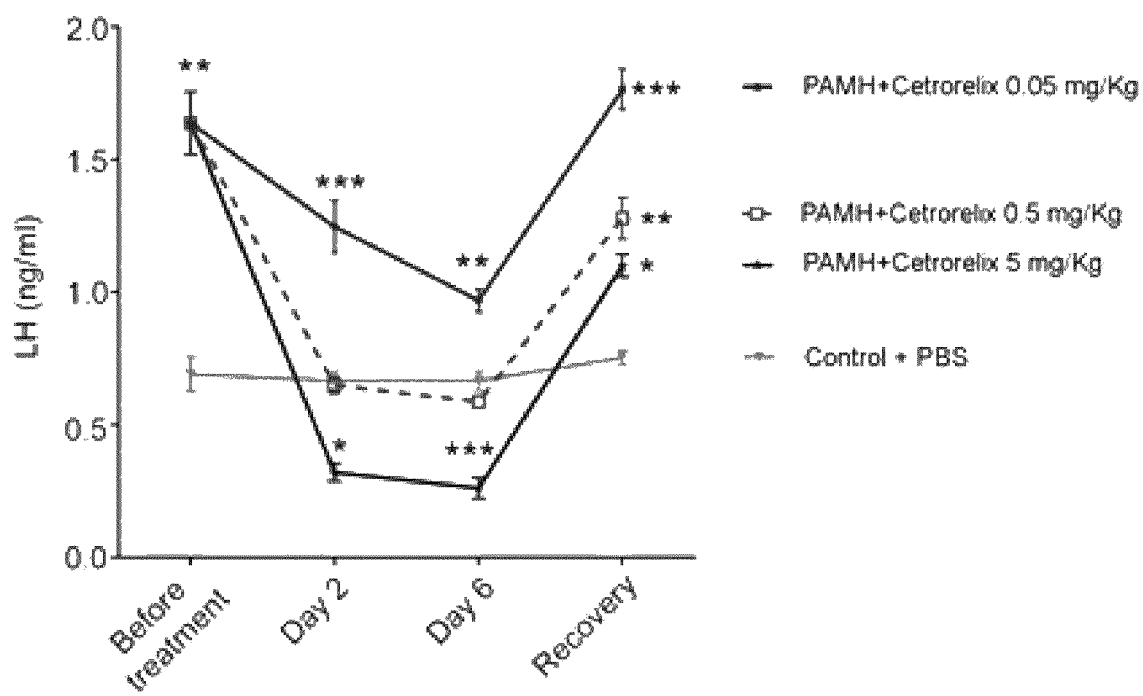

(FIG. 10A) Schematic of experimental design whereby vaginal cytology (estrous cyclicity) in PAMH adult mice (P90, n=6) was analyzed during 3 months, before and after postnatal intraperitoneal (i.p.) injections with 0.05, 0.5 and 5 mg/Kg Cetrorelix acetate. The Y axis refers to the different stages of the estrous cycle: Metaestrus/Diestrus (M/D), Estrus (E) and Proestrus (P). The X axis represents the time-course of the experiments (days). Animals were injected i.p. every second day, for 12 days, with Cetrorelix acetate at the dose of 0.05 and 0.5 mg/Kg, and every day with Cetrorelix acetate at the dose of 5 mg/Kg. Tail-blood samples were collected for LH measurements twice before the beginning of the treatments, and at day 2 and 6 of each treatment as well as 4 days after the last injection (no treatment), that followed each administration period. (FIG. 10B) Quantitative analysis of the % of completed estrous cycles in control (PBS-treated, n=19), PAMH (n=13), and PAMH mice postnatally treated with the three doses of GnRH antagonist (PAMH+Cetrorelix 0.05 mg/Kg, PAMH+ Cetrorelix 0.5 mg/Kg, PAMH+Cetrorelix 5 mg/Kg; n=6 each). The horizontal line in each scatter plot corresponds to the median value. The vertical line represents the $25^{th}$-$75^{th}$ percentile range. Comparisons between treatment groups were performed using nonparametric Kruskal-Wallis test followed by Dunn's post hoc analysis test. In FIG. 10B, bars from left to right: control; PAMH, PAMH+Cetrorelix 0.05 mg/Kg; PAMH+Cetrorelix 0.5 mg/Kg; PAMH+Cetrorelix 5 mg/Kg. (FIG. 10C) Time course of serum LH measured on days 0 (before treatment), 2 and 6 of the treatment and 4 days after discontinuation of the treatment (recovery time). Treatment groups (n=6 for each Cetrorelix treatment group and n=3 for the Control) are indicated in the figure. Data were combined from two independent experiments. (FIG. 10D) Mean LH levels were measured in diestrus adult (P60-P120) control mice (n=9), PAMH (n=16), PAMH+ Cetrorelix 0.05 mg/Kg (n=6), PAMH+Cetrorelix 0.5 mg/Kg (n=11), PAMH+Cetrorelix 5 mg/Kg (n=6). Data were combined from three independent experiments. (FIG. 10E) Scatter plot representing the percentage (%) of time spent in each estrous cycle. The horizontal line in each scatter plot corresponds to the median value. The vertical line represents the $25^{th}$-$75^{t}$h percentile range. The percentage (%) of time spent in each estrous cycle was quantified in control (n=19), PAMH (n=11) and PAMH+Cetrorelix 0.5 mg/Kg (n=11) mice (age: P60-P90), as described above. Comparisons between treatment groups were performed using Kruskal-Wallis test followed by Dunn's post hoc analysis test. Data were combined from three independent experiments. In FIG. 10E, from left to right of each group: control; PAMH; PAMH+Cetrorelix 0.5 mg/Kg (FIG. 10F) Mean T levels were measured by ELISA in diestrus adult control (n=7), PAMH (n=5) and PAMH+Cetrorelix 0.5 mg/Kg (n=5) animals. (FIG. 10G) Tail blood was collected every 10 min for 2 h and LH level measured from 10 a.m-12 p.m in adult (P90) diestrus females (Control, n=6; PAMH, n=6; PAMH+Cetrorelix 0.5 mg/Kg, n=6). (FIG. 10H) Representative graphs for LH pulsatility over 2-hr in one female adult (P90) mouse of each treatment. Asterisks in (FIG. 10H) indicate the number of LH pulses/2-hr. The dotted line refers to the control LH baseline value. Values in c, d, f, g are represented as the mean±s.e.m. Statistics in FIGS. 10C, 10D, 10F and 10G were computed with one-way ANOVA followed by Tukey's multiple comparison post hoc test. *$P<0.05$, $P<0.001$ and *$P<0.0001$. Experiments were replicated three times with similar results.

Figure 11A:
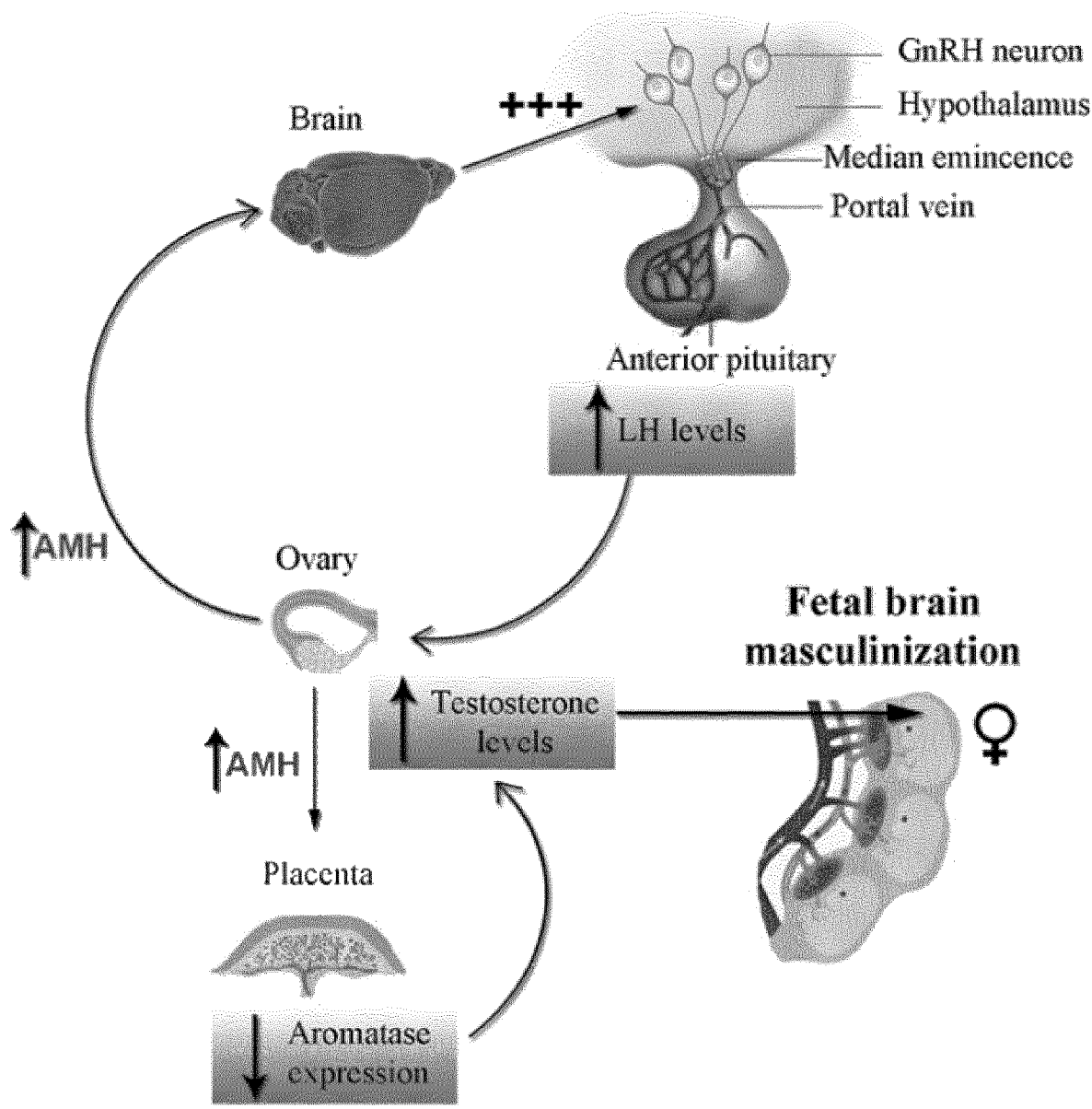
Figure 11B:
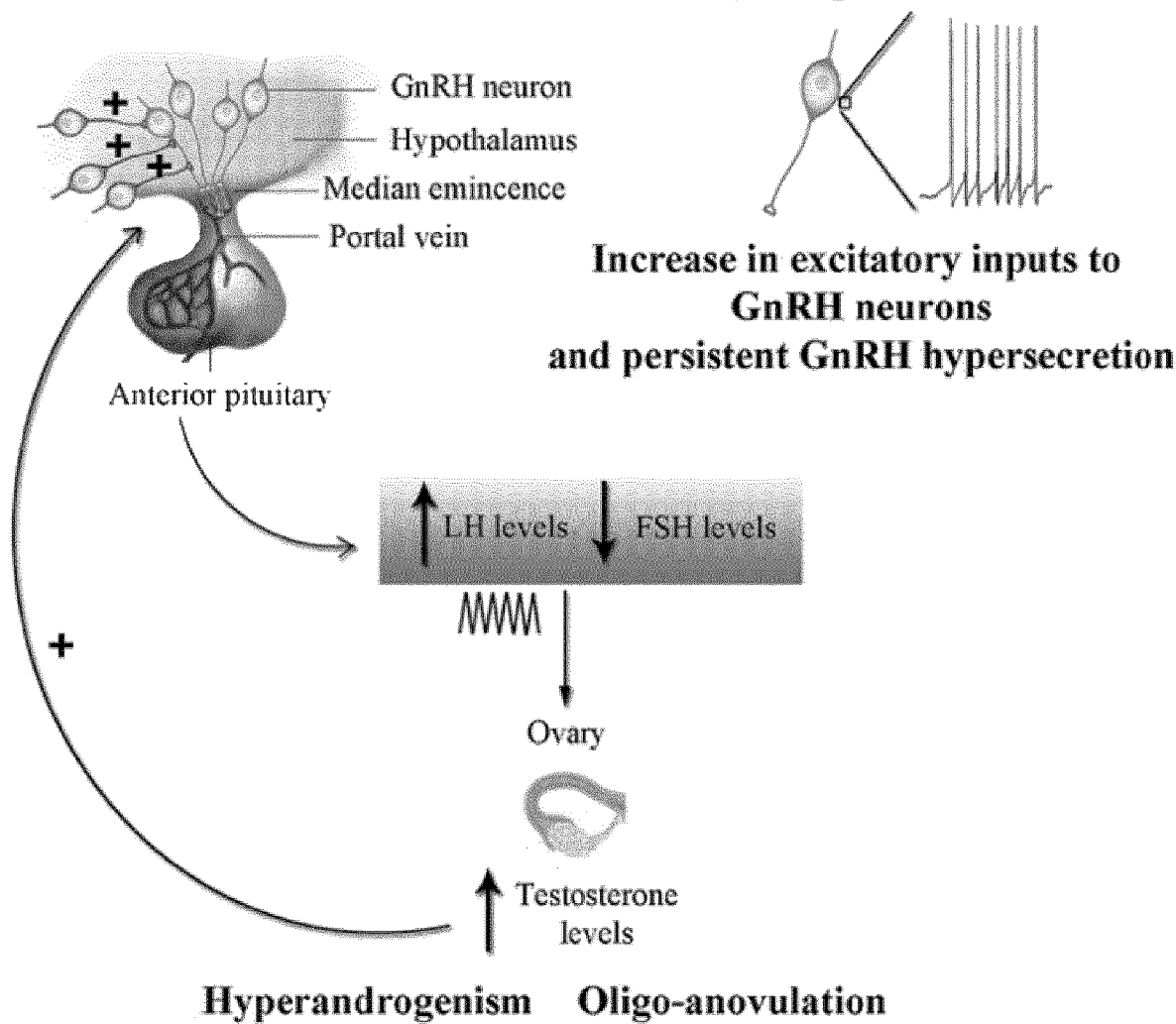

FIGS. 11A-11B. Schematic representation of the proposed mechanism of action of AMH in the prenatal programming of PCOS. Prenatal exposure to elevated AMH levels (FIG. 11A) leads to increased GnRH/LH pulsatility in pregnant mice, which drives steroidogenesis and hyperandrogenism. The maternal androgenization is further exacerbated by inhibition of aromatase expression in the placenta leading to an increase in testosterone bioavailability. The elevated levels of T trigger a cascade of events in the offspring, which converge into the masculinization of the brain sexually dimorphic nuclei and altered hypothalamic wiring. In adult female PCOS offspring (FIG. 11B), the increase in excitatory synaptic input to GnRH drives a persistent rise in the GnRH neuronal firing activity. Finally, the constitutive hyperactivity of GnRH neurons stimulates ovarian androgen production and impairs folliculogenesis and ovulation, contributing to the vicious circle of PCOS.

DETAILED DESCRIPTION OF THE INVENTION

The present inventors have unexpectedly found that preclinical models of polycystic ovary syndrome (PCOS) have an abnormal elevated production of GnRH. The inventors have also shown that the elevated production of GnRH affecting those PCOS preclinical models is transmitted to their offspring that also develop PCOS pathology. Moreover, the GnRH neurons of the PCOS preclinical models are hyperactive throughout the course of their life, implying that normalization of the GnRH neuronal activity by an antagonist could restore GnRH function, LH secretion, T levels and ovulation.

Further, by examining AMH levels in a cohort of pregnant PCOS and control women, the inventors have found that AMH concentrations are significantly higher in PCOS women as compared to healthy women during the second trimester of gestation.

The present inventors have also found that exposure to excess AMH during pregnancy imbalances the hypothalamic-pituitary-gonadal axis in both the mothers and their progeny. Female offspring recapitulated the major PCOS neuroendocrine reproductive features, namely elevation in testosterone and LH levels, associated with oligo-anovulation and impaired fertility. Moreover, prenatal AMH-treated (PAMH) female offspring exhibited an increase in the excitatory inputs onto GnRH neurons and heightened GnRH neuronal activity in adulthood.

It is further shown herein that prenatal GnRH antagonist treatment prevents the transgenerational transmission of the disease. Additionally, postnatal GnRH antagonist treatment restored the neuroendocrine phenotype of PCOS-like animals. Notably, the experimental results described in the present disclosure showed that the prenatal co-treatment of AMH with the GnRH antagonist prevented the appearance of PCOS-like neuroendocrine traits in the offspring, showing a critical role for GnRH in the prenatal programming of the disease. As it is shown in the experimental results disclosed herein, a peripheral injection of a GnRH antagonist allows the said GnRH antagonist accessing the maternal as well as the fetal brain. The experimental results herein show that the effect of the prenatal antagonist treatment on the prevention of PCOS-like traits acquisition in the offspring is most likely happening through the normalization of the maternal HPG axis.

The inventors' findings highlight the importance of elevated AMH in the prenatal programming of PCOS, show a critical role for GnRH in the neuroendocrine dysfunctions of PCOS and point to the GnRH antagonist treatment as a potential therapeutic strategy to treat this disease.

Even more strikingly, the inventors have shown that postnatal GnRH antagonist treatment of adult PAMH mice, at a concentration that only partially compete with endogenous GnRH for binding to membrane receptors on gonadotropes, restores their ovulation and normalizes androgen levels as well as LH secretion/pulsatility.

Based on these totally unexpected findings, the inventors have conceived both a prevention therapy and a treatment therapy against PCOS based on a blockade of the elevated production of GnRH, through the use of GnRH antagonists.

Given the fact that GnRH antagonists are frequently used in the clinic, with no adverse secondary effects, pharmacological antagonism aimed at tempering GnRH/LH secretion is an attractive therapeutic strategy to restore ovulation and fertility in PCOS individuals characterized by normal body mass composition and high LH levels.

Further, the inventors have tested the relevancy of the administration of a GnRH antagonist to pregnant female individuals with the view of preventing the occurrence of PCOS in their offspring. As it is shown in the examples herein, such a GnRH antagonist therapy given to a pregnant female individual has proved its efficiency for preventing the occurrence of PCOS to her offspring, i.e. her female offspring.

The present inventors have also unexpectedly found that administering a GnRH antagonist to human female individuals affected with polycystic ovary syndrome (PCOS) allows treating this pathology.

More precisely, the present inventors have studied the effects of in utero AMH exposure on the hypothalamic-pituitary-gonadal axis function of the offspring, by injecting pregnant female mice with AMH toward the end of gestation and by following the neuroendocrine phenotype of their female offspring as adults.

The inventors have found that prenatal AMH-treated (PAMH) female offspring recapitulate the major PCOS cardinal neuroendocrine reproductive features. PAMH female offspring also exhibit masculinization of the sexually dimorphic brain nuclei that regulate reproduction, an increase in the excitatory drive to GnRH neurons and a persistent rise in the GnRH neuronal firing activity in adulthood.

As it is shown in the examples herein, the present inventors have shown that the neuroendocrine reproductive phenotype was completely reversed when AMH injections were combined with a GnRH antagonist treatment prenatally.

The inventors' results disclosed herein show for the first time that fetal exposure to excess AMH can induce permanent changes in the hypothalamic-pituitary-gonadal axis in the offspring and support a novel role for AMH as a fetal programming factor of PCOS.

The inventors' findings have led to determine that prenatal GnRH antagonist treatment as a new therapeutic strategy to prevent the transgenerational transmission of the disease.

As it is also shown in the examples herein, in utero exposure to excessive AMH contribute significantly to the hormonal and gonadal alterations that are observed in PCOS and to impact on fertility by centrally affecting GnRH neuronal excitability.

Thus, the inventors' findings have led to the more general conception of a treatment of PCOS by the administration of a GnRH antagonist.

The present invention relates to a gonadotropin-releasing hormone (GnRH) antagonist for its use in a pregnant woman affected with polycystic ovary syndrome (PCOS) for preventing the occurrence of PCOS in the offspring of the said pregnant woman, i.e. in the female offspring of the said pregnant woman.

This invention concerns the use of a gonadotropin-releasing hormone (GnRH) antagonist for preparing a medicament for preventing the occurrence of polycystic ovary syndrome PCOS in the offspring of a pregnant woman which is affected with PCOS.

This invention pertains to a method for preventing the occurrence of polycystic ovary syndrome (PCOS) in the offspring of a woman affected with PCOS, wherein the said method comprises a step of administering to the said woman, during her pregnancy, a gonadotropin-releasing hormone (GnRH) antagonist.

The present invention also relates to a gonadotropin-releasing hormone (GnRH) antagonist for its use for preventing or treating polycystic ovary syndrome PCOS in female individuals, including adult female individuals.

This invention pertains to the use of a gonadotropin-releasing hormone (GnRH) antagonist for the preparation of a medicament for preventing or treating polycystic ovary syndrome PCOS.

This invention also concerns a method for preventing or treating polycystic ovary syndrome (PCOS) comprising a step of administering a gonadotropin-releasing hormone (GnRH) antagonist to a female individual affected with PCOS.

As used herein, the use of "a" GnRH antagonist encompasses the use of one GnRH antagonist or alternatively of a combination of two or more GnRH antagonists. In preferred embodiments, one GnRH antagonist or a combination of at most two GnRH antagonists is used.

In most preferred embodiments, a GnRH antagonist, or alternatively a combination of two or more GnRH antagonists, are the sole active ingredient(s) used for preventing or treating PCOS according to the present invention.

The use of GnRH antagonists for pre-treating women in the course of an hyperovulation treatment is indeed well-known in the art. In such a pre-treatment with GnRH antagonists, the said GnRH antagonists are used with the aim of targeting the GnRH neurons and thus inducing a transient blockade of GnRH production that would otherwise impair the action of the hormones that are employed for causing hyperovulation. These methods for inducing hyperovulation are especially used for women with a low fertility, in whom are practiced artificial fecundation methods, which artificial fecundation methods encompass In Vitro Fertilization (IVF) methods as well as methods of Intracytoplasmic Sperm Injection (ICSI). These methods of inducing hyperovulation, which are practiced mainly in women having low fertility, generally involve a single injection of a GnRH antagonist, prior to the administration of the hormone(s) used for inducing ovulation. Indeed, these methods involving the administration of a GnRH antagonist at a defined short period of time during a superovulation treatment with hormone(s) may have encompassed women affected with PCOS. However, such treatments aimed at causing the release of a plurality of ovocytes by unfertile women, notably because of the narrow time period window of GnRH antagonist treatment, cannot exert any therapeutic effect against the PCOS pathology itself.

The present invention is described in more detail below.

GnRH Antagonists

As used herein, the term "antagonist" means an agent that down-regulates (e.g., suppresses or inhibits) at least one bioactivity of a protein.

As used herein, a "GnRH antagonist" encompasses a compound which combines with a GnRH receptor on a cell and, at least partially, prevents a physiological response in that cell. GnRH antagonists also encompass compounds that reduce or block the GnRH-encoding gene expression, as well as compounds that reduce or block the GnRH protein production or secretion. GnRH antagonists also encompass nitric oxide as well as nitric oxide donor compounds, and molecules providing the nitric oxide effector cyclic guanosine monophosphate (cGMP) or prolonging its half life that are known in the art to modulate GnRH neuronal activity (Clasadonte et al., 2008, Endocrinology, Vol. 149(2): 587-596). GnRH antagonists also encompass phosphodiesterase inhibitors.

For practicing the present invention, any GnRH antagonist may be used. The one skilled in the art may notably refer to the various GnRH antagonists that are known to date. The one skilled in the art may notably refer to the review article of Schultze-Mosgau et al. (2005, Expert Opinion on Investigational drugs, Vol. 14 (n°9): 1085-1097).

In some embodiments, a GnRH antagonist consists of an antagonistic peptide analogue of GnRH resulting from multiple amino acid substitutions, mainly at positions 1, 2, 3, 6, 8 and 10, in the GnRH decapeptide (Schultze-Mosgau et al., 2005, Expert Opinion on Investigational drugs, Vol. 14 (n°9): 1085-1097).

In some other embodiments, a GnRH antagonist is a non-peptide antagonist compound, such as those described by Shu et al. (2004, Expert Opinion on Therapeutic Patents, Vol. 14: 187-189) or by Armer et al. (2004, Curr Med Chem, Vol. 1: 3017-3028).

Illustratively, a GnRH antagonist may be selected in a group comprising degarelix, ganirelix, cetrorelix and abarelix.

Degarelix is a GnRH antagonist having the CAS reference n° 214766-78-6 and having the IUPAC condensed formula Ac-D-2Nal-D-Phe(4-Cl)-D-3Pal-Ser-Phe(4-S-dihydroorotamido)-D-Phe(4-ureido)-Leu-Lys(iPr)-Pro-D-Ala-NH2. Illustratively, degarelix is available as the pharmaceutical specialty marketed under the brand name Firmagon®.

Ganirelix is a GnRH antagonist having the CAS reference n° 129311-55-3 and having the IUPAC condensed formula Ac-D-2Nal-D-Phe(4-Cl)-D-3Pal-Ser-Tyr-D-Lys(Unk)-Leu-Lys(Unk)-Pro-D-Ala-NH2. Illustratively, ganirelix is available as the pharmaceutical specialty marketed under the brand name Antagon®.

Cetrorelix is a GnRH antagonist having the CAS reference n° 120287-85-6 and having the IUPAC condensed formula Ac-D-2Nal-D-Phe(4-Cl)-D-3Pal-Ser-Tyr-D-Cit-Leu-Arg-Pro-D-Ala-NH2. Illustratively, cetrorelix is available as the pharmaceutical specialty marketed under the brand name Cetrotide®.

Abarelix is a GnRH antagonist having the CAS reference n° 183552-38-7 and having the IUPAC condensed formula Ac-D-2Nal-D-Phe(4-Cl)-D-3Pal-Ser-N(Me)Tyr-D-Asn-Leu-Lys(iPr)-Pro-D-Ala-NH2. Illustratively, abarelix is available as the pharmaceutical specialty marketed under the brand name Plenaxis®.

The one skilled in the art may also refer to the GnRH antagonists that are disclosed in the patent or patent application documents US 2009/0197813, US 2012/0238494, U.S. Pat. Nos. 4,409,208, 4,547,370, 4,565,804, 4,569,927 and 4,619,914.

As mentioned elsewhere in the present specification, GnRH antagonists may be selected in a group comprising nitric oxide, which encompasses inhaled nitric oxide, and nitric oxide donor compounds. Nitric oxide donor compounds are well known in the art and are described notably by Megson (2000, Drugs of the Future, Vol. 25: 701-715), Yamamoto and Bing (2000, Proc Soc Exp Biol Med, Vol. 225: 200-206), Burgaud et al. (2002, Ann NY Acad Sci, Vol. 962: 360-371), Ignarro et al. (2002, Circ Res, Vol. 90: 21-28), Megson and Webb (2002, Expert Opin Investig Drugs, Vol. 11: 587-601) and by
Napoli and Ignarro (2003, Annu Rev Pharmacol Toxicol, Vol. 43: 97-123).

In some embodiments, the nitric oxide donor compounds may be selected in a group comprising L-Arginine (CAS number 74-79-3), DEA NONOate (CAS number 372965-00-9), Sildenafil citrate (CAS number 171599-83-0), (+/−)-S-Nitroso-N-acetylpenicillamine (CAS number 79032-48-7), Molsidomine (CAS number 25717-80-0), 3-Morpholinosydnonimine (CAS number 16142-27-1), Hydroxyguanidine sulfate (CAS number 13115-21-4), Tetrahydrobiopterin dihydrochloride (CAS number 69056-38-8), S-Nitrosoglutathione (CAS number 57564-91-7), Streptozotocin (CAS number 18883-66-4), Nicorandil (CAS number 65141-46-0), Dephostatin (CAS number 151606-30-3), DPTA NONOate (CAS number 146724-95-0), NOC-12 (CAS number 146724-89-2), NOC-18 (CAS number 146724-94-9), NOC-5 (CAS number 146724-82-5), NOC-7 (CAS number 146724-84-7), MAHMA NONOate (CAS number 146724-86-9), PAPA NONOate (CAS number 146672-58-4), Sulfo-NONOate disodium salt (CAS number 146672-58-4), Angeliprimes salt (CAS number 13826-64-7), Diethylamine NONOate (CAS number 372965-00-9), NOR-1 (CAS number 163032-70-0), NOR-2 (CAS number 163032-71-1), NOR-3 (CAS number 163180-49-2), NOR-4 (CAS number 163180-50-5), Spermine NONOate (CAS number 136587-13-8), beta-Gal NONOate (CAS number 136587-13-8), BNN3 (CAS number 6947-38-2), GEA 3162 (CAS number 144575-47-3), GEA 5024 (CAS number 144575-27-9), Sodium nitroprusside dihydrate (CAS number 13755-38-9), 10-Nitrooleate (CAS number 88127-53-1), BEC (CAS number 63107-40-4), NO-indomethacin (CAS number 301838-28-8), Pilotyprimes acid (CAS number 599-71-3), SE175 (CAS number 258278-64-7), V-PYRRO/NO (CAS number 179344-98-0), Vinyl-L-NIO Hydrochloride (CAS number 728944-69-2), AMI-1 sodium salt (CAS number 20324-87-2), DAF-FM DA (CAS number 254109-22-3), GEA 5583 (Santa Cruz Biotechnology catalog number sc-205946), N-Acetyl-D,L-penicillamine disulfide (Santa Cruz Biotechnology catalog number sc-205957), SIN-1A/gammaCDcomplex (CAS number 26687-79-6), 4-phenyl-3-furoxancarbonitrile (CAS number 125520-62-9), JS-K (CAS number 205432-12-8), Lansoprazole Sulfone N-Oxide (CAS number 953787-54-7), NO-Aspirin 1 (CAS number 175033-36-0), Glyco-SNAP-2 (CAS number 188849-82-3), N,N-Dicarboxymethyl-N,N-dinitroso-p-phenylenediamine disodium salt (CAS number 1042969-16-3), (2S)-(+)-Amino-6-iodoacetamidohexanoic acid (CAS number 90764-56-0), 4AF DA (CAS number 3326-33-8), BEC ammonium salt (CAS number 63107-40-4), DAF-2 DA (CAS number 205391-02-2), DAN-1 EE hydrochloride (Santa Cruz Biotechnology catalog number sc-221528), DD1 (Santa Cruz Biotechnology catalog number sc-221531), DD2 (CAS number 56906-22-0), Diethylamine NONOate/AM (CAS number 213768-16-2), Fructose-SNAP-1 Santa Cruz Biotechnology catalog number sc-221631), Glyco-SNAP-1 (CAS number 188849-81-2), Guanylyl Cyclase (Santa Cruz Biotechnology catalog number sc-221697), 8-(4-chlorophenylthio) guanosine 3_5_-cyclic monophosphate sodium (8-pCPT-cGMP) (CAS number 51239-26-0), Hydroxyguanidine hemisulfate (CAS number 6345-29-5) and N-Cyclopropyl-N'-hydroxyguanidine hydrochloride (CAS number 551935-92-3).

It is noticed that Sildenafil citrate is an inhibitor of phosphodiesterase (phosphodiesterase type 5 inhibitor), that is known to act similarly to a nitric oxide donor by prolonging the half-life of cGMP, which is the intracellular effector of nitric oxide.

The above-described GnRH antagonists may be administered in the form of pharmaceutically acceptable non-toxic salts or complexes, depending of the GnRH antagonist which is considered.

In other embodiments, a GnRH antagonist may consists of a relevant micro-RNA molecule (miR) such as the miR155 or miR200, as disclosed in the European patent application filed under n° EP 16 305 459.6 on Apr. 20, 2016 in the name of Inserm. Micro-RNA miR155 is described notably by O'Connell et al. (2007, Proc Natl Acad Sci U S A, Vol. 104:1604-1609). Micro-RNA miR200 is described notably by Korpal et al. (2008, J Biol Chem, Vol. 283 (n°22): 14910-14914). GnRH antagonists also encompass compounds, and especially antagomir nucleic acids, that block the binding of miR155 to a Cebpb-encoding nucleic acid sequence or that block the binding of miR200 to a Zeb1-encoding nucleic acid sequence.

Generally, the GnRH antagonists specified above are available as a powder for injectable formulation and a solvent for reconstitution of the powder. The powder for injectable formulation is a lyophilisate containing the said GnRH antagonist and mannitol, and the solvent consists of water for injection provided in appropriately sized vials.

In preferred embodiments, a GnRH antagonist, or alternatively a combination of two or more GnRH antagonists, is the sole active ingredient or combination of active ingredients that is administered for the purpose of preventing or treating a female individual against PCOS, i.e. either (i) for the purpose of preventing or treating PCOS in a female individual affected, or susceptible to be affected, with this pathology or (ii) for the purpose of preventing the occurrence of PCOS in the offspring of a pregnant woman affected with PCOS.

Embodiments

Treatment of Women Affected with PCOS

As already specified herein, this invention relates to a GnRH antagonist for its use in a woman affected with polycystic ovary syndrome (PCOS) for preventing the occurrence of PCOS in the offspring of the said woman.

In some embodiments, this invention relates to a GnRH antagonist for its use in a pregnant woman affected with polycystic ovary syndrome (PCOS) for preventing the occurrence of PCOS in the offspring of the said pregnant woman.

In some other embodiments, this invention relates to a GnRH antagonist for its use in a non-pregnant woman affected with polycystic ovary syndrome (PCOS) for preventing the occurrence of PCOS in the offspring of the said non-pregnant woman. In this context, a non-pregnant woman especially encompass a woman at a period of time wherein the said woman has the goal to be feconded and thus becoming pregnant.

In some embodiments, prevention of the occurrence of PCOS in the offspring of a pregnant woman affected herself with PCOS is believed to be of optimal efficiency when the administration of a GnRH antagonist to the said pregnant woman is performed at a time period wherein the foetus is at a maturation stage when the GnRH neurons are formed, i.e. at a late stage of gestation. Thus, according to these embodiments, a GnRH antagonist is preferably administered to the pregnant woman affected with PCOS during a period of time ranging from 7 months post-fecundation to 8 months post-fecundation.

In some embodiments, prevention of the occurrence of PCOS in the offspring of a pregnant woman affected herself with PCOS is obtained by performing a reduced number of administration steps of a GnRH antagonist to the pregnant woman within the optimal time period range described herein. In some embodiments, a GnRH antagonist is administered only once within the said optimal time period range (that may also be termed "time period window" herein). In some other embodiments, a GnRH antagonist is administered a plurality of times within the said optimal time period range, such as a plurality of times comprised in a group comprising 2, 3, 4, 5, 6, 7, 8, 9 and 10 administrations or more of a GnRH antagonist during the said optimal time period range.

In some embodiments, a GnRH antagonist is administered daily. In some other embodiments, a GnRH antagonist is administered from 1 time to 6 times a week. In still other embodiments, a GnRH antagonist is administered weekly. In yet further embodiments, a GnRH antagonist is administered from 1 to 4 times each month. In still further embodiments, a GnRH antagonist is administered monthly.

In most preferred embodiments, a GnRH antagonist is administered at a dose where LH pulsatility is restored. Thus, an effective dose of a GnRH antagonist, for the purpose of preventing the occurrence of a PCOS in the offspring of the said pregnant woman or non-pregnant woman, is a dose of GnRH antagonist which is lower than the dose required for blocking LH production.

It is reminded that an effect of blocking the LH production may be sought for affecting the communication between the brain and the ovary in methods for inducing an hyperovulation with the view of collecting the ovules for subsequent in vitro fecondation.

In such a method, a GnRH antagonist is used in combination with an hormone allowing inducing ovulation such as FSH. Thus, according to these methods for an in vitro fecondation, a GnRH antagonist in not used as the sole active ingredient.

In contrast, according to the present disclosure, what is sought is to restore a LH pulsatility in the treated pregnant woman or non-pregnant woman, with the view of normalizing the estrus. Thus, the administration of a dose of a GnRH antagonist that would block LH shall be absolutely avoided for practicing the methods of the present disclosure.

Thus, according to a further aspect of the present disclosure, a GnRH antagonist is the sole active ingredient that is used for preventing or treating a non-pregnant woman or a pregnant woman affected with a PCOS.

Thus, according to this further aspect of the present disclosure, a GnRH antagonist is never used in combination with any other active ingredient, such as is never used in combination with a follicle growth inducing or a hyperovulation inducing active ingredient such as FSH or gonadotrophins As it is illustrated in the examples herein, a GnRH antagonist is preferably administered according to an intermittent administration schedule, such as biweekly, so as to restore normal LH pulsatility/secretion and thus fertility without inducing an undesirable super-ovulation.

In preferred embodiments, a GnRH antagonist is administered according to such an intermittent administration schedule, during a period of time ranging from two weeks to three months, such as for a period of time of one month.

Illustratively, the said GnRH antagonist may consist of a sodium salt of cetrorelix, to be injected subcutaneously.

In preferred embodiments, a GnRH antagonist which is used according to the present disclosure is administered parenterally, by injection.

This invention concerns a method for preventing the occurrence of PCOS in the offspring of a woman affected with PCOS, wherein the method comprises a step of administering to the said woman, during its pregnancy, a GnRH antagonist.

In some embodiments of the method, an administration of a GnRH antagonist is performed within a period of time ranging from 7 months post-fecundation to 8 months post-fecundation.

In some embodiments of the method, the said method comprises a plurality of administration steps of a GnRH antagonist within the optimal time period range. In some of these embodiments, the said method comprises 2, 3, 4, 5, 6, 7, 8, 9 or 10 steps or more of administration of a GnRH antagonist during the said optimal time period range.

In some preferred embodiments of the method, two or more administration steps of a GnRH antagonist are performed during a time period of about four weeks during the time period range of from 7 months post-fecundation to 8 months post-fecundation.

In most preferred embodiments the plurality of administration steps of a GnRH antagonist are performed at regular time intervals during the time period range of from 7 months post-fecundation to 8 months post-fecundation. Illustratively, when four administration steps are to be performed, then these administration steps may be performed at weekly intervals during the time period range of from 7 months post-fecundation to 8 months post-fecundation.

Prevention or treatment of PCOS

As already described elsewhere in the present specification, this invention further relates to a GnRH antagonist for its use for preventing or treating PCOS in a female individual.

For the purpose of the present specification, the term "female individual" encompasses (i) a pre-puberal female individual and (ii) a post-puberal female individual.

A pre-puberal female individual may also be termed "child girl" in the present specification.

A post-puberal female individual may also be termed "woman" in the present specification.

In some embodiments, the administration of a GnRH antagonist to a pre-puberal female individual will allow preventing the occurrence of PCOS in this child girl.

GnRH antagonists that may be used according to these embodiments are described elsewhere in the present specification.

Such a PCOS prevention therapy shall be given specifically to a class of child girls which are susceptible to develop PCOS after puberty. Typically, such a PCOS prevention therapy is preferentially applied to child girls which are the offspring of women who have been affected with PCOS, because it is now known that these child girls are susceptible to develop PCOS themselves, at a time period subsequent to their puberty.

In some embodiments, such PCOS prevention therapy comprise administering a GnRH antagonist to a child girl during a period of time range from 1 year of age to 10 years of age of the said child girl.

Typically, such a PCOS prevention therapy may comprise a plurality of steps of administration of a GnRH antagonist, such as from 2 to 100 steps of administration of a GnRH antagonist, within the said period of time ranging from 1 year of age to 10 years of age of the said child girl.

In preferred embodiments of such a PCOS prevention therapy, administration of a GnRH antagonist to a child girl within a narrower time period range, such as from 2 years of age to 5 years of age of the said child girl, or even within a one year period of time of treatment within the said period of time ranging from 1 year of age to 10 years of age of the said child girl.

In some embodiments, a GnRH antagonist is administered daily. In some other embodiments, a GnRH antagonist is administered from 1 time to 6 times a week. In still other embodiments, a GnRH antagonist is administered weekly. In yet further embodiments, a GnRH antagonist is administered from 1 to 4 times each month. In still further embodiments, a GnRH antagonist is administered monthly. In yet further embodiments, a GnRH antagonist is administered from 1 to 11 times a year.

According to the embodiments, the said GnRH antagonist is the sole active ingredient, or alternatively a combination of two or more GnRH antagonists, the said GnRH antagonist is the sole active ingredient or combination of active ingredients used for the said PCOS prevention therapy.

In some other embodiments, the administration of a GnRH antagonist to post-puberal female individual affected with PCOS will allow treating this pathology.

GnRH antagonists that may be used according to these embodiments are described elsewhere in the present specification.

Because PCOS is normally a chronic state disorder, treating PCOS with a GnRH antagonist will require a plurality of steps of administration of the active ingredient to a woman affected with PCOS.

In some embodiments, such PCOS treatment therapy comprises administering a GnRH antagonist to a woman during a period of time range from 13 years of age to 35 years of age of the said woman.

Typically, such a PCOS treatment therapy may comprise a plurality of steps of administration of a GnRH antagonist, such as from 2 to 100 steps of administration of a GnRH antagonist, within a treatment time period of one to three years, during the said period of time ranging from 13 years of age to 35 years of age of the said woman.

In some embodiments, a GnRH antagonist is administered daily. In some other embodiments, a GnRH antagonist is administered from 1 time to 6 times a week. In still other embodiments, a GnRH antagonist is administered weekly. In yet further embodiments, a GnRH antagonist is administered from 1 to 4 times each month. In still further embodiments, a GnRH antagonist is administered monthly. In yet further embodiments, a GnRH antagonist is administered from 1 to 11 times a year.

GnRH Antagonist Dosages and Compositions

The amounts of a GnRH antagonist that may be administered to a target female individual specified herein are typically those which are conventionally administered to female individuals for other purposes than preventing or treating PCOS. Illustratively, the appropriate amounts of a GnRH antagonist are those which are administered to women affected with a low fertility for inducing hyperovulation. Those amounts of a GnRH antagonist are well-known from the one skilled in the art.

In some embodiments, the dose of a GnRH antagonist which is used for the first administration step may be higher than the dose(s) which is(are) administered for each subsequent administration step(s). In some embodiments, the administration of a higher dose of a GnRH antagonist at the first step of administration will allow a more effective starting of the prevention effect or of the treatment effect, depending of the target female individual which is considered, as compared with a dose for the first administration step which is similar or identical to the dose used for the subsequent administration steps.

Indeed, the one skilled in the art knows well how to adapt a GnRH administration schedule depending of the kind of GnRH antagonist to be administered, depending of the time interval between two administration steps and also depending of the female individual to be treated. Typically, lower GnRH antagonist amounts are administered to pre-puberal female individuals, especially to pre-puberal children under 5 years of age, than to post-puberal women, especially to post-puberal women over 20 years of age.

In some embodiments, an effective amount of said compound is administered to said individual in need thereof.

Within the scope of the instant invention, an "effective amount" refers to the amount of GnRH antagonist (or in some embodiments the amounts of a combination of two or more GnRH antagonists) that alone stimulates the desired outcome, i.e. alleviates or eradicates the symptoms of polycystic ovary syndrome (PCOS).

Within the scope of the instant invention, the effective amount of a GnRH antagonist to be administered may be determined by a physician or an authorized person skilled in the art and can be suitably adapted within the time course of the treatment.

In certain embodiments, the effective amount to be administered may depend upon a variety of parameters, including the material selected for administration, whether the administration is in single or multiple doses, and the individual's parameters including age, physical condition, size, weight, and the severity of the disorder.

In some embodiments, the GnRH antagonist(s), e.g. in the form of a pharmaceutical composition may be administered by any suitable route, including enteral (e.g. , oral), parenteral, intravenous, intramuscular, intra-arterial, subcutaneous, transdermal, intradermal, rectal, intravaginal, intraperitoneal, topical, mucosal, nasal, buccal, sublingual; and/or inhalation; and/or as an oral spray, nasal spray, and/or aerosol.

The mode of administration heretofore employed for similar therapeutics, i.e. GnRH antagonists, can also be employed in the practice of the present invention.

Thus, preferably, the route of administration can be any conventional route where the analog is active, for instance orally, intravenously, subcutaneously, intramuscularly, sublingually, percutaneously, rectally, intranasally or intravaginally.

A GnRH antagonist may be administered at an amount per administration step ranging from 0.01 mg to 3000 mg, depending of the above-described individual parameters.

Thus, in certain embodiments, an effective amount of a GnRH antagonist may comprise from about 0.001 mg to about 3000 mg, per dosage unit, preferably from about 0.05 mg to about 100 mg, per dosage unit.

Within the scope of the instant invention, from about 0.001 mg to about 3000 mg includes, from about 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg and 2950 mg, per dosage unit.

In certain embodiments, a GnRH antagonist may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day.

Illustratively, cetrorelix may be administered at a dose of 0.25 mg at each administration step. In some embodiments, degarelix may be administered at a dose of 0.5 mg at the first administration step and then at a dose of 0.25 mg for each subsequent administration step.

Still illustratively, degarelix may be administered at a dose of 80 mg at each administration step. In some embodiments, degarelix may be administered at a dose of 240 mg at the first administration step and then at a dose of 80 mg for each subsequent administration step Yet illustratively, ganirelix may be administered at a dose of 0.25 mg at each administration step. In some embodiments, degarelix may be administered at a dose of 0.5 mg at the first administration step and then at a dose of 0.25 mg for each subsequent administration step.

Further illustratively, abarelix may be administered at a dose of 110 mg at each administration step. In some embodiments, degarelix may be administered at a dose of 200 mg at the first administration step and then at a dose of 110 mg for each subsequent administration step.

However, in most preferred embodiments, the GnRH antagonist is used at an optimal dose wherein LH production is not completely repressed or blocked, so as to restore LH pulsatility in the treated woman.

This why, according to most preferred embodiments, a GnRH antagonist is used at a dose ranging from 0.1 mg/kg to 0.25 mg/kg.

In some preferred embodiments, for obtaining optimal results, a GnRH antagonist is not used at excessive dosages, at which restoration of LH puslatility may be impaired, such as at a dose of 0.5 mg/kg or more.

In preferred embodiments, each administration dose of a GnRH antagonist comprises an amount of this active ingredient, possibly in a salt form, ranging from 0.1 mg/kg of body weight to 0.25 mg/kg of body weight.

It is generally admitted that the mean weight of an adult fertile woman is of about 70 kg.

Then, a illustrative pharmaceutical compositions which are suitable for practicing the methods of the present disclosure encompasses compositions comprising a GnRH antagonist, e.g. Cetrorelix, at a dose ranging from 7 mg to 20 mg.

Thus, in some preferred embodiments, a GnRH antagonist is administered twice a week and each administration dose comprises an amount of the active ingredient, possibly under a salt form, ranging from 0.1 mg/kg of body weight to 0.25 mg/kg of body weight, during a period of time ranging from two weeks to three months, which includes a period of one month.

This disclosure also relates to a pharmaceutical composition kit which is suitable for a two week- to three month-treatment of a pregnant woman or a non-pregnant woman by a biweekly administration of a GnRH antagonist, or a salt thereof, at a dose ranging from 0.1 mg/kg to 0.25 mg/kg.

An embodiment is illustrated by a kit comprising 7 to 10 dosage units, wherein each dosage unit comprises a GnRH antagonist, or a salt thereof, in an amount ranging from 0.1 mg/kg to 0.25 mg/kg.

According to the present disclosure, it is readily understood that a GnRH antagonist shall not be used at a high dose, such at a dose higher than 0.5 mg/kg, such as at a dose of 3 mg/kg, where a LH blocking effect has a high probability to occur.

Also according to the present disclosure, it shall be understood that a GnRH antagonist shall not be preferably used according to a daily administration schedule, so as to avoid a risk of an excessive and constant repression of LH production, that might impair the normalization of the LH pulsatility which is sought.

A GnRH antagonist which may be used according to the present invention is contained or prepared in a pharmaceutical composition.

In some embodiments, a pharmaceutical composition that may be used according to the invention may be in any suitable form encompassed by the state in the art, e.g. in the form of an injectable solution or suspension, a tablet, a coated tablet, a capsule, a syrup, a suppository, a cream, an ointment, a lotion, and the like.

The administration form can be a tablet, dragee, capsule, pill, nasal mist, aerosol and the like.

Pharmaceutical compositions comprising a GnRH antagonist are generally presented in a powder form of a lyophylisate wherein the active ingredient is combined with a sugar such as mannitol. For its use, the pharmaceutical composition shall be generally reconstituted with an appropriate volume of water or of chloride sodium solution. Then, the resulting liquid pharmaceutical composition may be administered by the appropriate administration route.

In some embodiments, a GnRH antagonist that may be used according to the invention may be combined with pharmaceutically acceptable excipients, and optionally sustained-release matrices, such as biodegradable polymers, to form therapeutic compositions.

In certain embodiments, the pharmaceutic composition may further comprise one or more salts, one or more buffering agents, and/or one or more preservatives.

Within the scope of the instant invention, a "pharmaceutically acceptable carrier" refers to a pharmaceutically acceptable material, composition or vehicle, such as a liquid or solid filler, diluent, excipient, solvent or encapsulating material, involved in carrying or transporting a prophylactically or therapeutically active agent.

In certain embodiments, a suitable pharmaceutically acceptable carrier may be selected in a group including sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and the like.

In some embodiments, the active agent is administered by oral administration, systemic intravenous administration.

The present invention is further illustrated by, without in any way being limited to, the examples herein.

EXAMPLES

Most of the Materials and Methods are disclosed in the figure legends in the present disclosure. Supplementary Materials and Methods are also disclosed hereafter.

A. Materials and Methods

A.1. Study Population: Human Patients

Blood samples were derived from the population-based Uppsala Biobank of Pregnant Women, where blood samples are collected in conjunction with the routine ultrasound screening during gestational weeks 16-19. Gestational length was determined according to the ultrasound-based estimated date of birth. Eligible women were (1) 18 years or older, (2) Swedish-speaking, and (3) without blood-borne disease. In Sweden, all pregnant women are invited to a routine ultrasound examination, and approximately 97 percent of the pregnant population participate. In Uppsala County, all routine ultrasound examinations are performed at Uppsala University Hospital, which is also the only available delivery ward within the county. Hence, the Biobank subjects represent a population-based sample. Invitation to participate in the Biobank is done at random, when a research nurse is available. Approximately 30% of the respondents decline participation, and it is estimated that the Biobank covers approximately half of the pregnant population of Uppsala County (Granfors et al., 2013, J Clin endocrinology and metabolism, Vol. 98: 2687-2692). Upon inclusion, brief demographic data are collected, including ongoing chronic disorders, ongoing medication, smoking, height and weight. Following written informed consent, a plasma sample is collected. The sample was centrifuged within two hours and stored at −80° C.

By September 2013, 160 women with PCOS had donated a blood sample to the biobank, and from these blood samples, 32 normal-weight and 34 obese women with PCOS were selected for the purpose of the present study based on their age (27-39 years old). PCOS was diagnosed according to Rotterdam criteria, i.e. with presence of two of the following criteria: 1) polycystic ovaries on transvaginal ultrasound, 2) oligoamenorrhea and 3) hyperandrogenism (either biochemical or clinical). Hyperandrogenism was defined as pre-pregnancy hyperandrogenism: either elevated testosterone, or elevated free androgen index (testosterone/sex hormone binding globulin>0.05) or pre-pregnancy hirsutism as judged at the time of diagnosis. All women with PCOS had normal prolactin levels and thyroid function tests. Based on the initial, pre-pregnancy, diagnostic work-up, each woman was further phenotyped as hyperandrogenic PCOS (with signs of biochemical and/or clinical hyperandrogenism) or normoandrogenic PCOS. The medical records of all women with PCOS were scrutinized to ensure a correct diagnosis of PCOS, and to obtain information on obstetric and perinatal outcomes.

For each woman with PCOS an age- and BMI matched healthy control was chosen. Each control had donated the blood sample during the same week as the respective case and were healthy according to the self-report. The medical records of the controls were reviewed to ensure than none had been diagnosed with PCOS or female factor infertility previously. Three blood samples from the controls could not be retrieved; hence 63 healthy controls were available for analysis. All women gave written informed consent for inclusion and the study has been approved by the Independent Ethical Review Board of Uppsala, Sweden.

A.2. AMH Levels During Pregnancy

Serum AMH levels were measured on samples stored at −80° C. using the fully automated Acces Dxi sandwich immunoassay (B13127, Beckman Coulter). This assay measures the proAMH and the cleaved AMHN,c complex and uses recombinant human AMH as a calibrator. The limit of quantification of the assay is 0.57 pmol/L. Its intra- and inter-assay imprecision is less than 5%. Results are expressed in pmol/L.

A.3. Animals

Timed-pregnant female wild-type C57BL/6J (B6) (Charles River, USA) and transgenic Gnrh-Gfp (Spergel et al., 1999, J Neurosci, Vol. 19: 2037-2050) were group-housed under specific pathogen-free conditions in a temperature-controlled room (21-22° C.) with a 12-h light/dark cycle and ad libitum access to food and water. Standard diet (9.5 mm Pelleted RM3, Special Diets Services, France) was given to all mice during breeding, lactation and growth of young stock. Nutritional profile of the standard diet RM3 is the following: Protein 22.45%, Fat 4.2%, Fiber 4.42%, Ash 8%, Moisture 10%, Nitrogen free extract 50.4%; Calories: 3.6 kcal/gr.

Mice were randomly assigned to groups at the time of purchase or weaning to minimize any potential bias. No data sets were excluded from analyses.

C57BL1/6J Gnrh-Gfp transgenic mice have been previously characterized (Spergel et al., 1999, J Neurosci, Vol. 19: 2037-2050). Animal studies were approved by the Institutional Ethics Committees of Care and Use of Experimental Animals of the University of Lille 2 (France; Ethical protocol number: APAFIS #2617-2015110517317420 v5). All experiments were performed in accordance with the guidelines for animal use specified by the European Council Directive of 22 September 2010 (2010/63/EU). The sample size, sex and age of the animals used is specified in the text and/or figure legends.

A.4. Genotyping

Tail biopsies were used to isolate genomic DNA to identify the sex of embryos and mice at birth using Ubel primers: Ubel (forward), 5'CACCTGCACGTTGCCCTT-3' (SEQ ID NO. 1) and Ubel (reverse), 5'TGGATGGTGTGGCCAATG-3'(SEQ ID NO. 2). Males were identified with two bands marking both X (252 bp) and Y (334 bp) chromosomes and females with a single band representing only the X chromosome at 252bp. Gnrh-Gfp transgenic animals were genotyped as previously described (Spergel et al., 1999, J Neurosci, Vol. 19: 2037-2050).

A.5. Prenatal Anti-Müllerian Hormone (PAMH) Treatment

Timed-pregnant adult (3-4 months) C57BL6/J (B6) (Charles River, USA) dams were injected daily intraperitoneally (i.p.) from embryonic day (E) 16.5 to 18.5 with 200 μL of a solution containing respectively: 1) 0.01M phosphate buffered saline (PBS, pH 7.4, prenatal control-treated), 2) PBS with 0.12 mg $Kg^{-1}$/d human anti-Müllerian hormone (AMH) (AMHc, R&D Systems, rhMIS 1737-MS-10, prenatal AMH (PAMH)-treated), 3) PBS with 0.12 mg $Kg^{-1}$/d AMH and 0.5 mg $Kg^{-1}$ of the GnRH antagonist, cetrorelix acetate (Sigma, Cat #C5249; PAMH+GnRH antag-treated), 4) 0.5 mg $Kg^{-1}$/d of cetrorelix acetate in PBS (prenatal GnRH antag-treated), and 5) PBS with 0.12 mg $Kg^{-1}$/d proAMH (Origene Technologies, Cat # TP308397; prenatal proAMH-treated, PproAMH). Gnrh-Gfp adult females (P60-P90) were paired with males and checked for copulatory plugs, indicating day 1 of gestation. Pregnant Gnrh-Gfp dams were given either 200 μl i.p. injections of PBS (control-treated) or 0.12 mg $Kg^{-1}$/d AMHc in PBS from E16.5, E17.5 and E18.5. PAMH-Gnrh-Gfp and Control-Gnrh-Gfp offspring were weaned, genotyped and phenotyped during postnatal life.

A.6. Assessment of Phenotype, Estrous Cycle and Fertility

Control, PAMH, PAMH+GnRH antag, GnRH antag, and PproAMH female offspring were weaned at post-natal day (P) 21 and checked for vaginal opening (VO) and time of first estrus. Anogenital distance (AGD) and body mass (grams, gr) were measured at different ages during post-natal development (P30, 35, 40, 50 and 60). At VO and in adulthood (P60), vaginal smears were performed daily for 16 consecutive days (4-cycles) for analysis of age of first estrus and estrous cyclicity. Vaginal cytology was analyzed under an inverted microscope to identify the specific day of the estrous cycle. The reproductive competency of these animals was determined by pairing the following mice: Control females mated with untreated C57BL6J (B6) wild-type males, PAMH females mated with PAMH males, PAMH+GnRH antag females mated with PAMH+GnRH antag males, and GnRH antag females mated with GnRH antag males for a period of 3 months. Not experienced males and primiparous females, selected from at least three different litters, were used for the 90-days mating protocol test.

Number of pups/litter (number of pups), fertility index (number of litters per females over 3 months), and time to first litter (number of days to first litter after pairing) were quantified per treatment and pairing.

A.7. Postnatal GnRH Antagonist Treatment in PAMH Mice and Assessment of Phenotype and Hormone Levels.

PAMH adult female offspring were cycled for 12-days before GnRH antagonist treatments. Vaginal cytology was analyzed under an inverted microscope to identify the specific day of the estrous cycle and recorded. Animals were injected intraperitoneally (i.p.) with 200 μL of a solution containing 0.01M phosphate buffered saline (PBS, pH 7.4) with Cetrorelix acetate at the dose of 0.05 and 0.5 mg/Kg, every second day, or daily with Cetrorelix acetate at the dose of 5 mg/Kg. Tail-blood samples were collected for LH measurements twice before the beginning of the treatments, and at day 2 and 6 of each treatment as well as 4 days after the last injection (no treatment), that followed each administration period. Estrous cyclicity was monitored every day at the same time of day for the 12 days during postnatal GnRH antagonist treatments.

A.8. Ovarian Histology

Ovaries were collected from 3-4-month-old diestrus mice, immersion-fixed in 4% PFA solution and stored at 4° C. Paraffin-embedded ovaries were sectioned at a thickness of 5-μm (histology facility, University of Lille 2, France) and stained with hematoxylin-eosin (Sigma Aldrich, Cat # GHS132, HT1103128). Sections were examined throughout the ovary. Total numbers of large antral follicles (containing a single large antrum), atretic and cysts-like follicles (large fluid-filled cysts with an attenuated granulosa cell layer, dispersed theca cell layer, and an oocyte lacking connection to the granulosa cells), and corpora lutea (CL) were classified and quantified as previously reported (Caldwell et al., 2017, Proc Natl Acad Sci USA, Vol. 114: E3334-E3343). To avoid repetitive counting, each follicle was only counted in the section where the oocyte's nucleolus was visible. Using an ocular scale the follicles were classified by diameter into preantral, large growing (200-400 μm) and cystic follicles (>400 μm). To avoid repetitive counting, CL were counted every 100 μm by comparing the section with the preceding and following sections. CL were characterized by a still present central cavity, filled with blood and follicular fluid remnants or by prominent polyhedral to round luteal cells.

A.9. Perfusions

Adult diestrus female mice and adult control males (P60-P90) were anesthetized with intraperitoneal (i.p.) injections with 100 mg $kg^{-1}$ of ketamine-HCl and 10 mg $kg^{-1}$ xylazine-HCl and perfused transcardially with 20 ml of saline, followed by 100 ml of 4% paraformaldehyde (PFA) in 0.1M phosphate buffer (PB) (4% PFA/0.1M PB; pH 7.6). Brains were collected, post-fixed in the same fixative for 2 h at 4° C., cryoprotected overnight in PB/Sucrose 30% at 4° C., embedded in OCT-embedding medium (Tissue-Tek), frozen and stored at −80° C. until cryosectioning.

A.10. Immunohistochemistry

Tissues were cryosectioned coronally (Leica cryostat) at 35 μm for free-floating immunohistochemistry. Sections were blocked in an incubation solution containing Tris-buffered saline (TBS 0.05M, pH 7.6), 0.25% bovine serum albumin (BSA; Sigma, A9418), 0.3% Triton X-100 (TBS-T; Sigma, T8787) with 10% normal donkey serum (NDS; D9663; Sigma) for 2-hrs at room temperature before incubation with the following different primary antisera (depending on experiment) for 72-hrs at 4° C.: guinea pig anti-GnRH (EH #1018, 1:10000) (Hrabovsky et al., 2011, Frontiers in Endorinology, Vol. 2: 80; Casoni et al., 2016, Development: Vol. 143: 3969-3981), a generous gift from Dr. Erik Hrabovszky (Laboratory of Endocrine Neurobiology, Institute of Experimental Medicine of the Hungarian Academy of Sciences, Budapest, Hungary), polyclonal rabbit anti-GFP (Abcam, Cat # ab6556; 1:1000), mouse monoclonal anti-vesicular GABA Transporter, vGaT) antibody (Synaptic Systems, Cat. #131 001; 1:500), polyclonal guinea pig anti-vesicular glutamate transporter 2 (vGluT2) (Synaptic Systems, Cat. #135 404; 1:500), monoclonal mouse anti-Tyrosine Hydroxylase (TH) antibody (Millipore; MAB318; 1:3000), polyclonal guinea pig-anti-($Arg^8$)-Vasopressin (Peninsula Laboratories, San Carlos, CA; Cat #T-5048; 1:2500), polyclonal rabbit anti-cFos (Santa Cruz Biotechnology, Cat #sc-52, 1:5000), and a polyclonal rabbit anti-kisspeptin (1:10000; #566, A. Caraty, Institut National de la Recherche Agronomique) (Clarkson et al., 2014, J Neurosci, Vol. 34: 15297-15305). After TBS rinses, immunoreactivity was revealed using the corresponding secondary antibodies, Alexa-Fluor 488-conjugated (1:400; Life Technologies, reference Molecular Probes, Invitrogen, A21206), Alexa-Fluor 647-conjugated 1:400, Life Technologies, Cat #A31573, A31571), and Alexa-Fluor 568-conjugated (1:400, Life Technologies, Cat #A10042, A10037) for 90-mins in incubation solution RT. After TBS washes, sections were incubated with 0.02% Hoechst (H3569; Invitrogen) in TBS-T for 15-mins at RT and mounted on gelatin-coated slides and coverslipped with mowiol medium (Sigma, Cat #81381).

Sections were examined using an Axio Imager.Z1 Apo-Tome microscope (Carl Zeiss, Germany) equipped with a motorized stage and an AxioCam MRm camera (Zeiss). For confocal observation and analyses, an inverted laser scanning Axio observer microscope (LSM 710, Zeiss) with an EC Plan NeoFluor×100/1.4 numerical aperture oil-immersion objective (Zeiss) was used with an argon laser exciting at 488 nm and helium laser exciting at 543 nm (Imaging Core Facility of IFR114, of the University of Lille 2, France).

3D rendering and movies of GnRH neurons were generated using Imaris ×64 software (version 7.6.1, Bitplane).

A.11. Immunohistochemical Analysis

A.11.1. Assessment of Fos-GnRH Co-Expression

Adult C57BL6/J (B6) (Charles River, USA) females in diestrus were given i.p. injections of a solution containing 200 μL of 0.01M phosphate buffered saline (PBS), pH 7.4) or PBS with 0.12mg Kg$^{-1}$/d AMHc (R&D Systems, rhMIS 1737-MS-10) at 10h00. 90-mins after injections, each mouse was anaesthetized and perfused transcardially as described below (Perfusions). Brains were collected, post-fixed in the same fixative for 2 h at 4° C., embedded in OCT-embedding medium (Tissue-Tek), frozen and cryosectioned coronally (Leica cryostat) at 35 μm for free-floating immunohistochemistry. Sections were processed for dual-label Fos-GnRH immunohistochemistry.

Analysis of the double-labeled tissue was undertaken by counting the number of single-labeled and dual-labeled GnRH neurons in the preoptic area (POA: OVLT). Two-three brain sections representing the POA were counted per mouse. Stacks of images containing both GnRH and Fos immunoreactivity were scanned using a 20× objective to image dually Fos-GnRH positively labelled cells for quantification. Activated neurons were identified as expressing Fos in the nucleus of the GnRH-immunoreactive cell. The number of GnRH neurons co-expressing Fos was quantified and grouped to produce a mean percentage of the co-expression of GnRH-Fos in both PBS- and AMH-treated adult diestrus female mice. The data from each mouse were then grouped to provide the median percentage±interquartile range (IQR).

For the analysis of the total Fos-immunoreactive cells in the POA, the same sections described above were examined using a 10× objective. The total number of Fos positive cells per POA (OVLT) section in each treatment was quantified using the particle analysis program from Fiji-NIH software. To analyze IHC data, the total number of Fos-positive cells in the OVLT were quantified and averaged across the OVLT sections from each animal and treatment.

A.11.2. Analysis of Sexually Dimorphic Brain Nuclei

For single-labeled Tyrosine Hydroxylase (TH) IHC, the number of TH-immunoreactive (ir) cell bodies located within anteroventral periventricular nucleus were counted. For single-labeled Vasopressin (VP) immunohistochemistry, the number of VP-ir cell bodies located within the bed nucleus stria terminalis (BNST) and Medial Amygdala (MeA) were counted. For both TH and VP single-labeled IHC, each section containing the AVPV (for TH) or the BNST and MeA (for VP) were analyzed in each sex, mouse and treatment (three to five sections per mouse). For the single-label kisspeptin IHC, the number kisspeptin-positive cell bodies were counted in the rostral periventricular area of the third ventricle (RP3V), which comprises the anteroventral periventricular nucleus (AVPV), the preoptic periventricular nucleus. Two brain sections at each level of the RP3V were analyzed in each mouse, and the number of kisspeptin positive cells counted and combined to produce the mean number of kisspeptin neurons per section for the RP3V of each mouse.

The mean number of TH-, VP- and Kiss-immunoreactive neurons counted per section for the sexually dimorphic brain regions of each mouse and treatment were then grouped to provide the mean±s.e.m. values for the experimental groups.

A.11.3. Assessment of GnRH Neuron Spine Density

Coronal brain sections from adult (P60-90) female Control-Gnrh-Gfp and PAMH-Gnrh-Gfp animals were analyzed for GnRH neuron spine density.

Analysis of Spine Numbers on Gnrh-Gfp Neurons: Ten GFP-immunoreactive GnRH neurons located within the rPOA were randomly chosen from adult (P60-P90) diestrus Control-Gnrh-Gfp (n=5) and PAMH-Gnrh-Gfp female mice (n=5) and were imaged using a LSM 710, Zeiss upright confocal laser scanning microscope equipped with LSM 710 software. For each GnRH-GFP cell, a stack of images at 0.25 μm intervals were collected using a 100× objective and 2× digital zoom function throughout the entire depth of the GFP-immunoreactive neuron. Images containing the cell body and initial portion of the primary dendrite (up to 45 μm) were collected. The z-series of slices were scanned and soma and dendritic spine density were determined. Spines were identified as protrusions from the somata or dendrite and defined as being less than 5 μm in length from the soma or proximal dendrite (the dendrite with the greatest circumference extending from the GnRH soma). GnRH neuron soma spine density was expressed as the number of spines per micrometer relative to the soma circumference. Spine density was quantified for consistency every 15 μm along the entire length of the proximal GnRH dendrite (0-45 μm) as 45 μm was the longest length of the proximal dendritic length that could be imaged before the dendrite exited the section. Spine density was expressed as the expressed as the number of spines/μm.

A.11.4. Analysis of vGaT or vGluT2 Appositions on Gnrh-Gfp Neurons

Coronal brain sections from adult (P60-90) female Control-Gnrh-Gfp and PAMH-Gnrh-Gfp animals were analyzed for GnRH neuron spine and vGaT or vGluT2 density.

8 to 10 GFP/vGaT or GFP/vGluT2 double labeled neurons located within the rPOA from Control;Gnrh-Gfp and PAMH;Gnrh-Gfp adult (P60-P90) diestrus female mice were imaged using the same criteria above. A z-series stack of images using a 100× objective to estimate the density of vGaT or vGluT2 appositions. A contact was defined when there were no black pixels between the primary Gnrh-Gfp dendritic spine and vGaT or vGluT2 positive terminals. For each image, the number of vGaT- or vGluT2-labeled puncta directly opposed to GFP-labeled neuronal soma and dendrite (up to 45 μm along the GnRH primary dendrite) were counted and combined to provide the mean values for each cell. The primary GFP-immunoreactive dendrite could not be followed for more than 45 μm from the cell body, and therefore, as with the spine density analysis, we determined the number of vGaT appositions in the initial 15 μm for every 15 µm until the dendrite exited the section. Data are presented as vGaT or vGluT2 appositions/µm.

A.12. Fluorescent AMH Assays

Recombinant bioactive AMH (AMHc, R&D Systems, rhMIS 1737-MS-10) was tagged with a fluorescent dye (d2; MW: approx. 800 Da, maximum light output at 665 nm) by Cisbio Bioassays (Codolet, France) as previously described for other hormones (Balland et al., 2014, Cell Metabolism, Vol. 19: 293-301; Schaeffer et al., 2013, Proc Natl ACad Sci USA, Vol. 110: 1512-1517; Xu et al., 2017, EMBO Mol Med, Vol. 9: 1379-1397). Fluorescently-labeled bioactive AMH (2.5 nmoles/animal; Cisbio Bioassays) was injected into the jugular vein of pregnant mice (E16.5), anesthetized with ketamine/xylazine, and mice were sacrificed 2 min later. Dams' brains, fetal brains and placentae were collected and immersion-fixed in 4% PFA overnight at 4° C. Brains were cryoprotected overnight in PB/Sucrose 30% at 4° C., embedded in OCT-embedding medium (Tissue-Tek), frozen and stored at −80° C. until cryosectioning. Placentae were processed for iDisco tissue-clearing as described below.

A.13. Cetrorelix Measurement in Biological Samples

A.13.1. Sample Preparation for Nano-HPLC-HRMS Analysis

Timed-pregnant adult (3-4 months) C57BL6/J (B6) (Charles River, USA) dams were injected daily intraperitoneally (i.p.) from embryonic day (E) 16.5 to 18.5 with 200 µL of a solution containing respectively: 1) 0.01M phosphate buffered saline (PBS, pH 7.4, prenatal control-treated), 2) PBS with 0.5 mg $Kg^{-1}$ of the GnRH antagonist, cetrorelix acetate (Sigma, Cat #C5249; GnRH antag-treated). At E19.5, dams were anesthetized with ketamine/xylazine, and sacrificed by cervical dislocation. Dams' brains and fetal brains were collected, snap-frozen in liquid nitrogen and stored at −80° C. until nano-HPLC-HRMS experiments.

Murine maternal and embryo brain samples were prepared adapting the procedure described (Wang et al., 2014, Vol. 1345: 98-106). Briefly, the brains were weighted, homogenized with 1% formic acid in cold acetonitrile and incubated for 15 minutes at −20° C. After centrifugation, the supernatant was freeze-dried and reconstituted with 3% acetic acid and 1% trifluoroacetic acid (TFA). all of the solvents were from Sigma-Aldrich Merck (Milan, Italy). The reconstituted sample was purified with a solid phase extraction using a Phenomenex polymeric reversed phase cartridge (Strata-X 33 µm Polymeric Reversed Phase, 60 mg/3 mL, Phenomenex, Bologna, Italy). The cartridges were equilibrated with methanol and water solution of acetic acid and TFA (96:3:1 v/v), loaded with sample, washed with a 70:30 solution of water solution with acetic acid and TFA (96:3:1 v/v) and methanol, and eluted with a 90:10 solution of methanol and 3% acetic acid. The eluted solution was gently dried under stream on nitrogen and reconstituted with 0.1% formic acid. When brains were homogenized, an internal standard (ganirelix, with empirical formula $C_{80}H_{113}ClN_{18}O_{13}$) was added to obtain a final concentration of 100 ng/ml.

A.13.2. Nano-HPLC-HRMS Analysis Parameters

A Dionex Ultimate 3000 (Thermo Scientific, Milan, Italy) nano-HPLC instrument coupled to a Orbitrap Fusion (Thermo Scientific, Milan, Italy) high resolution hybrid mass analyzer was used.

The separation was achieved with an EASY-Spray PepMap® column (C18, 2 µm, 100 Å, 75 µm×500 mm, Thermo Scientific, Milan, Italy) using formic acid 0.1% in water (solvent A) and in acetonitrile:water 8:2 (solvent B) as mobile phases (ultrapure solvents for nano-LC, SigmaAldrich, Milan, Italy). The gradient conditions were as follow: 5% B for 5 minutes isocratic, up to 100% B in 30 minutes and reconditioned for at least 20 minutes. The first 5 minutes of isocratic flow was mandatory for the preconcentration step on a ρ-precolumn (C18 PepMap 100, 300 µm i.d.×5 mm, Thermo Scientific, Milan, Italy), and water with 0.1% formic acid and 0.05% TFA. The injection volume was 1 µL and the flow rate 300 nL $min^{-1}$.

The column was equipped with a nanoESl source and the capillary voltage was 2000 V in positive ion mode. The ion transfer tube temperature was 275° C. and the pressure was standard (0.008 Torr). Full scan spectra were acquired in the range of m/z 350-2000. $MS^n$ spectra were acquired in the range between the ion trap cut-off and precursor ion m/z values. CID collision energy was selected for each analyte to allow the survival of 5-10% of the chosen precursor ion. High resolution spectra were acquired with a resolution of 60000 (FWHM) and the mass accuracy of recorded ions (vs. calculated) was ±5 ppm units (without internal calibration).

A.14. Tissue Clearing

We used iDisco clearing protocol, as previously described (Renier et al., 2014, Cell, Vol. 159: 896-910). Samples were washed in PBS (twice for 1 h), followed by 50% methanol in PBS (once for 1 h), 80% methanol (once for 1 h) and 100% methanol (twice for 1 h). Next, samples were bleached in 5% $H_2O_2$ in 20% DMSO/methanol (2 ml 30% $H_2O_2$/2 ml DMSO/8 ml methanol, ice cold) at 4° C. overnight. Next, samples were washed in methanol (twice for 1 h), in 20% DMSO/methanol (twice for 1 h), 80% methanol (once for 1 h), 50% methanol (once for 1 h), PBS (twice for 1 h), and stored in PBS at 4° C. until processing for immunohistochemistry or tissue-clearing.

Samples were then incubated at RT on a rotating wheel at 12 rpm in a solution containing: 20% MeOH, 40% MeOH, 60% MeOH, 80% MethOH, 100% MeOH, 100% MeOH; 1 h each. Delipidation was achieved with an overnight incubation in ⅔ DCM+⅓ Methanol, followed by a 30-min wash in 100% DCM (Dichloromethane; Sigma-Aldrich). Samples were cleared in dibenzylether (DBE; Sigma-Aldrich) for 2 h at RT on constant agitation and in the dark. Finally, samples were moved into fresh DBE and stored in glass tube in the dark and at RT until imaging.

3D imaging was performed as previously described (Belle et al., 2017, Cell, Vol. 169: 161-173); Belle et al., 2014, Cell Reports, Vol. 9: 1191-1201). An ultramicroscope (LaVision BioTec) using InspectorPro software (LaVision BioTec) was used to perform imaging. The light sheet was generated by a laser (wavelength 488 or 561 nm, Coherent Sapphire Laser, LaVision BioTec) and two cylindrical lenses. A binocular stereomicroscope (MXV10, Olympus) with a 2x objective (MVPLAPO, Olympus) was used at different magnifications (1.6×, 4×, 5×, and 6.3×). Samples were placed in an imaging reservoir made of 100% quartz (LaVision BioTec) filled with DBE and illuminated from the side by the laser light. A PCO Edge SCMOS CCD camera (2,560×2,160 pixel size, LaVision BioTec) was used to acquire images. The step size between each image was fixed at 2 µm.

A.15. Pulsatile LH Measurements

Diestrus female adult mice were habituated with daily handling for 3-weeks. Blood samples (5 µl) were taken from the tail at 10-min intervals for 2 h (between 10 a.m. and 12 p.m.) on the estrous cycle stage of diestrus, diluted in 45 µl PBS-Tween (0.05%) and immediately frozen and kept at −80° C. LH levels were determined by the previously described sensitive LH sandwich ELISA (Koninger et al., 2013, Reproductive biology and endocrinology, RB&E, Vol. 11: 60). A 96-well high-affinity binding microplate (Corning) was coated with 50 µl of capture antibody (monoclonal antibody, anti-bovine LH beta subunit, 518B7; University of California, Lillian Sibley UC Davis) at a final dilution of 1:1000 (in $Na_2CO_3/NaHCO_3$, 0.1M, pH 9.6) and incubated overnight at 4° C. Wells were incubated with 200 µl of blocking buffer (5% (w/v) skim milk powder in 1×PBS-T (0.01M PBS, 1.09 g of $Na_2HPO_4$ (anhydrous), 0.32 g of $NaH_2PO_4$ (anhydrous) and 9g NaCl in 1 L distilled water with 0.05% Tween 20 (pH 7.4, Sigma #P9416)) for 2 hr at RT. A standard curve was generated using a two-fold serial dilution of mLH (reference preparation, AFP-5306A; National Institute of Diabetes and Digestive and Kidney Diseases National Hormone and Pituitary Program (NIDDK-NHPP) in 0.25% (w/v) BSA (Sigma, A9418) in PBS-T. The LH standards and blood samples were incubated with 50 µl of detection antibody (polyclonal antibody, rabbit LH antiserum, AFP240580Rb; NIDDK-NHPP) at a final dilution of 1:10000 for 1.5 h at RT. Each well containing bound substrate was incubated with 50 µl of horseradish peroxidase-conjugated antibody (polyclonal goat anti-rabbit; Vector Laboratories, PI-1000) at a final dilution of 1:10000. After a 1.5-h incubation, 100 µl 1-Step™ Ultra TMB-Elisa Substrate Solution (ThermoFisher Scientific, Cat #34028) was added to each well and left at RT for 10 min. The reaction was stopped by the addition of 50 µl of 3 M HCL to each well, and absorbance was read at a wavelength of 490 nm. Pulses were confirmed using DynPeak (Steyn et al., 2013, Endocrinology, Vol. 154: 4939-4945).

A.16. LH and T ELISA Assays

For the analysis of circulating LH and T levels, animals were decapitated and trunk blood from adult (P60) animals and P0 pups (1-2 hrs after birth) were collected in sterile Eppendorf tubes and left on ice until centrifugation. Plasma was collected and stored at −80° C. until use. LH levels were determined by a sandwich ELISA, as described previously (Vidal et al., 2012, PloS one, Vol. 7: e39001), using the mouse LH-RP reference provided by A. F. Parlow (National Hormone and Pituitary Program, Torrance, CA). Plasma T levels were analyzed using a commercial ELISA (Demeditec Diagnostics, GmnH, DEV9911) (Moore et al., 2015, Proc Natl Acad Sci USA, Vol. 112: 596-601) according to the manufacturers' instructions.

A.16.1. LH and T Measurement in Pregnant Mice

Timed-pregnant female C57BL6/J (B6) darns were treated with i.p. injections of 200 µL of PBS or 0.12mg $Kg^{-1}/d$ AMH in PBS from E16.5-E18.5. At E19.5, pregnant-treated dams were decapitated and trunk blood was harvested for LH and Testosterone measurements. Plasma was collected after centrifugation of blood samples at 3000 g for 15 mins at 4° C. and stored at −80° c. until use. Mean T and LH levels were determined as described above.

A.16.2. LH and T Measurement in P0 Mice

Timed-pregnant C57BL6/J (B6) dams were given i.p injections of 200 µL PBS or 0.12 mg $Kg^{-1}/d$ AMH in PBS from E16.5-E18.5. Dams were allowed to deliver naturally. Pups were harvested 2 hrs after birth. Tail biopsies of pups were taken to determine the sex of each animal (see Genotyping). Trunk blood and was collected from P0 males, control females and PAMH female pups for analysis of circulating testosterone and LH levels. Plasma was collected after centrifugation of blood samples at 3000 g for 15 mins at 4° C. and stored at −80° C. until use. T and LH levels were determined as described above.

A.17. Quantitative RT-PCR Analyses

E19.5 placental tissue from female control and PAMH embryos was isolated for total RNA was using Trizol (ThermoFisher Scientific, Cat #15596026) and the RNeasy Lipid Tissue Mini Kit (Qiagen; Cat #74804) using the manufacturer's instructions. For gene expression analyses, mRNAs obtainHSD3ed from E19.5 placental tissue were reverse transcribed using SuperScript® IV Reverse Transcriptase (Life Technologies). Real-time PCR was carried out on Applied Biosystems 7900HT Fast Real-Time PCR system using exon-boundary-specific TaqMan® Gene Expression Assays (Applied Biosystems): Amhr2 (AMHR2-Mm00513847_m1); Cyp19a1 (Cyp19a1-Mm00484049_m1); Cyp11a1 (Cyp11a1-Mm00490735_m1); HSD3b1 (Hsd3b1-Mm01261921_mH); GnRH (Gnrh-Mm01315604_m1); GnRH-R (Gnrhr-Mm00439143_m1); LH-R (Lhcgr-Mm00442931_m1). Control housekeeping genes: ActB (ActB-Mm00607939_s1); GAPDH (GAPDH-Mm99999915_g1).

Quantitative RT-PCR was performed using TaqMan® Low-Density Arrays (Applied Biosystems) on an Applied Biosystems thermocycler using the manufacturer's recommended cycling conditions. Gene expression data were analyzed using SDS 2.4.1 and Data Assist 3.01 software (Applied Biosystems), with ActB and GAPDH as control house-keeping mRNA following a standardized procedure. Values are expressed relative to control values, as appropriate, set at 1.

A.18. Brain slice electrophysiology preparation and recordings

Gnrh-Gfp adult females (3-4 months) were paired with adult Gnrh-Gfp males (3-4 months) and checked for copulatory plugs. Pregnant Gnrh-Gfp dams were given 200 i.p. injections of PBS or 0.12 mg $Kg^{-1}/d$ AMH in PBS on days 16.5, 17.5 and 18.5 of gestation. Adult (3-4 months) female diestrus Control;Gnrh-Gfp and PAMH;Gnrh-Gfp offspring were anaesthetized with isoflurane, and, after decapitation, the brain was rapidly removed and put in ice-cold oxygenated ($O_2$ 95%/$CO_2$ 5%) artificial cerebrospinal fluid (ACSF) containing the following (in mM): 120 NaCl, 3.2 KCl, 1 $NaH_2PO_4$, 26 $NaHCO_3$, 1 $MgCl_2$, 2 $CaCl_2$, 10 glucose, pH 7.4 (with $PO_2$ 95%/$CO_2$ 5%). After removal of the cerebellum, the brain was glued and coronal slices (150 µm thickness) were cut throughout the septum and preoptic area using a vibratome (VT1200S; Leica). Before recording, slices were incubated at 34° C. for a recovery period of 1 h. After recovery, slices were placed in a submerged recording chamber (32.8° C.; Warner Instruments) and continuously perfused (2 ml/min) with oxygenated ACSF. GFP-positive GnRH neurons in the hypothalamic preoptic area were visually identified with a 40× objective magnification in an upright Leica DM LFSA microscope under a FITC filter and their cell body observed by using IR-differential interference contrast. Whole-cell patch-clamp recordings were performed in current-clamp with bridge mode by using a Multiclamp 700B amplifier (Molecular Devices). Data were filtered at 1 kHz and sampled at 5 kHz with Digidata 1440A interface and pClamp 10 software (Molecular Devices). Pipettes (from borosilicate capillaries; World Precision Instruments) had resistance of 6-8 MS2 when filled with an internal solution containing the following (in mM): 140 K-gluconate, 10 KCl, 1 EGTA, 2 Mg-ATP and 10 HEPES, pH 7.3 with KOH. Bridge balance was adjusted to compensate for pipette resistance. All recordings were analyzed with Clampfit 10 (Molecular Devices). Junction potentials were determined to allow correction of membrane potential values. Electrical membrane properties were measured in current-clamp mode by applying a series of current pulses from −60 to +60 pA (1 s, 10 pA increments). Input resistance ($R_{in}$) was determined by measuring the slope of the linear portion of the current-voltage (I-V) curve. Recordings were terminated if $R_{in}$ changed more than 10% between the beginning and the end of the recording. Membrane capacitance ($C_m$) was calculated using the equation $\tau=RC$, where $\tau=$time constant, R=resistance, and C=capacitance. Membrane time constant was estimated by fitting a single exponential to the charging curve (Clampfit 10; Molecular Devices) generated from a hyperpolarizing current pulse (1 s, 10 pA) from rest.

A.19. Statistical Analysis

All analyses were performed using Prism 7 (Graphpad Software, San Diego, CA) and assessed for normality (Shapiro-Wilk test) and variance, when appropriate. Sample sizes were chosen according to standard practice in the field. The investigators were not blinded to the group allocation during the experiments. However, analyses were performed by two independent investigators in a blinded fashion. For each experiment, replicates are described in the figure legends.

For AMH measurement during pregnancy, as AMH levels were found not to be normally distributed in the study population, results are reported as median and $5^{th}$-$95^{th}$ percentile range. All comparisons between PCOS and control patients were performed using the nonparametric Mann-Whitney U test. The significance level was set at P<0.05. For animal studies, data were compared using an unpaired two-tailed Student's t-test or a one-way ANOVA for multiple comparisons followed by Tukey's multiple comparison post-hoc test. Data analyses for percentages were performed using either a Mann-Whitney U test (comparison between two experimental groups) or Kruskal-Wallis test (comparison between three or more experimental groups) followed by a Dunn's post hoc analysis. The number of biologically independent experiments, sample size, P values, age and sex of the animals are all indicated in the main text or figure legends. All experimental data are indicated as mean±s.e.m or as the 25th-75th percentile, line at median. The significance level was set at P<0.05. Symbols in figures correspond to the following significance levels: * P<0.05,  P<0.001, *P<0.0001.

Example 1

AMH Levels of Pregnant Women Affected or not Affected with PCOS

The comparisons of AMH serum concentrations in 63 control women (age 27-39 years old) and 66 women with PCOS (age 27-39 years old) at gestational week 16-19 (Table 1) revealed significant differences in median AMH values between these populations, with AMH concentrations being higher in pregnant PCOS women than in control women (FIG. 1A). This difference was not attributable to differences in age between the two groups (Table 1).

TABLE 1 demographic data of pregnant control and PCOS patients

|  | Control lean (N = 30) | PCOS lean (N = 32) | Control obese (N = 33) | PCOS obese (N = 34) | P value |
|---|---|---|---|---|---|
| Ethnic group | Caucasian (N = 30) | Caucasian (N = 32) | Caucasian (N = 33) | Caucasian (N = 34) | nd |
| Gestational age (weeks) | 16-19 | 16-19 | 16-19 | 16-19 | nd |
| Age (years) of pregnant patients | 32 (QR 28.75-32.25) | 31.5 (QR 29.25-35.00) | 32 (QR 29.5-36.00) | 33 (QR 30.75-37.00) | 0.5241 |
| BMI in first trimester (Kg/m$^2$) | 22.4$^a$ (IQR 20.42-23.44) | 21.91$^a$ (IQR 20.56-23.17) | 32.47$^b$ (IQR 30.62-33.89) | 32.37$^b$ (IQR 29.82-34.29) | a vs b < 0.0001 |
| Gestational length (days) | 280 (IQR 272-286) | 278 (IQR 270.3-289) | 282 (IQR 273.5-289) | 279 (IQR 269.8-287) | 0.7225 |
| Bitrthweight (g) | 3675 (IQR 3300-3900) | 3510 (IQR 3210-3778) | 3620 (IQR 3285-4125) | 3670 (IQR 3255-4175) | 0.3536 |
| IVF | 3 out of 31 | 10 out of 32 | 0 out of 33 | 5 out of 34 | nd |

For Table 1 above, blood samples were derived from the population-based Uppsala Biobank of Pregnant Women, where blood samples are collected in conjunction with the routine ultrasound screening in gestational week 16-19.

When applicable, the Kruskal-Wallis test followed by Dunn's post hoc analysis was used to analyze differences between study groups. The significance level was set at P<0.05 (Table 1).

Abbreviations: IQR, Interquartile ranges; BMI, body mass index; IVF, in vitro fertilization (Table 1).

Figure 1B:
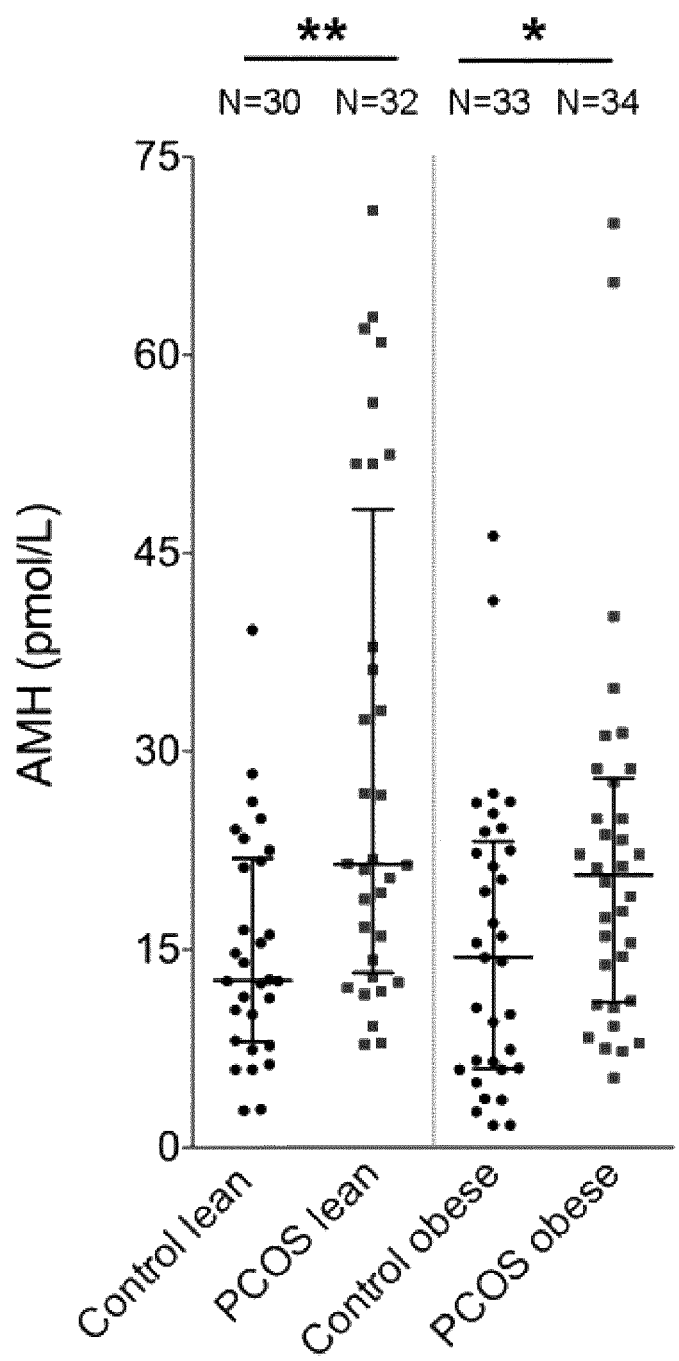

When we analysed this sample stratified by body mass index (BMI), and classified women as lean or obese (lean BMI 25 kg/m$^2$, obese BMI>30 kg/m$^2$), we found that AMH was still significantly higher in women with PCOS as compared to the control group, regardless of BMI, even though the difference was more striking in the lean women than in the obese (FIG. 1B).

Figure 1C:
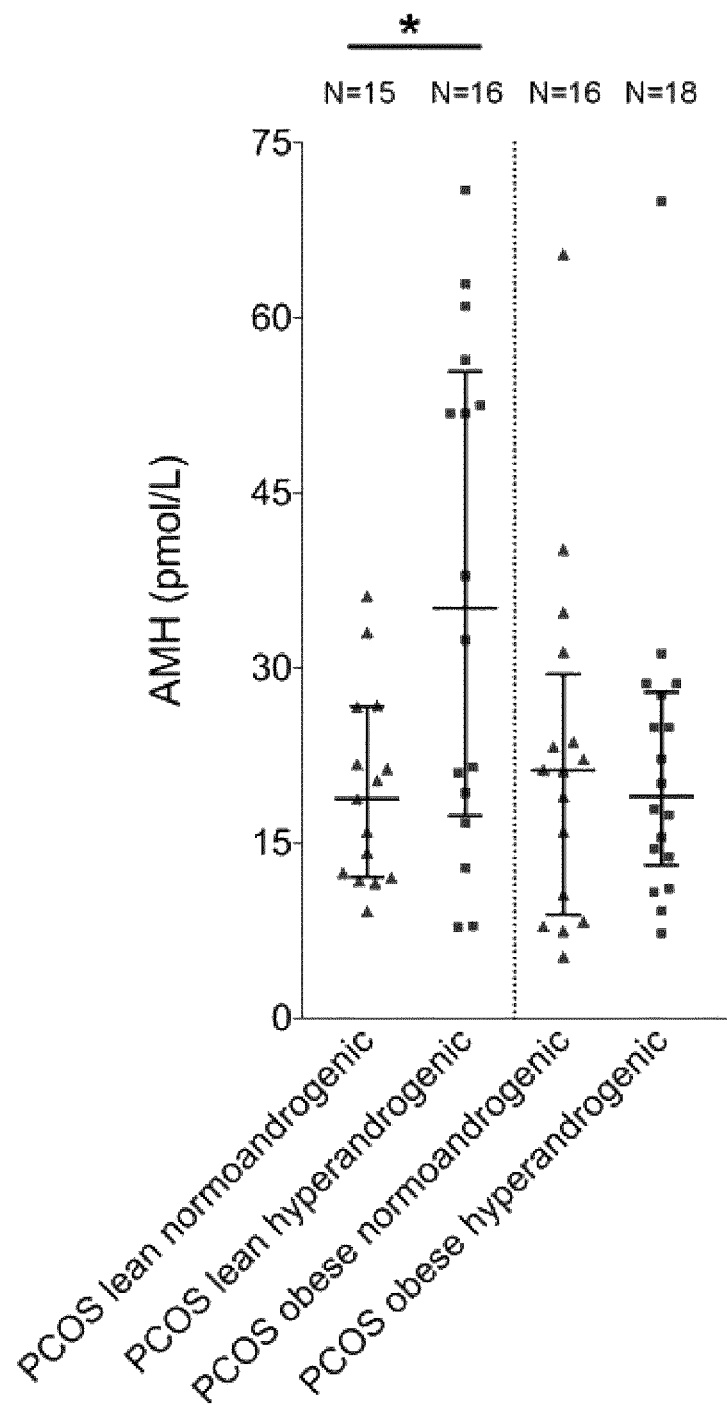

Interestingly, when we compared women with PCOS, stratified by BMI as well as hyperandrogenism (normoandrogenic vs. hyperandrogenic, the latter defined as either biochemical or clinical hyperandrogenism), we detected a significant difference between lean normo- and hyperandrogenic women with PCOS, with AMH being more elevated in hyperandrogenic lean PCOS women than in normoandrogenic lean women (FIG. 1C).

No difference between normo- and hyperandrogenic obese women with PCOS was detected (FIG. 1C).

Figure 1D:
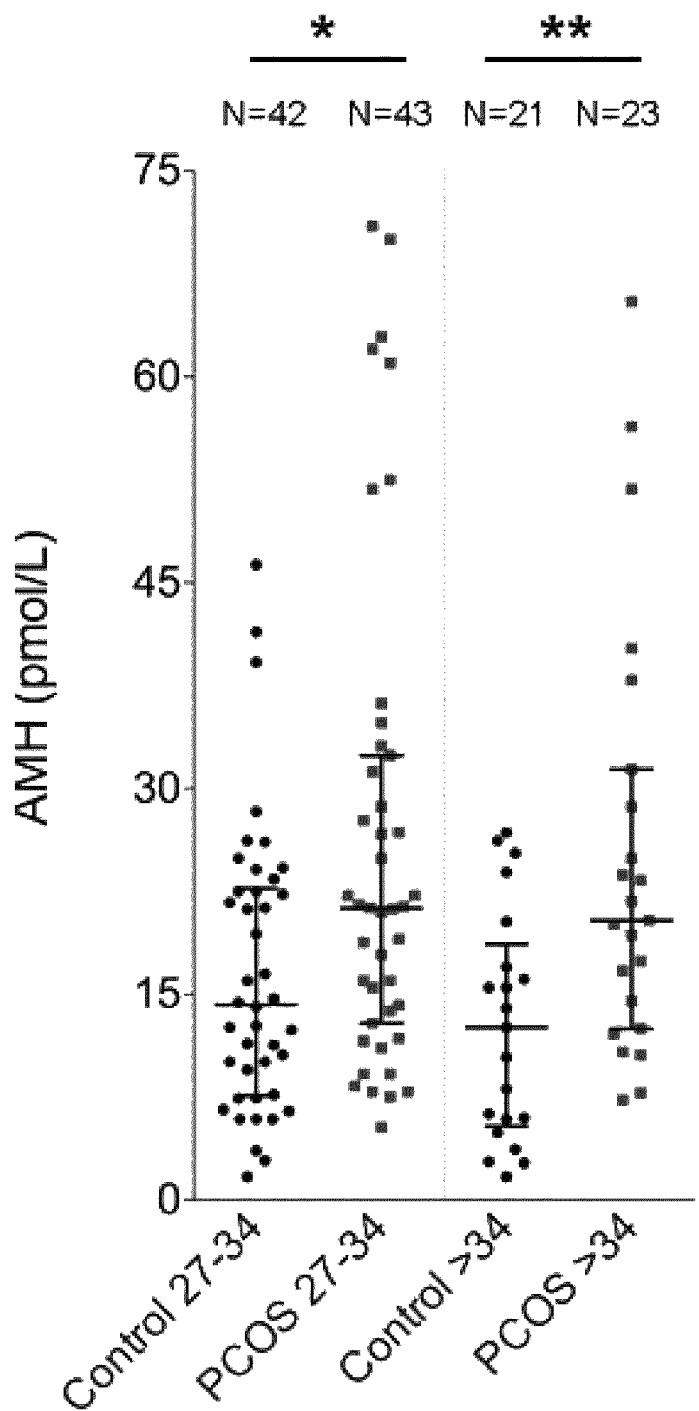

We then analysed the control and PCOS groups stratified by age (age 27-34 years and age >34 years), and found higher AMH levels in both PCOS age groups compared with their respective control women (FIG. 1D).

Our results show that serum AMH levels are higher in PCOS pregnant women than in control women, regardless of their age and BMI.

Example 2

Animal Model of PCOS

Figure 2A:
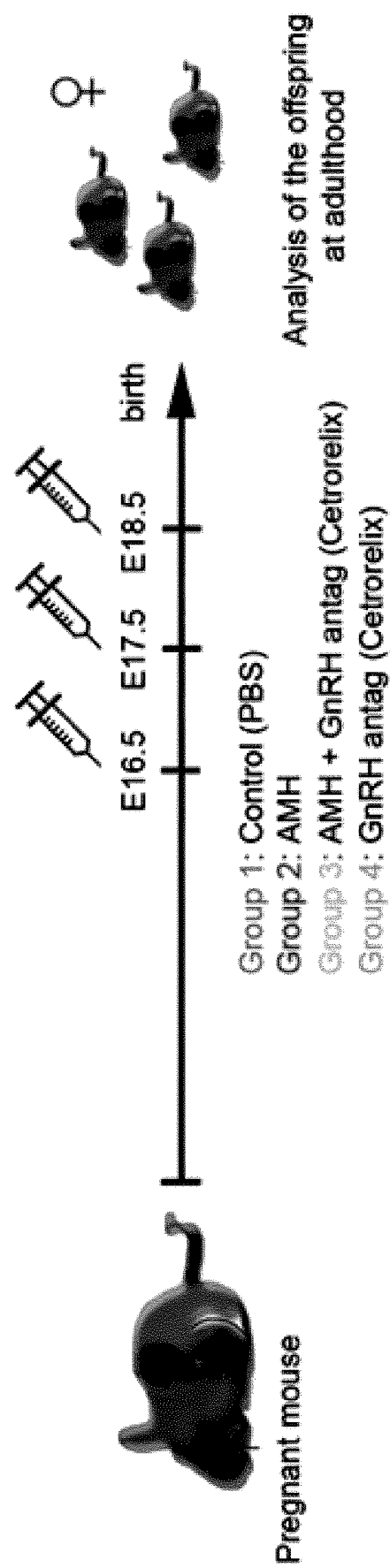

In order to test whether prenatal exposure to AMH might lead to hyperandrogenism and PCOS later in life, we treated pregnant female mice with vehicle (PBS) or recombinant human AMH at the end of their gestation and studied the neuroendocrine reproductive features of the female offspring postnatally (FIG. 2A).

Figure 2B:
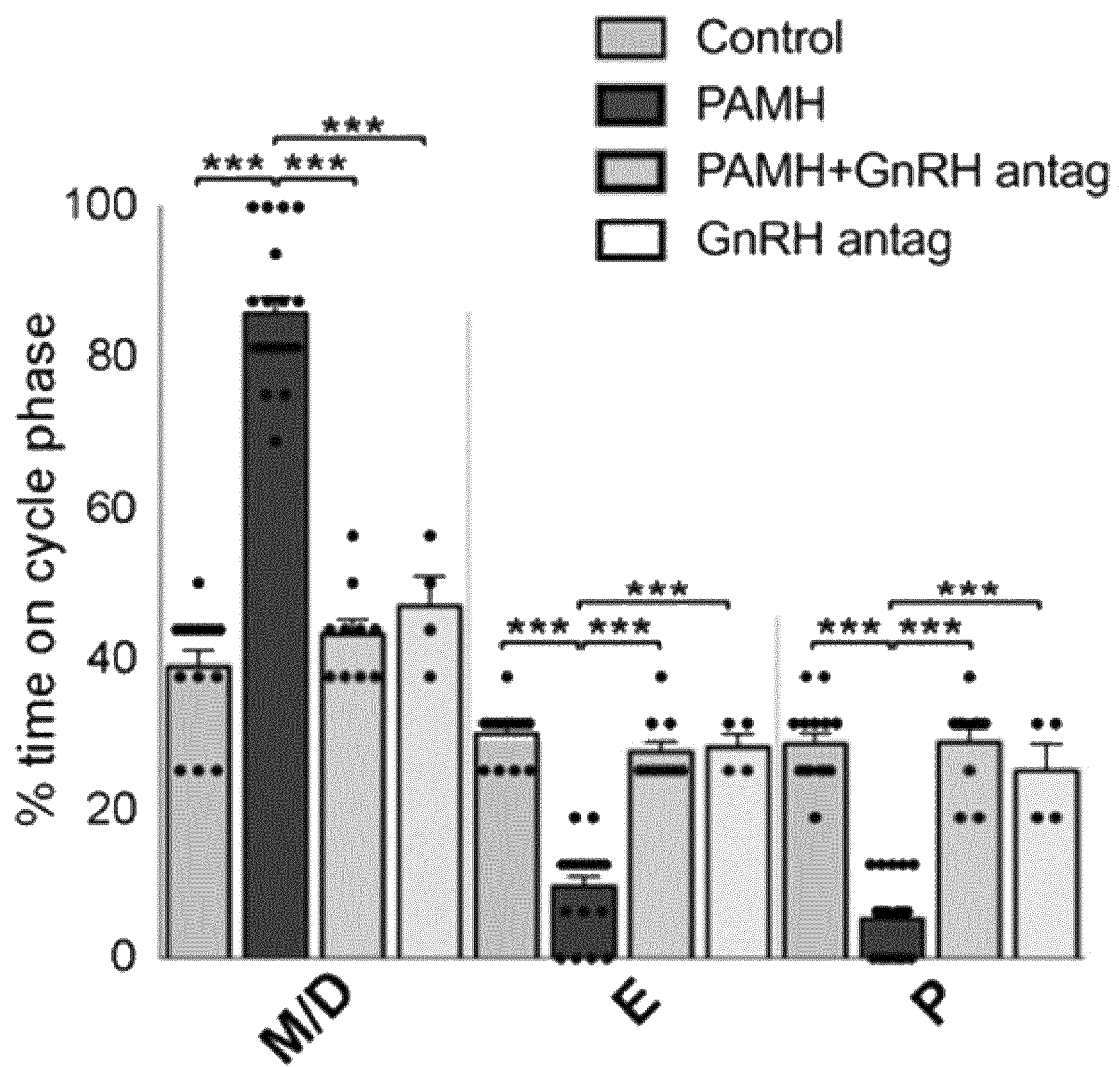
Figure 8A:
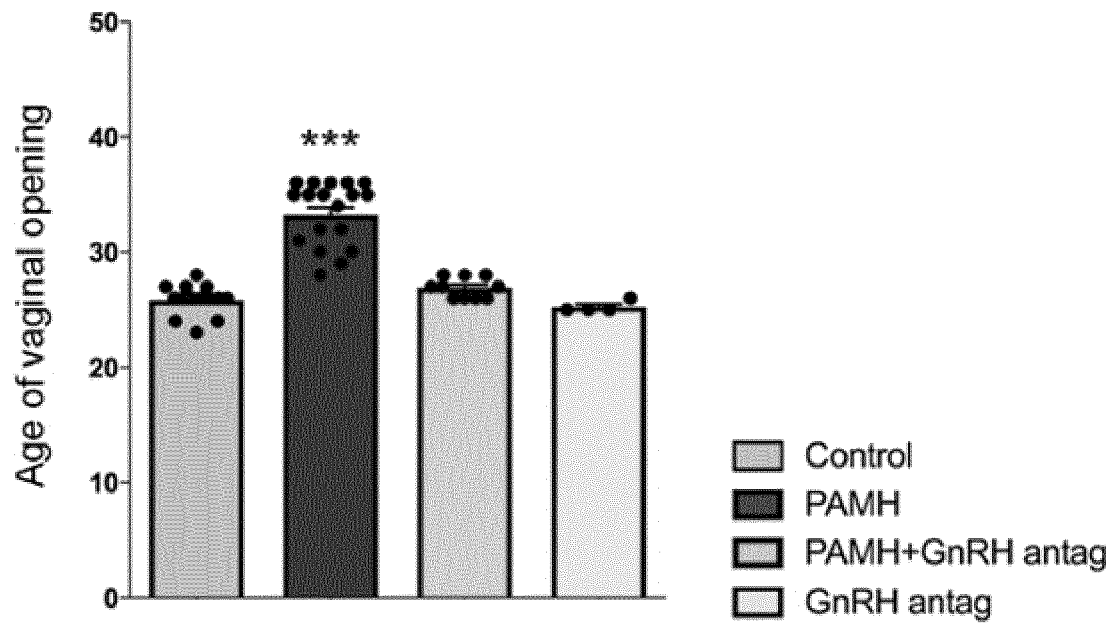
Figure 8B:
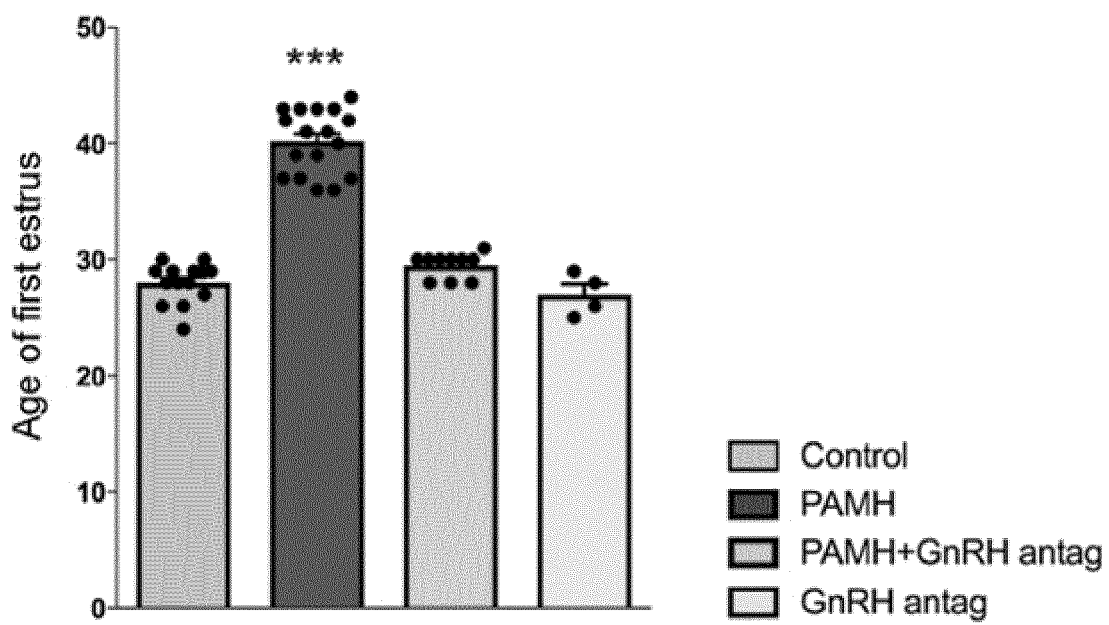
Figure 8C:
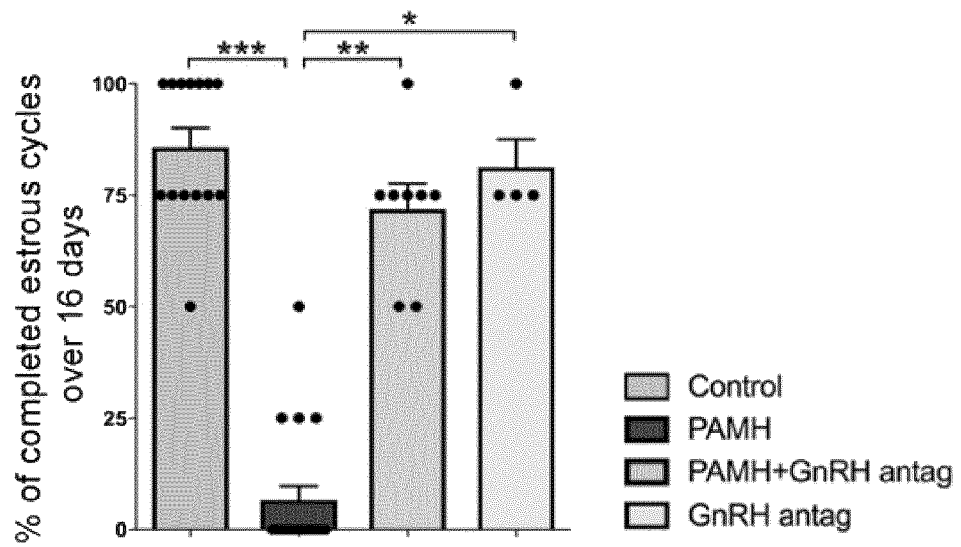
Figure 8D:
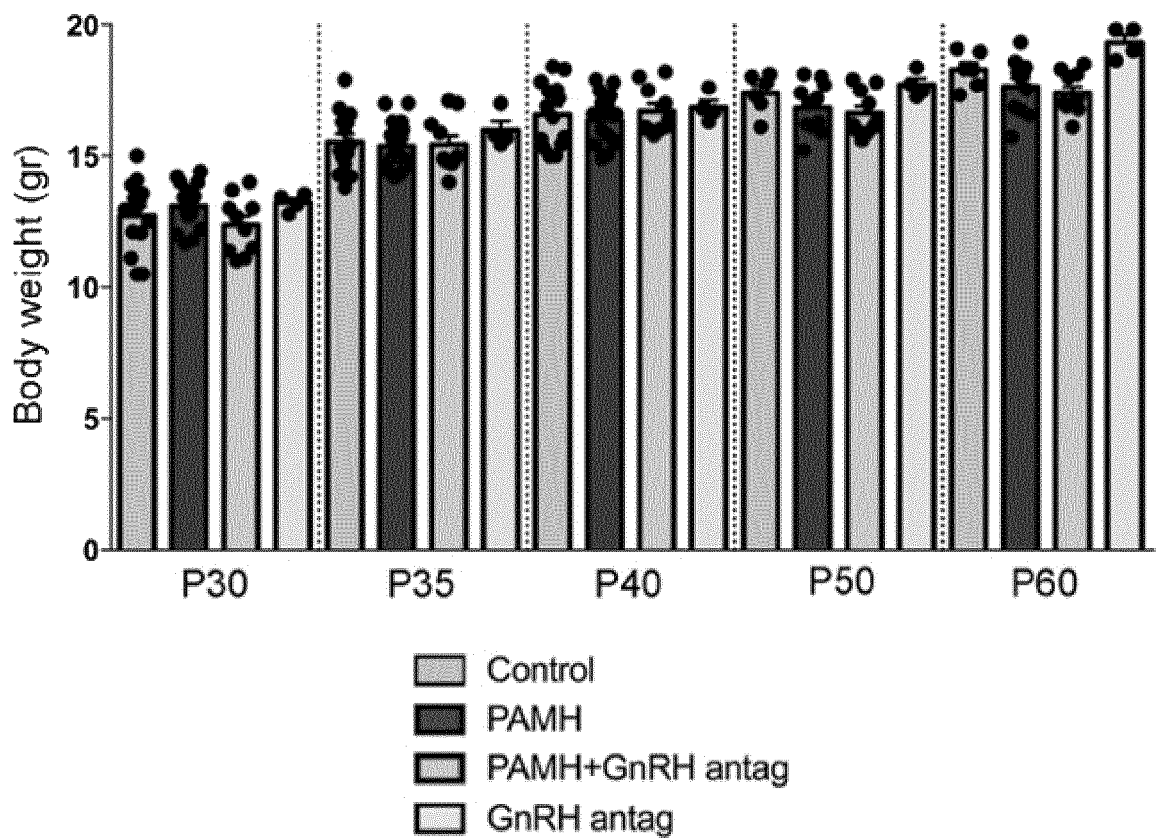

We injected i.p. pregnant mice daily with PBS (Control) or recombinant AMH (0.12 mg/Kg/d; prenatal AMH treated: PAMH) (Cimino, et al. 2016, Nature communications Vol. 7, 10055). during the same temporal window that was previously used to generate PNA mice (E16.5-E18.5) (Sullivan et al., 2004, Proceedings of the National Academy of Sciences of the United States of America Vol. 101, 7129-7134; Moore et al., 2013, Endocrinology Vol. 154, 796-806; Moore et al., 2015, Proceedings of the National Academy of Sciences of the United States of America Vol. 112, 596-601) (FIG. 2A). We chose this temporal window for the treatment because it lies beyond the developmental stages during which gonadal sexual differentiation has been reported to occur in mice (E12.5-E14.5) and to thereby exclude any damaging effects that exogenous AMH might have on Müllerian duct regression (Orvis et al., 2007, Developmental biology 306, 493-504). Similar to what was observed in the PNA mice (Moore et al., 2013, Endocrinology Vol. 154, 796-806; Moore et al., 2015, Proceedings of the National Academy of Sciences of the United States of America Vol. 112, 596-601), the PAMH-treated animals exhibited delayed vaginal opening, delayed puberty onset (FIG. 8A, 8B), severely disrupted estrous cyclicity (oligo-anovulation; FIG. 8C and FIGS. 2B, 2C-1, 2C-2, 2C-3) and no difference in body weight (FIG. 8D). Our results show that PAMH mice rarely entered the proestrus and estrus phase of the cycle and displayed a prolonged diestrus as compared to the PBS-treated female offspring (Control) (FIG. 2B). Prenatal GnRH antagonist treatment prevented the appearance of the ovulatory and fertility defects in postnatal offspring (PAMH+GnRH antag; FIG. 2B, 2D-1, 2D-2, 2D-3, 2E). Ovarian histology of PAMH animals showed abnormalities consistent with their anovulatory phenotype, with the presence of fewer post-ovulation corpora lutea, less mature antral follicles and a greater number of atretic follicles as compared to control animals (FIG. 2D-1, 2D-2, 2D-3). Additionally, PAMH adult female mice showed impaired fertility and displayed a significant delay in their first litter, produced fewer litters and fewer pups per litter over a 3-month period compared with controls (FIG. 2E-1, 2E-2, 2E-3).

In order to test whether prenatal AMH treatment leads to the disruption of the neuroendocrine reproductive axis in the offspring in a GnRH-dependent manner, we then treated pregnant mice with AMH together with a GnRH antagonist (Cetrorelix acetate; 0.5 mg/Kg)(Cimino, I., et al, 2016, Vpl. 7, 10055 (2016). Interestingly, the oligo-anovulation and subfertility of PAMH mice was totally prevented by the prenatal co-administration of AMH with the GnRH antagonist, whereas GnRH antagonist treatment alone had no effect on both estrous cyclicity and fertility (FIG. 2B, 2C, 2E-1, 2E-2, 2E-3).

Figures 1, 2C:
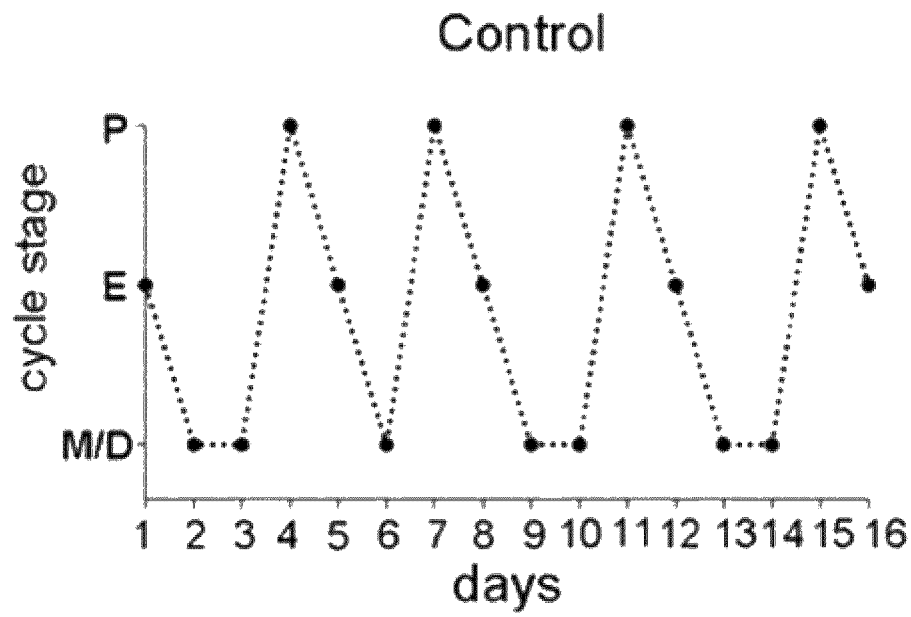
Figures 2, 2C:
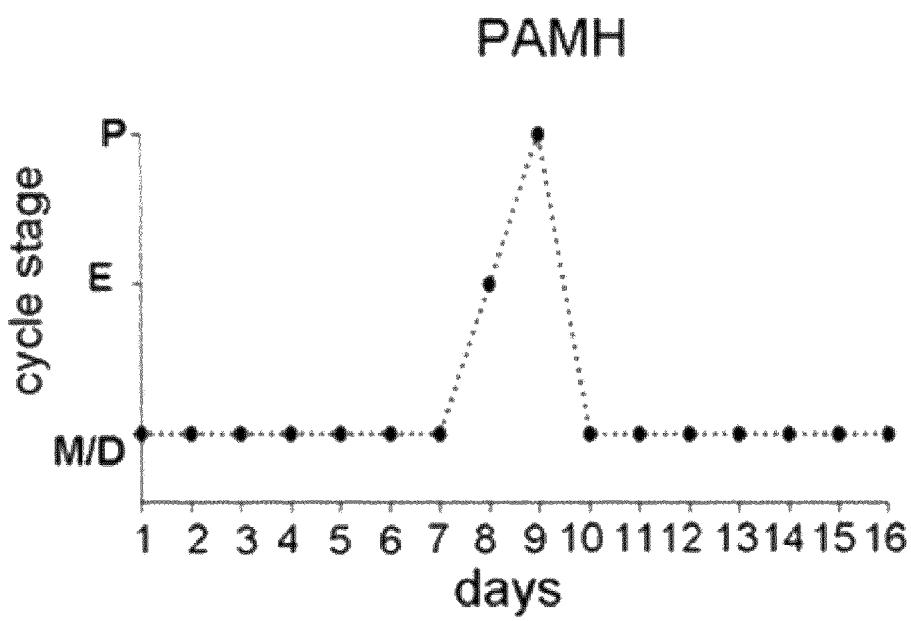
Figures 2, 2C, 3:
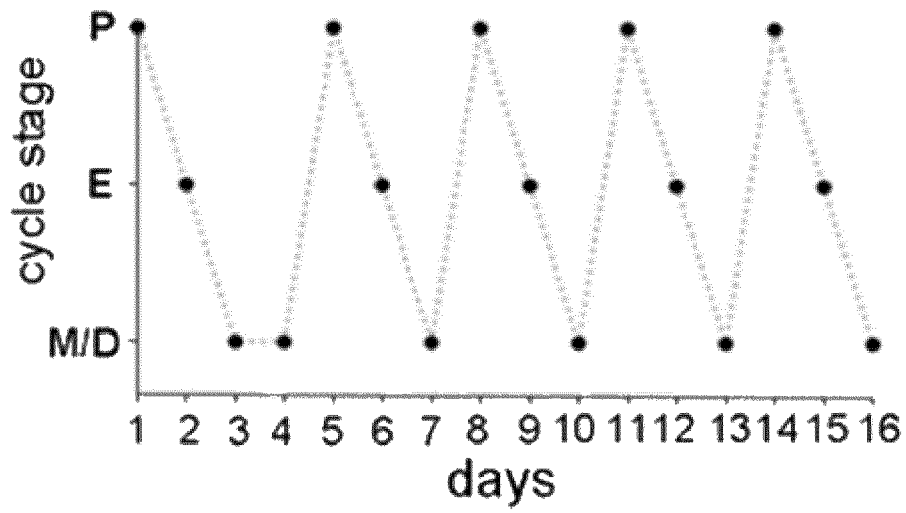
Figures 2, 2C, 3, 4:
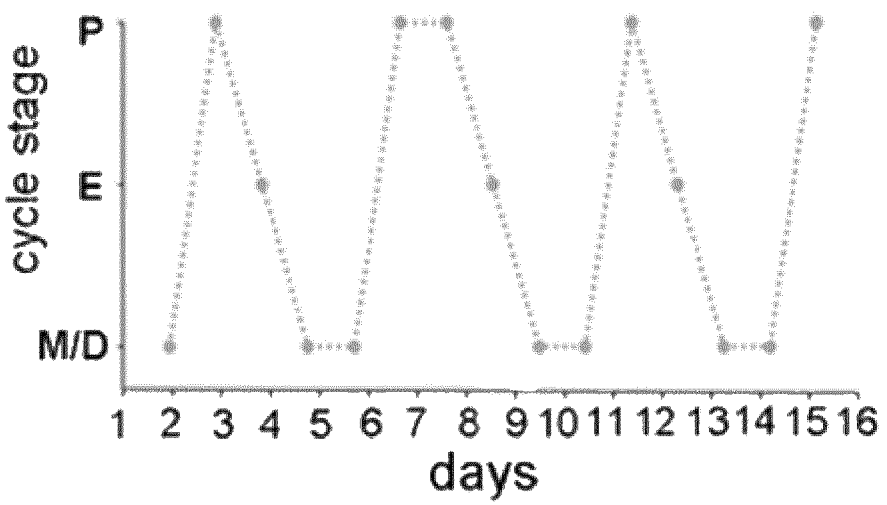
Figures 1, 2D:
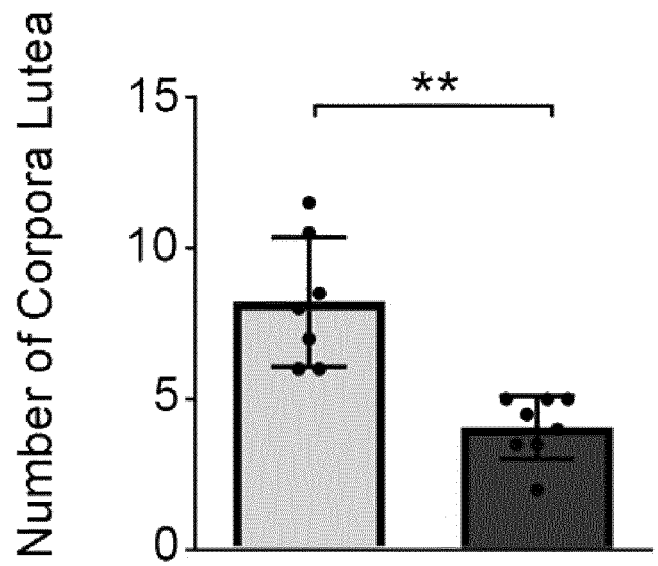
Figure 2:
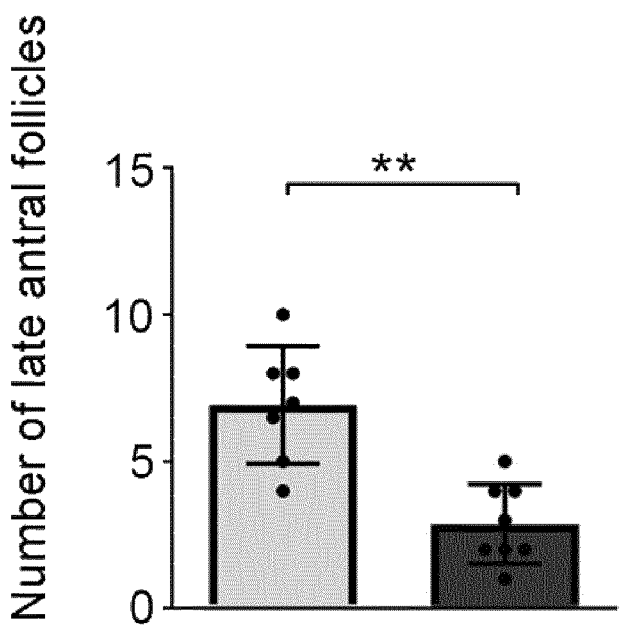
Figure 2:
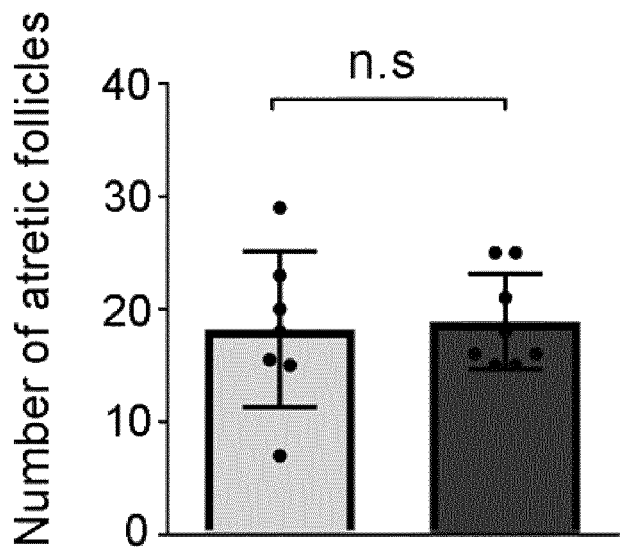
Figures 1, 2E:
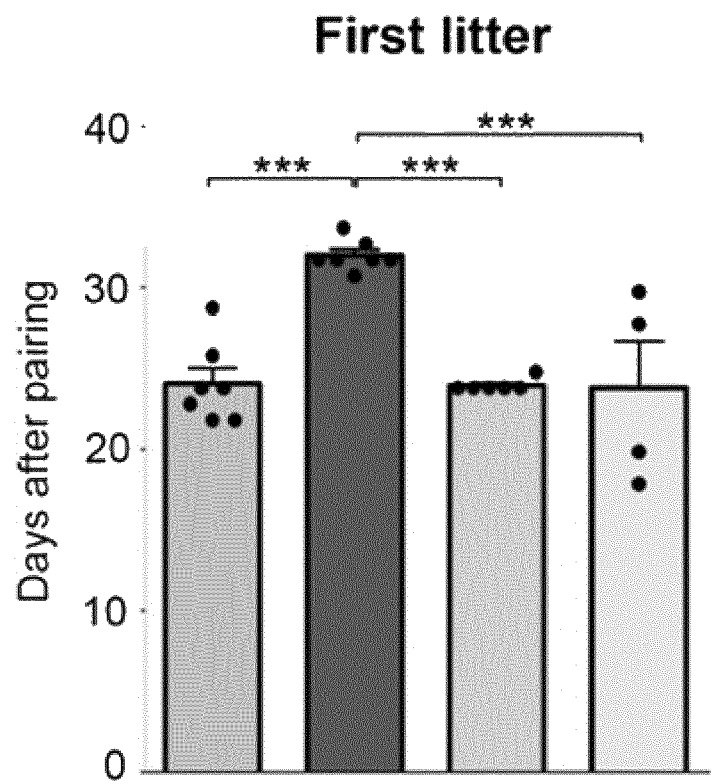
Figures 2, 2E:
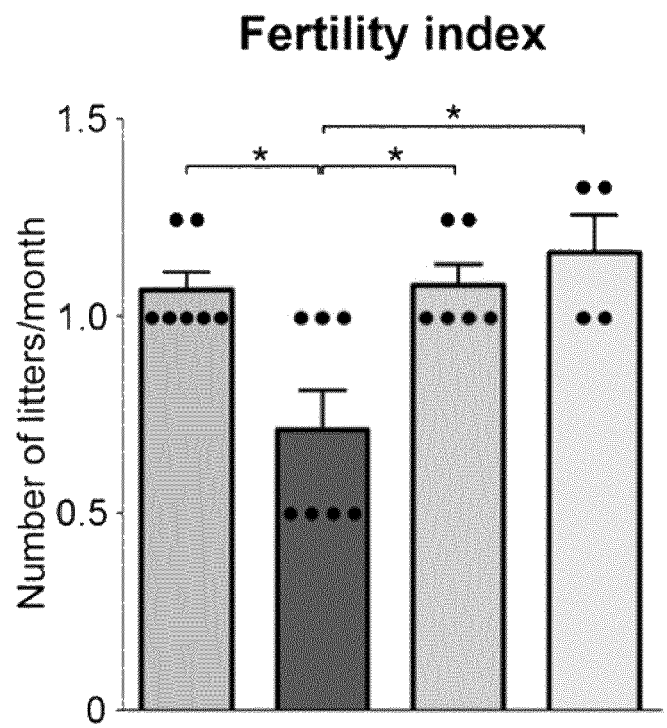
Figures 2, 2E, 3:
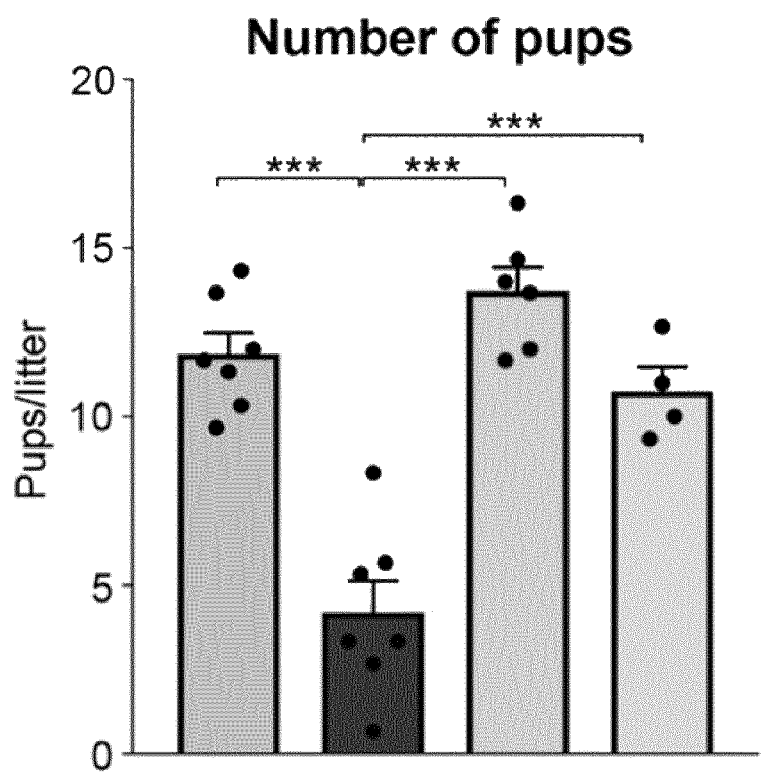
Figure 3A:
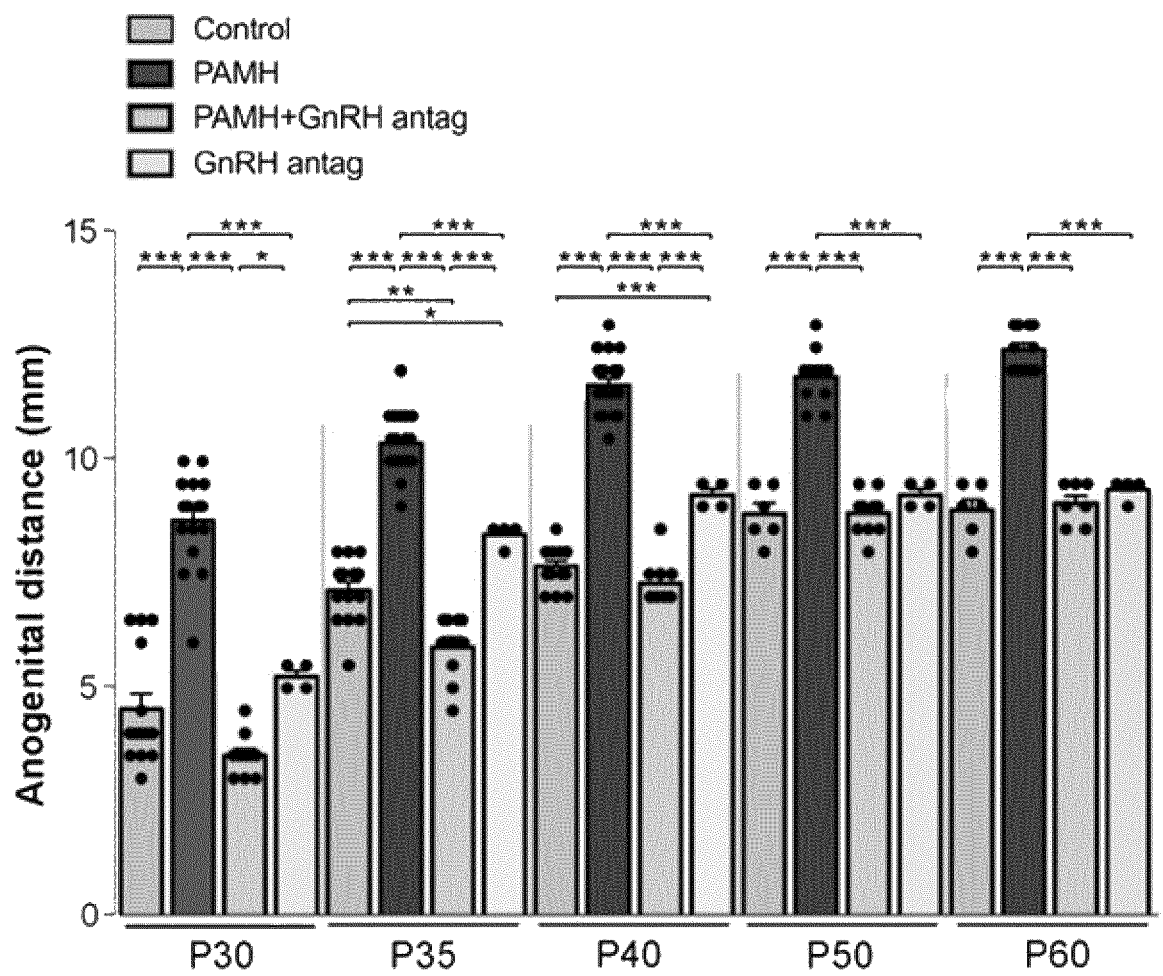
Figure 3B:
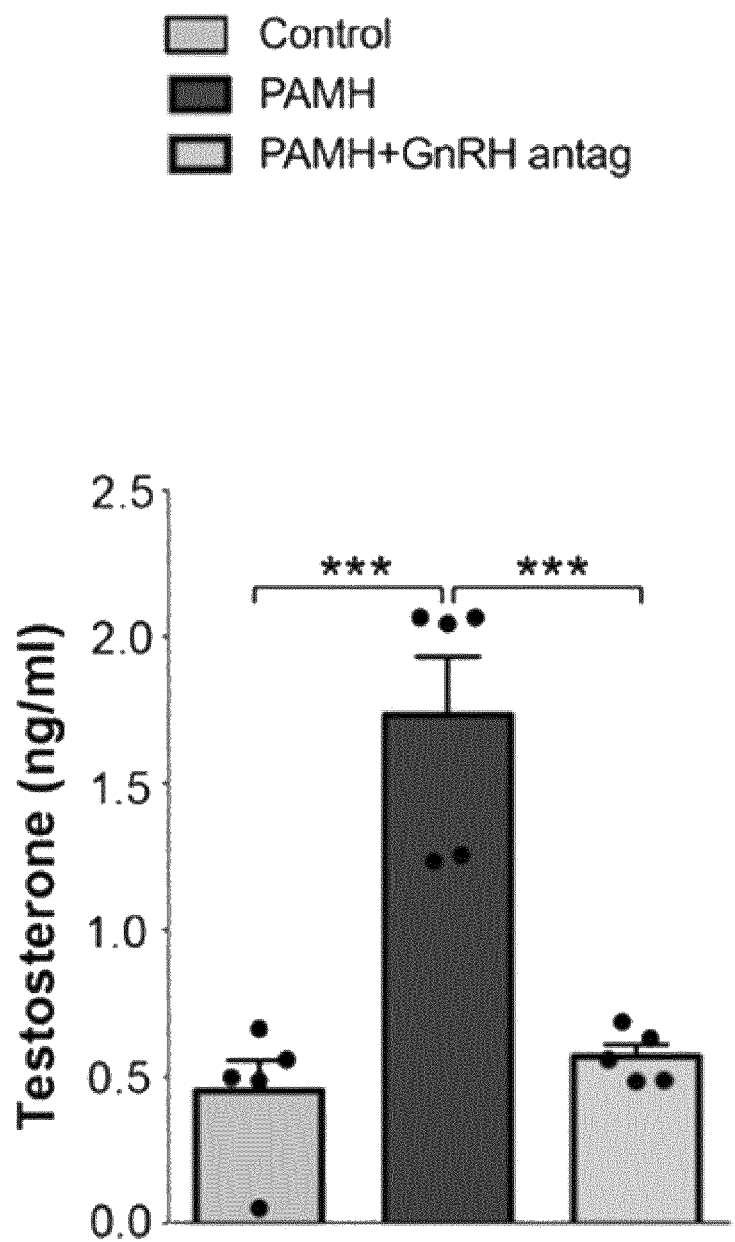
Figure 3C:
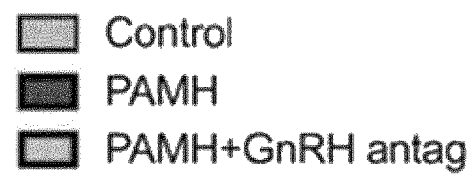
Figure 3C:
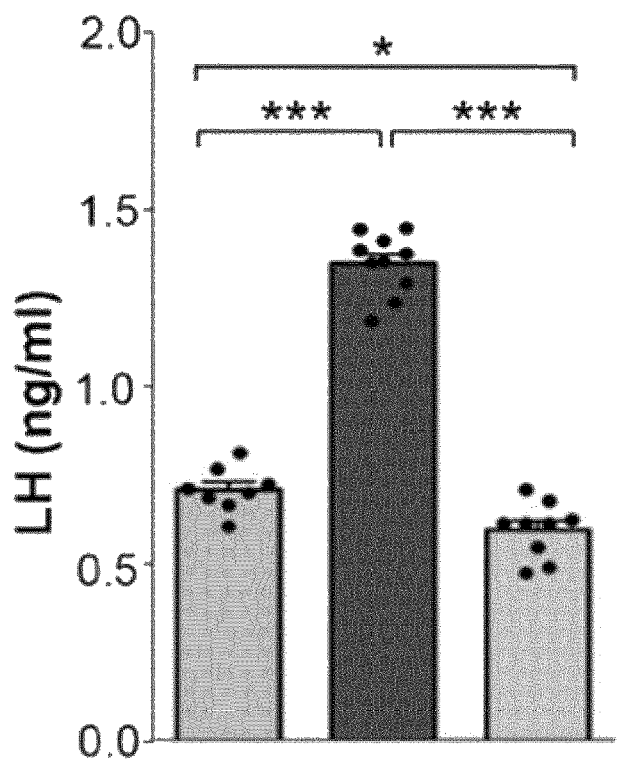
Figure 3D:
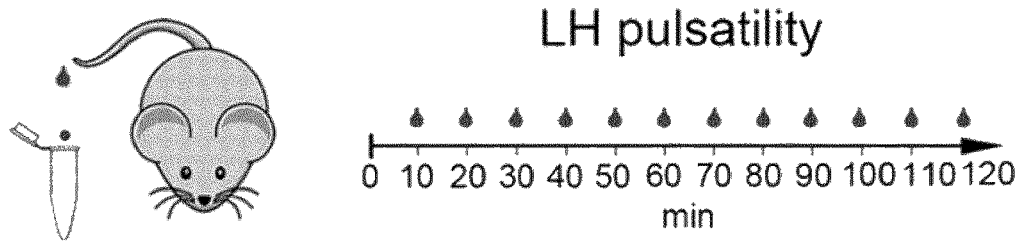
Figure 3E:
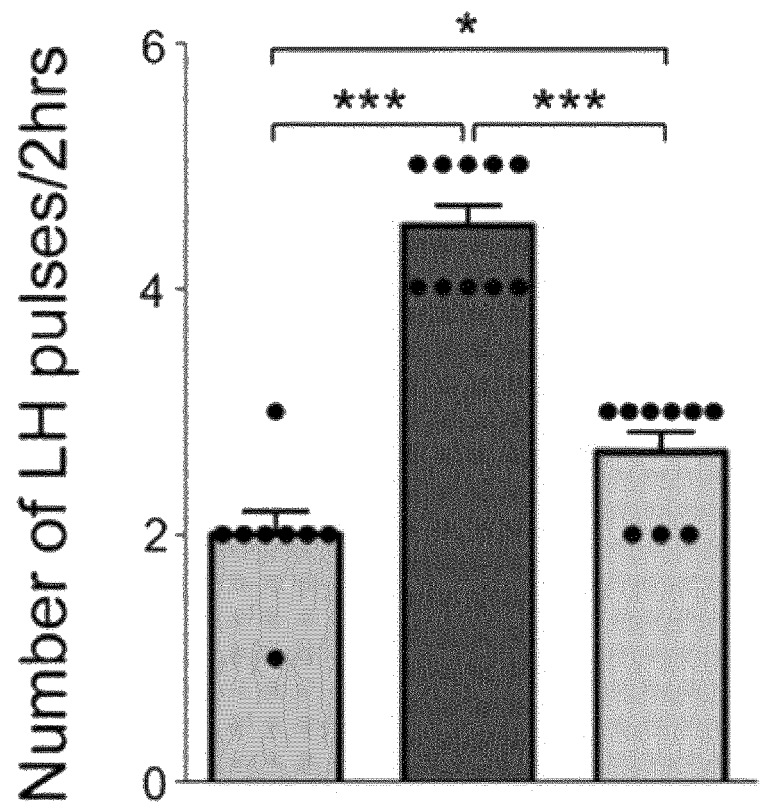
Figures 1, 3F:
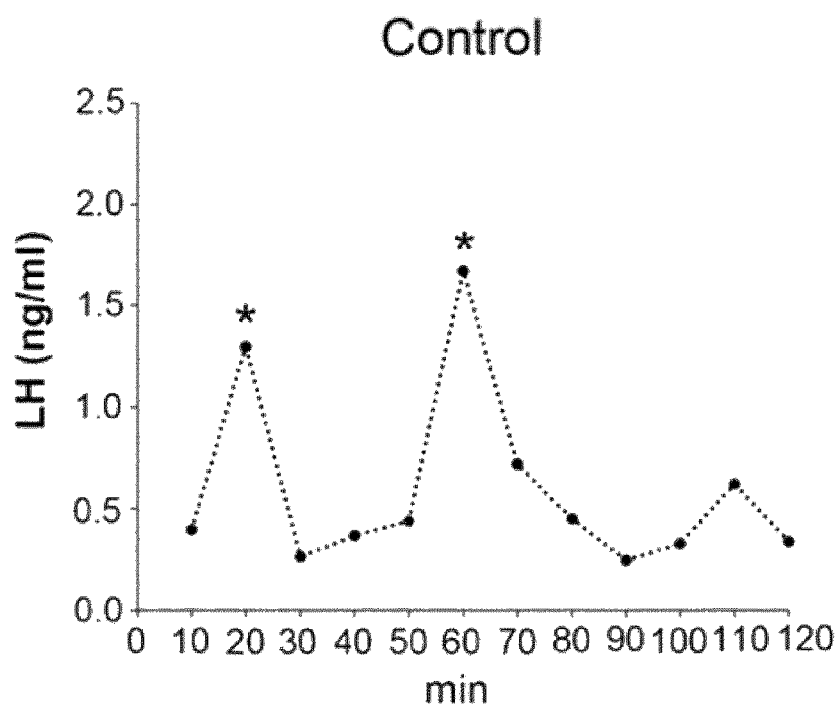
Figures 2, 3F:
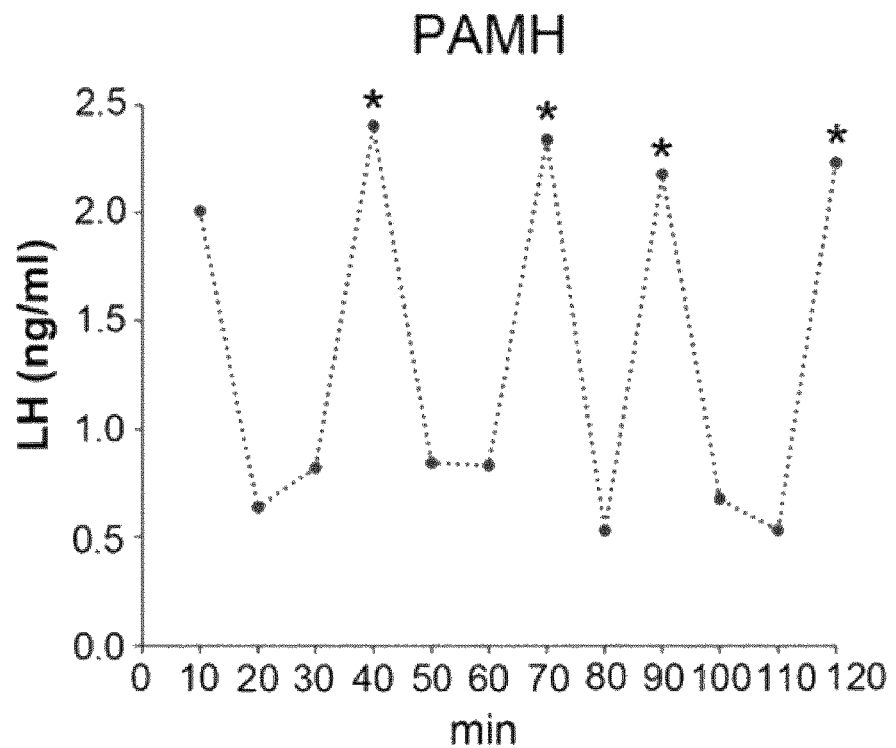
Figures 3, 3F:
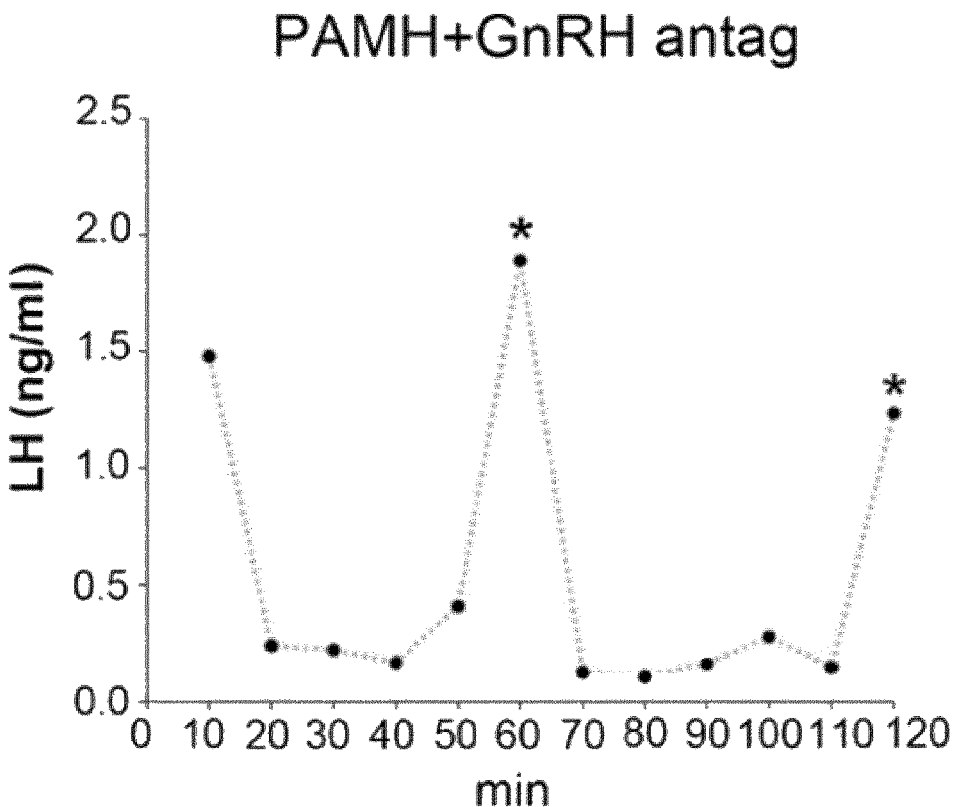

As described above, the increased production of ovarian androgen is the major hallmark of PCOS. In order to determine whether prenatal AMH treatment affected the levels of circulating testosterone in PAMH animals postnatally, we first measured the ano-genital (ano-vaginal) distance, which is directly regulated by testosterone, from postnatal day 30 (P30) to P60 (FIG. 3A). Our results showed that the PAMH female offspring showed a significantly longer ano-genital distance than did the control female offspring (FIG. 3A). Importantly, also this phenotype was completely rescued by the GnRH antagonist treatment (FIG. 3A). We next measured plasma testosterone and LH levels during diestrus in Control, PAMH and PAMH+GnRH antagonist mice and showed that PAMH offspring had significantly elevated testosterone and LH compared with the other two groups (FIG. 3B, 3C). Most women who are diagnosed with PCOS exhibit accelerated LH secretion, which is suggestive of rapid GnRH release (Ehrmann et al., 2005, The New England journal of medicine Vol. 352, 1223-1236; Goodarzi et al., 2011,. Nature reviews. Endocrinology Vol. 7, 219-231). This is particularly the case for the metabolically healthy PCOS women (lean subjects and normal insulin levels) in which a high LH level (≥15 mIU/ml) was found in 95% of these patients (Huang, C. C., et al. , 2015, Human reproduction Vol. 30, 937-946). We measured LH pulses in serial blood samples from gonadally intact mice during diestrus (FIG. 3D). PAMH animals had significantly increased LH pulse frequency as compared to control and AMH+GnRH antagonist treatment groups (FIG. 3E, 3F-1, 3F-2, 3F-3).

Altogether these data show that the PAMH mouse model, like the PNA ones (Sullivan et al., 2004, Proceedings of the National Academy of Sciences of the United States of America Vol. 101, 7129-7134, Moore et al., 2013, Endocrinology Vol. 154, 796-806; Witham et al., 2012, Endocrinology Vol. 153, 4522-4532) recapitulated the majority of PCOS reproductive deficits and cardinal neuroendocrine features seen in the clinic, including hyperandrogenism, disrupted estrous cyclicity, and modified ovarian morphology but did not present major metabolic disturbances, indicating that this preclinical model is most representative of the "lean" PCOS phenotype.

Strikingly, our results also show that prenatal GnRH antagonist treatment prevents the transgenerational transmission of the disease, supporting a critical role for GnRH in the neuroendocrine dysfunctions of PCOS.

Circulating AMH is presumed to be a mixture of proprotein (proAMH) and a complex of the NH2- and COOH-terminal peptides ($AMH_{N,C}$), that can bind to AMHR2 and initiate signalling. We thus sought to investigate whether prenatal exposure to proAMH would recapitulate the same PCOS-like traits observed upon injection of the bioactive form of AMH ($AMH_C$).

We injected pregnant mice daily with PBS (Control) or with the proAMH (AMH, 0.12 mg/Kg/d) from E16.5 to E18.5 and studied the neuroendocrine phenotype of the offspring postnatally. The prenatal proAMH-treated offspring (PproAMH), like the prenatal AMHc-treated offspring ($PAMH_C$) animals, exhibited delayed vaginal opening (VO), delayed puberty onset, disrupted estrous cyclicity and no difference in body weight in adulthood. The PproAMH offspring displayed significantly longer ano-genital distance, increased circulating T and LH levels as compared to controls. Moreover, PproAMH females exhibited constitutively high LH pulsatility. These data indicate that prenatal injections of proAMH mirrors the same PCOS neuroendocrine features observed in PAMH mice.

Since LH secretion is an indirect measurement of GnRH neuronal secretion, we measured LH in pregnant mice one day after vehicle (PBS), AMH or AMH+GnRH antagonist treatment (E19.5; FIG. 3I-1, 3I-2, 3I-3, 3I-4). During pregnancy serum LH levels are known to be almost undetectable as a consequence of the progesterone break. Unexpectedly, circulating LH levels were found to be 5 times higher in AMH-treated pregnant mice as compared to the control group (FIG. 3I-1, 3I-2, 3I-3, 3I-4). Such increase was prevented by the prenatal co-treatment of AMH with the GnRH antagonist (FIG. 3I-1, 3I-2, 3I-3, 3I-4). To assess whether the rise in LH levels would also be associated with an elevation in circulating T, caused by GnRH-driven maternal pituitary hypersecretion of LH driving ovarian testosterone synthesis, we then measured circulating T levels in the three animal groups (FIG. 3I-1, 3I-2, 3I-3, 3I-4). AMH-treated pregnant females showed a robust elevation in T, whereas control and AMH+GnRH antag dams displayed very low T levels (FIG. 3I-1, 3I-2, 3I-3, 3I-4). We next measured circulating estradiol (E2) and progesterone (P) in those treatment groups and found a robust decrease of both hormones in the AMH-treated dams as compared to the vehicle-treated and AMH+GnRH antag-treated dams (FIG. 3I-1, 3I-2, 3I-3, 3I-4). These data indicate that late gestational exposure to high AMH is sufficient to generate in dams heightened LH and T levels and diminished E2 and P concentrations in a GnRH-dependent manner.

Since the placenta expresses AMHR2 both in humans [27] and in mice (FIG. 3h) and high T and low E2 levels were found in AMH-treated dams (FIG. 3I-1, 3I-2, 3I-3, 3I-4), we examined if AMH treatment could alter aromatase expression in the murine placenta, possibly affecting the conversion of T into E2. We performed qPCR for the enzyme P450 aromatase (CYP19A1) gene in the placentae harvested from pregnant mice at the end of the treatment period (FIG. 3J-1, 3J-2, 3J-3, 3J-4). AMH treatment significantly lowered placental aromatase expression (FIG. 3J-1, 3J-2, 3J-3, 3J-4). Intriguingly, GnRH antag treatment prevented the AMH-driven inhibition of CYP19A1 mRNA (FIG. 3J-1, 3J-2, 3J-3, 3J-4). We thus investigated the expression of GnRH, GnRH receptor (GnRHR) and LH receptor (LHR) transcripts in the placentae collected from those animals (Supplementary FIG. 4). All genes were found to be expressed in the placenta of the different treatment groups. However, while the expression of GnRH and GnRHR was unchanged among treatment groups, LHR expression was found to be significantly higher in the AMH-treated dams and to be normalized by the GnRH antag. We next quantified placental expression of CYP11A1 and HSD3B1, two other key steroidogenic enzymes involved in onset of steroidogenesis and derivation of progesterone, respectively. We did not find any difference in the expression of CYP11A1 among treatment groups but we found greatly diminished HSD3B1 expression in the placentae of AMH-treated- versus control dams (FIG. 3J-1, 3J-2, 3J-3, 3J-4). In addition, GnRH antag-treatment prevented the downregulation of HSD3B1 gene expression, indicating normalization of the GnRH/LH-driven maternal steroidogenesis.

Figure 9A:
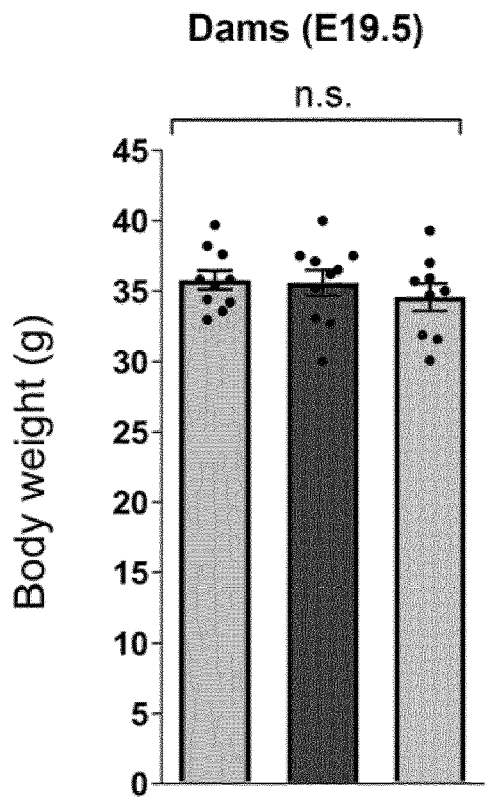
Figure 9B:
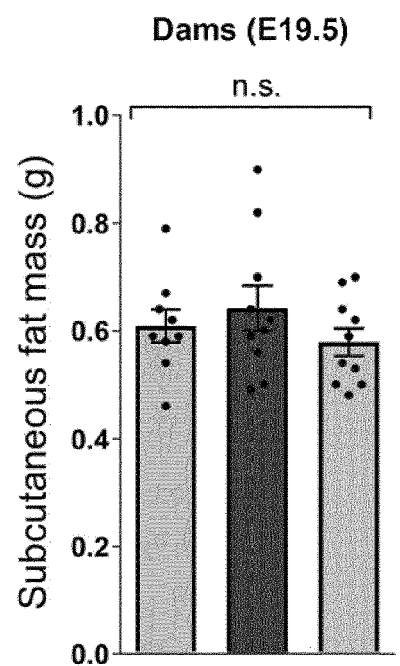
Figure 9C:
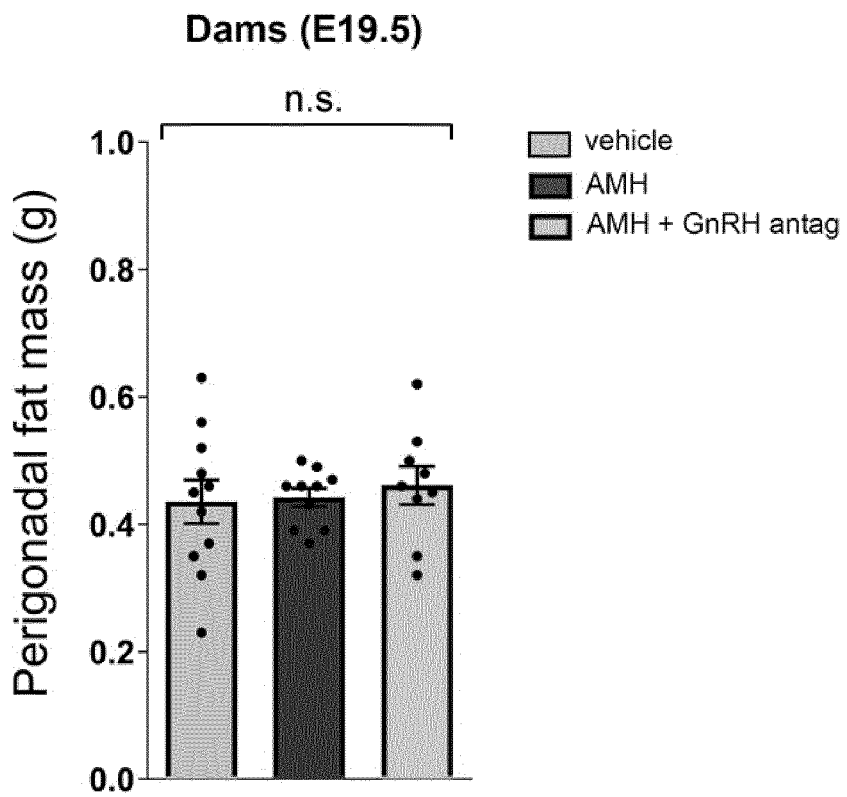

As T is an anabolic hormone, we monitored whether dams increased their body weight and fat deposition as a consequence of the AMH treatment (FIGS. 9A, 9B, 9C). We did not find any changes in body weight, subcutaneous fat mass or perigonadal fat mass in E19.5 dams injected for 3 days with vehicle, AMH or AMH+GnRH antag (FIGS. 9A, 9B, 9C).

Figure 9D:
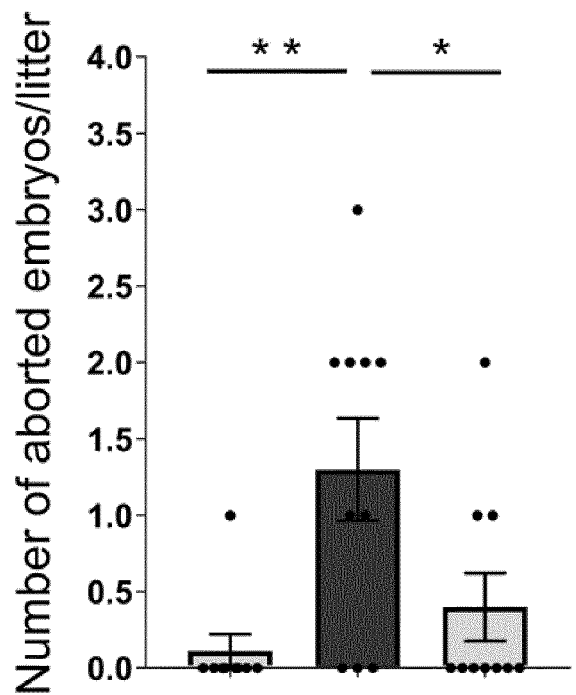
Figure 9E:
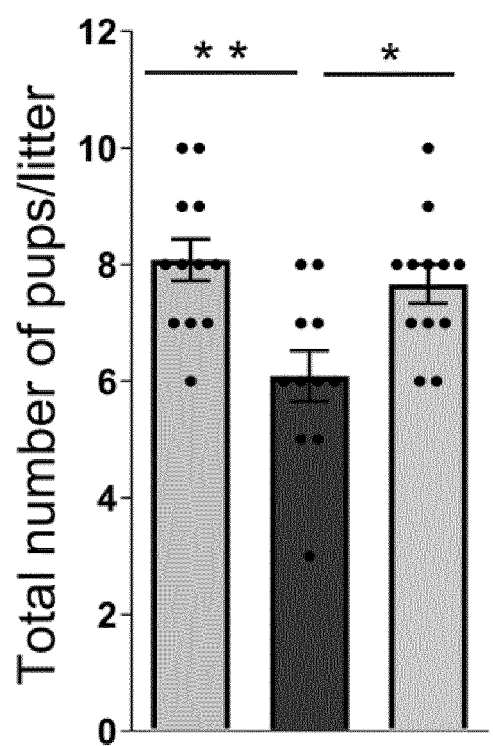
Figure 9F:
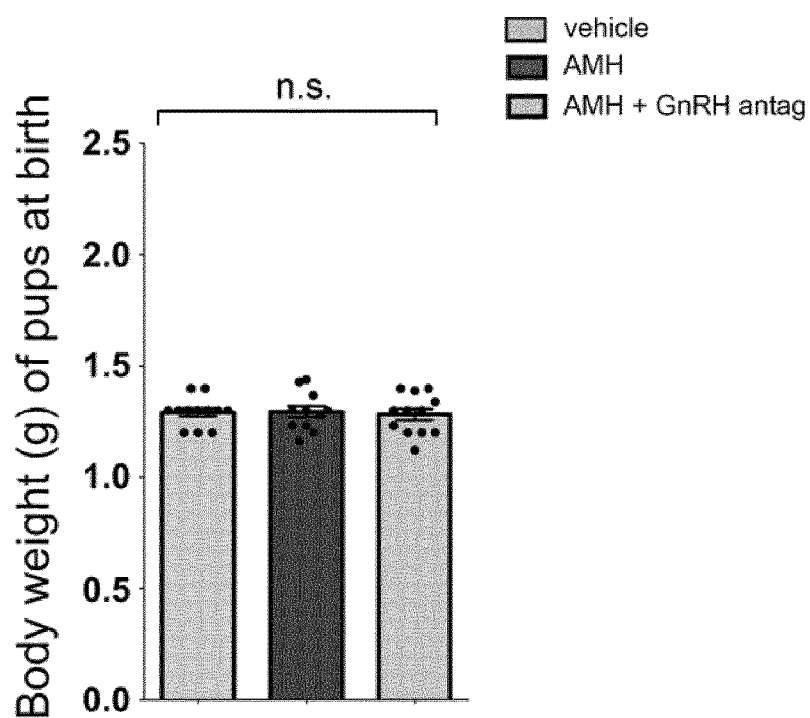

Finally, since P and E2 are vital to placental sufficiency and both hormones were greatly diminished in AMH-treated dams, we monitored whether there were any changes in litters lost, litter size, birthweights of pups when dams experienced diminished placental aromatase and HSD3B1 expression (FIGS. 9D, 9E, 9F). Indeed, we found a significant increase in the number of aborted fetuses/litter and smaller litters when dams where treated with AMH as compared to vehicle- and AMH+GnRH antag-treated dams (FIGS. 9D, 9E). We did not observe any changes in the body weights of pups at birth (FIG. 9F).

Example 3

Effect of AMH Excess During Pregnancy

We speculated that peripherally administered AMH could impinge on the maternal GnRH neurons, which express AMHR2, leading to their activation. In order to test that, we quantified the number of active GnRH neurons (GnRH$^+$/Fos$^+$) 90 minutes after i.p. delivery of AMHc into adult female mice (FIG. 7). Indeed, a single AMH injection significantly increased the total number of Fos$^+$ nuclei in the hypothalamic OVLT (organum vasculosum laminae terminalis; FIG. 7) as well as the proportion of GnRH neurons expressing Fos in the same regions (FIG. 7). These results show that peripheral AMH can act centrally by inducing GnRH neuronal activation.

A critical feature of GnRH neurons is their ability to secrete the hormone in discrete pulses; the frequency of which is decoded by the pituitary to evoke preferential synthesis and release of LH or FSH (Wildt L., et al., 1981, Endocrinology Vol. 109, 376-385). Women with PCOS have increased pulsatile GnRH release, which results in higher levels of LH and lower levels of FSH in most individuals. The increased frequency in LH secretion drives steroidogenesis and androgen production by follicular theca cells whereas lower FSH levels lead to anovulation (Chang, R. J. et al., 2007, Nat Clin Pract Endocrinol Metab Vol. 3, 688-695). We speculated that AMH could act on the maternal brain to increase GnRH/LH secretion and ovarian T production. If this hypothesis were to be true, the resulting increase in circulating T in the mothers would then affect the HPG axis of the offspring as it happens in animal models of prenatal androgen exposure.

Figure 3G:
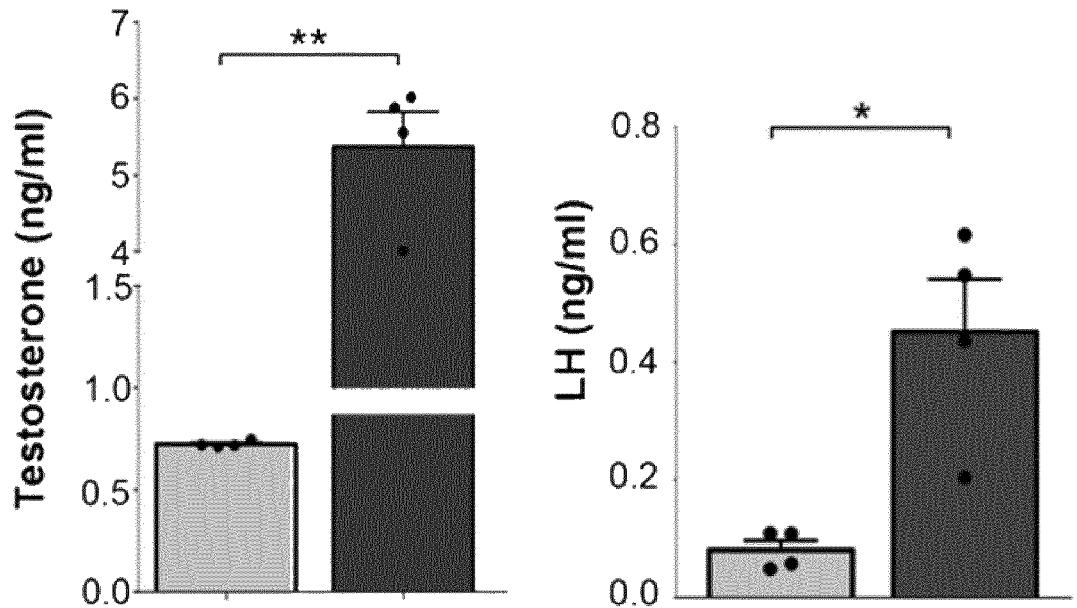

In order to test that, we first measured plasma T in pregnant mice at the end of AMH or PBS stimulation, at E19.5 (FIG. 3G). The plasma T concentration in a single blood sample was more than five-times higher in AMH-treated mothers as compared to the control group (FIG. 3G). These data indicate that three daily AMH injections at the end of the gestation period are sufficient to trigger an increase in T levels in pregnant animals. To assess whether this rise was due to heightened theca cell responsiveness to increased pituitary secretion of LH, we then measured LH levels in these two animal groups. In physiological pregnancy LH levels are known to be almost undetectable as a consequence of the gonadal steroids negative feedback. Unexpectedly, whereas PBS-treated pregnant mice displayed very low levels of LH (<0.1 ng/ml), AMH-treated females showed a robust elevation in circulating LH (>0.4 ng/ml).

Placental tissue could also contribute to increased androgen levels as placentae from women with PCOS have lower aromatase expression resulting in increased androgen levels during pregnancy in PCOS women (Maliqueo, M., et al, 2013,. European journal of obstetrics, gynecology, and reproductive biology Vol. 166, 151-155). In order to test whether the increase in maternal T is also attributable to the AMH-dependent inhibition of aromatase, which is expressed and active in AMHR2-expressing tissues such as the ovaries and placenta, we performed qPCR for the enzyme P450 aromatase (CYP19A1) gene in the placental tissues harvested from pregnant mice at the end of the treatment period (FIG. 3G). In AMH-treated pregnant mice, the expression of Cyp19a1 mRNA was almost undetectable (1000 times lower as compared to control animals) (FIG. 3G).

Figure 3H:
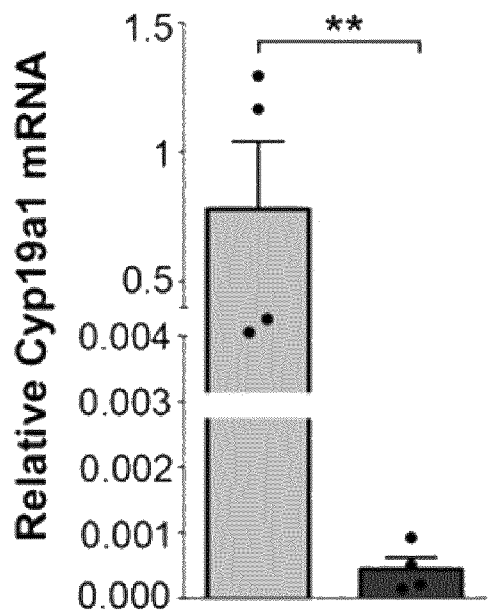
Figures 1, 3I:
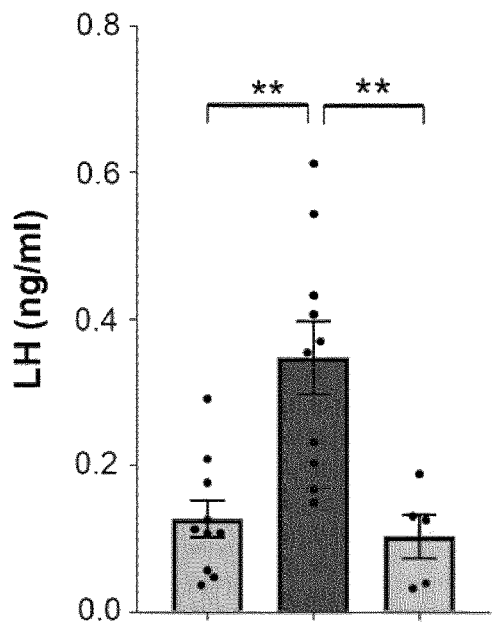
Figures 2, 3I:
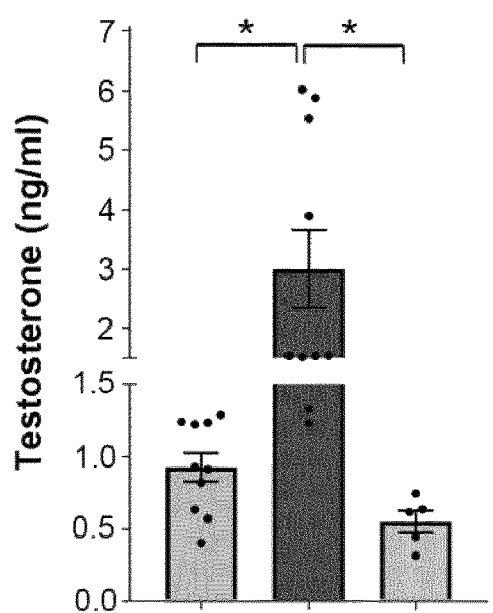
Figures 3, 3I:
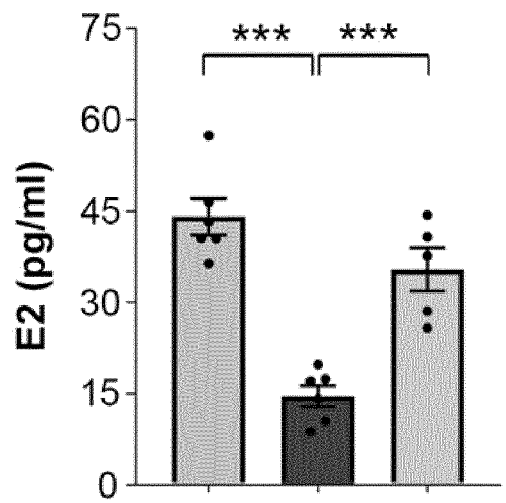
Figures 3, 3I, 4:
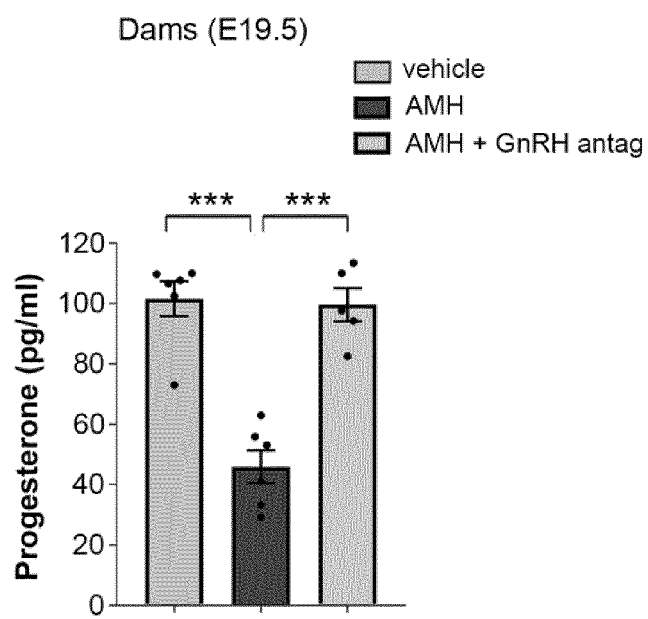
Figures 1, 3J:
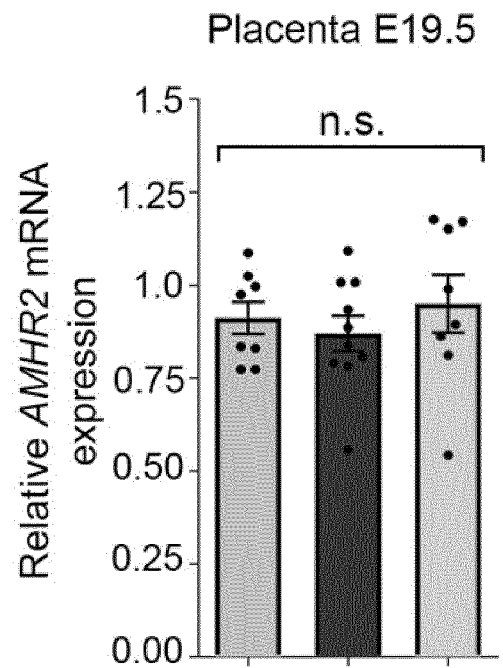
Figures 2, 3J:
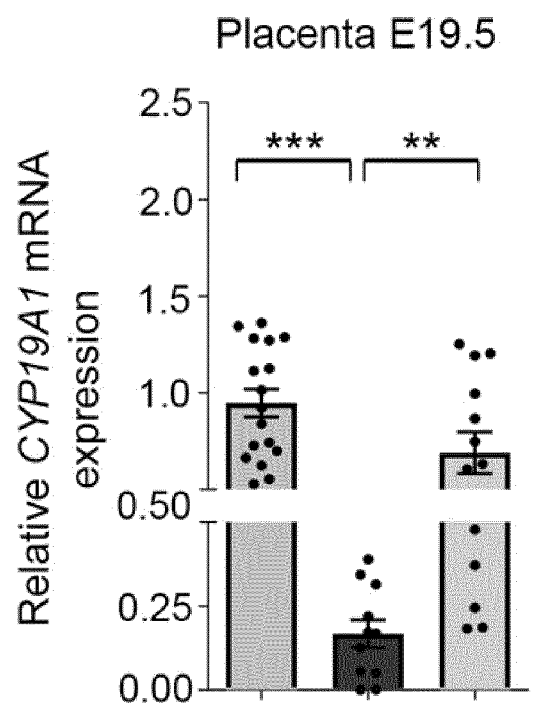
Figures 3, 3J:
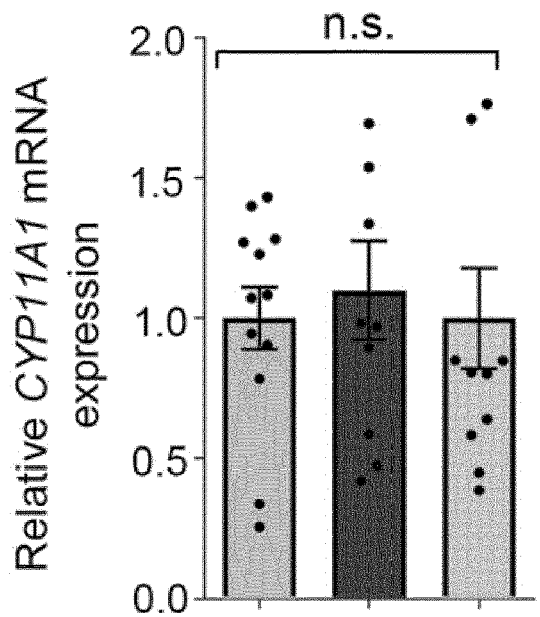
Figures 3, 3J, 4:
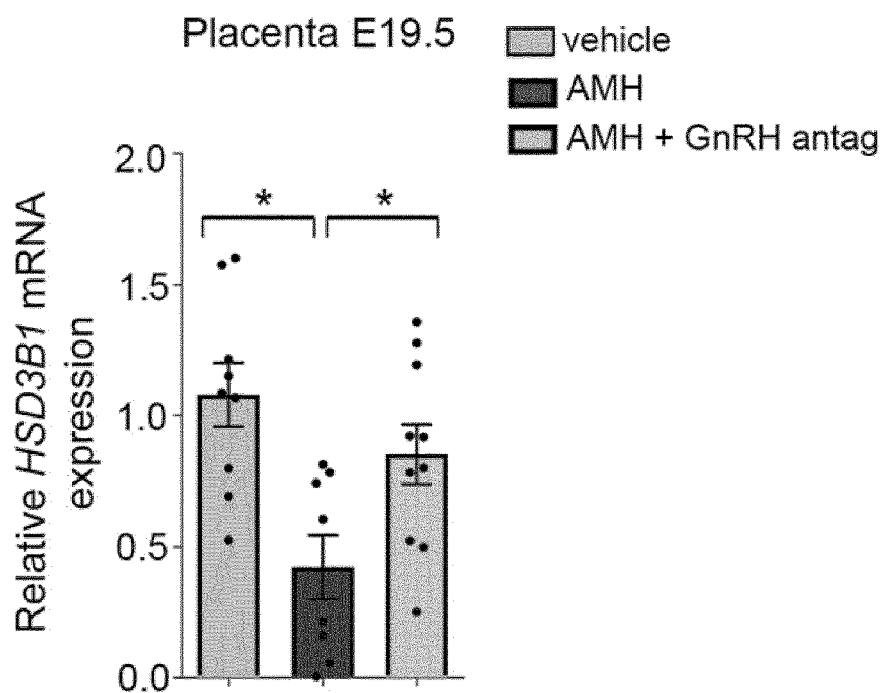

Moreover, since the placenta expresses AMHR2[27], we examined if AMH treatment could alter aromatase expression in the murine placenta. We performed qPCR for the enzyme P450 aromatase (CYP19A1) gene in the placentae harvested from pregnant mice at the end of the treatment period, E19.5 (FIG. 3H). In AMH-treated pregnant mice, the expression of aromatase was 1000 times lower than in PBS-treated pregnant animals (FIG. 3H), indicating that AMH significantly lowers placental aromatase expression.

Altogether, these findings highlight a novel mechanism whereby exposure to AMH excess during pregnancy leads to a cascade of pathophysiologically converging alterations in maternal brain, ovaries and placenta and finally resulting into a strong elevation of circulating T, which could affect the fetal brain.

Example 4

Effects of AMH Excess During Pregnancy on the Offsrping

Figure 4A:
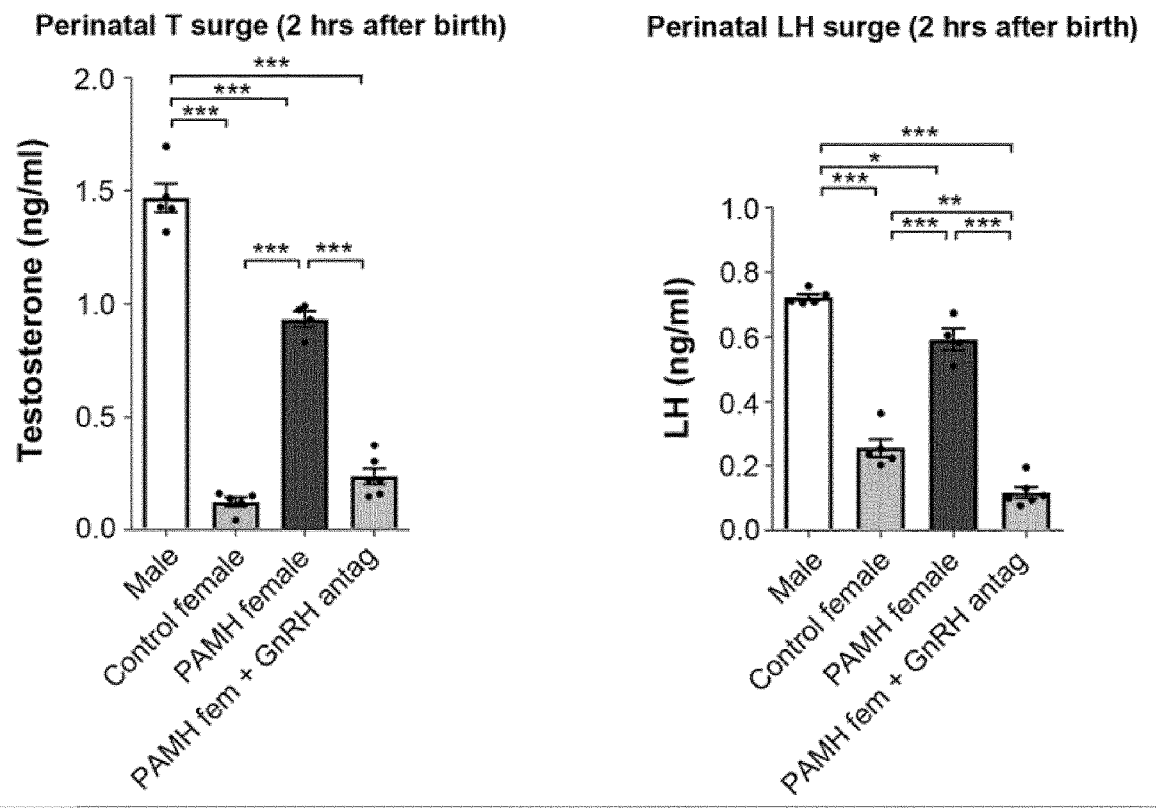
Figure 4B:
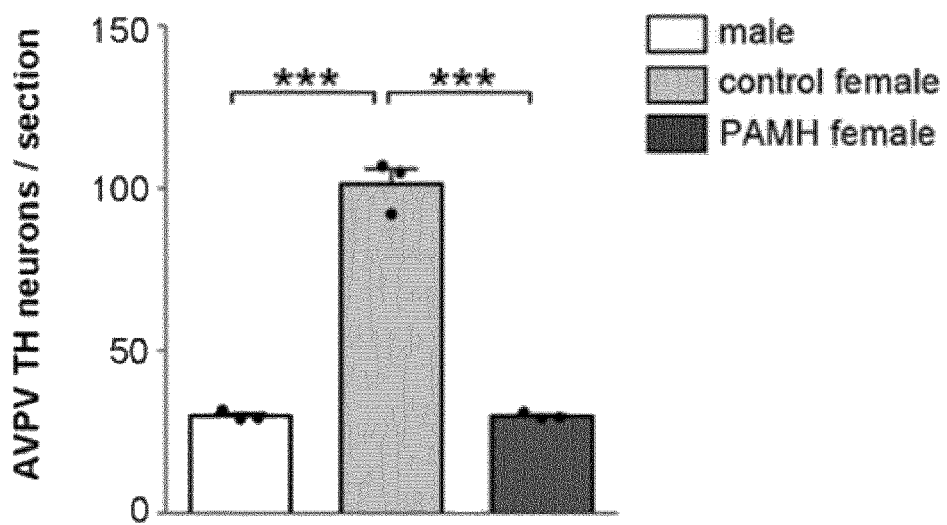

Gonadal steroid hormones are primarily responsible for sexually differentiating the brain by perinatal organizational mechanisms (Simerly et al., 2002, Annu Rev Neurosci Vol. 25, 507-536 2002; McCarthy et al., 2012, J Neurosci Vol. 32, 2241-2247). We therefore next analyzed whether prenatal AMH-dependent maternal androgenization might be associated with disruption of the brain sexual dimorphism in the offspring. Since in most vertebrate species, gonadal T secretion occurs in a sexually dimorphic pattern during the first hours following birth (0-4 hr at P0), being elevated in newborn males but not in females (Corbier et al., 1992, Arch Int Physiol Biochim Biophys Vol. 100, 127-131), we first established the profile of neonatal testosterone secretion in male, control female and PAMH female mice two hours after birth. As expected, T concentrations in male pups were elevated at 2 h post-birth, whereas control female pups exhibited low levels of testosterone (FIG. 4A). Interestingly, T levels in PAMH female pups were significantly higher as compared to control females, although the T concentration in the circulation of the PAMH female pups did not reach the same values detected in the male control group (FIG. 4A).

Since a short-lived (1-12 h) surge in LH secretion is detected exclusively in newborn males of rodent and primate species (Herbison, A. E., 2016, Nature reviews. Endocrinology Vol. 12, 452-466), we also assessed the LH concentration in the serum of these animals and revealed the same pattern as for T, with LH being significantly more elevated in male pups and PAMH female pups as compared with control females (FIG. 4A).

Figures 1, 4C:
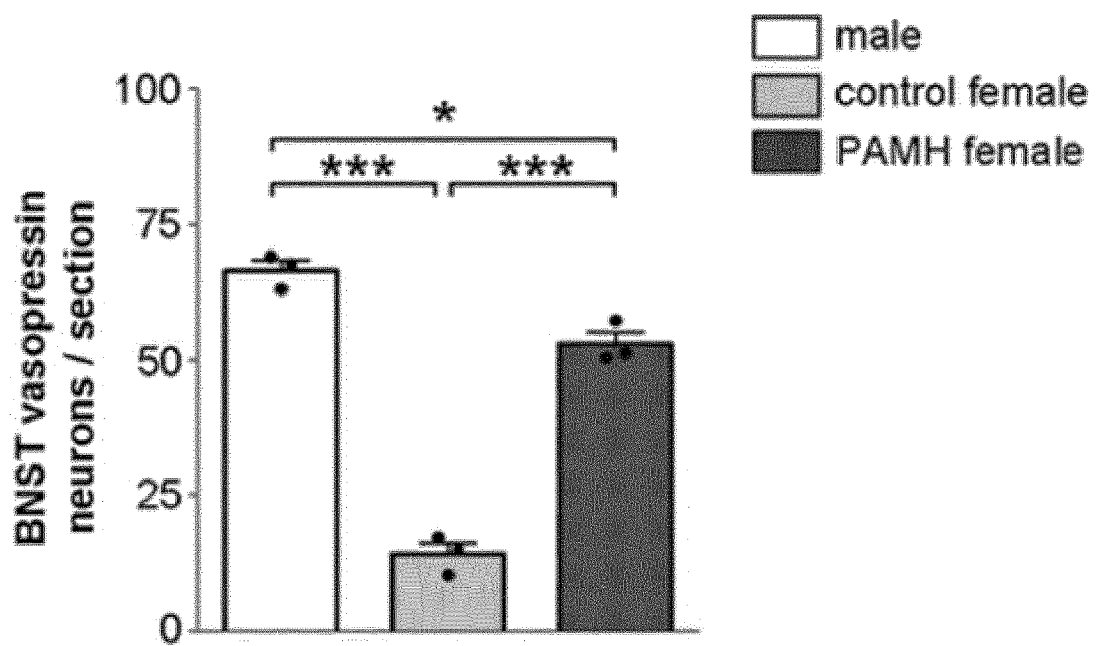
Figures 2, 4C:
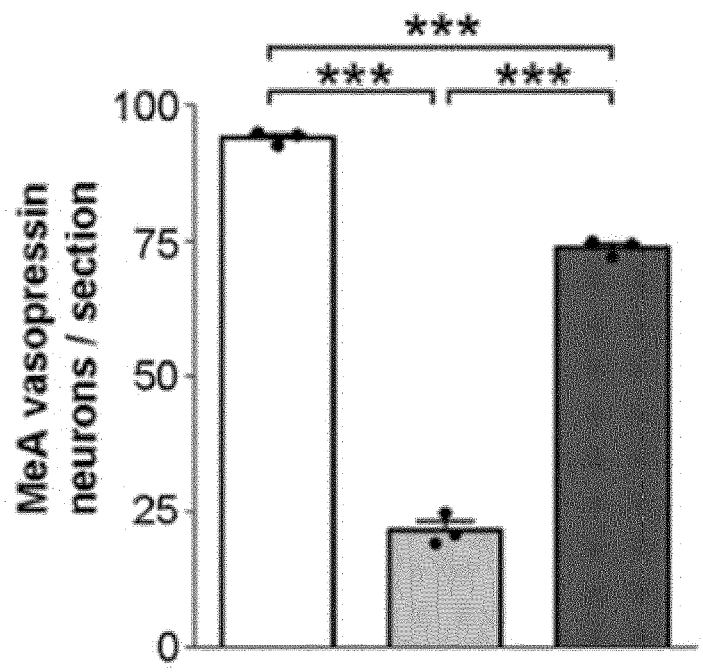

The transient T surge at birth is responsible for establishing sexually dimorphic brain circuitry that controls sexually differentiated behaviors and reproductive physiological processes (Lenz et al., 2010, The European journal of neuroscience Vol. 32, 2096-2104). We thus next analyzed the organization of the sexually dimorphic areas in the brains of adult males, control and PAMH female offspring. The two markers of sexual differentiation were the female-dominant tyrosine hydroxylase (TH) neuron population in the anteroventral periventricular nucleus (AVPV) of the hypothalamus (Simerly, R. B., 1989, Brain Res Mol Brain Res Vol. 6, 297-310) and the male-dominant vasopressin expression in the bed nucleus of the stria terminalis (BnST) and the medial amygdaloid nucleus (MeA) (De Vries et al., 2006, Neuroscience Vol. 138, 947-955). As previously documented (Simerly, R. B., 1989, Brain Res Mol Brain Res Vol. 6, 297-310), a female-dominant sex difference was detected in the number of TH neurons in the AVPV of control females versus males (FIG. 3B). However, PAMH female mice exhibited a male-like number of TH cells located in the same regions (FIG. 3B). A similar masculinization was observed in the male-dominant vasopressin expression in the BnST and MeA, with the number of vasopressin-immunoreactive cells in PAMH female offspring trending toward being male-like as compared with control females (FIG. 4C-1, 4C-2).

These results show that PAMH female offspring exhibit a masculinization of both the neonatal T and LH surge, followed by a strong masculinization of the sexually dimorphic brain regions that regulate reproduction.

Example 5

Figure 5A:
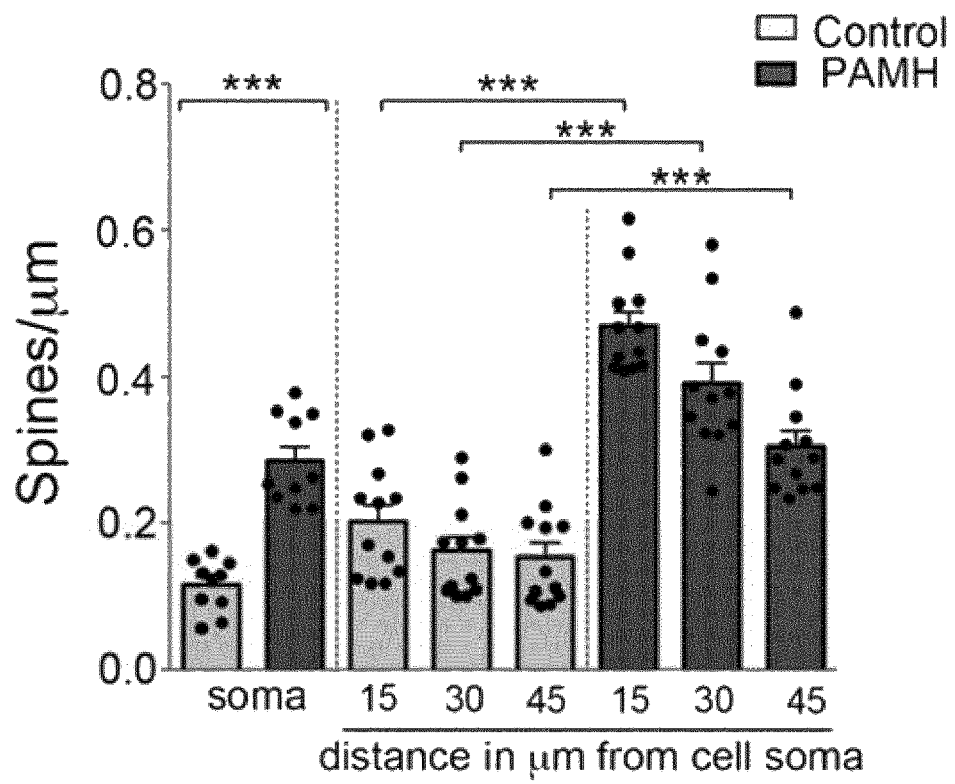
FIGS. 5A-5G. PAMH mice exhibit higher GnRH dendritic spine density, increased GABAergic inputs to GnRH neurons and elevated firing frequency of GnRH neurons in adulthood.
Figure 5B:
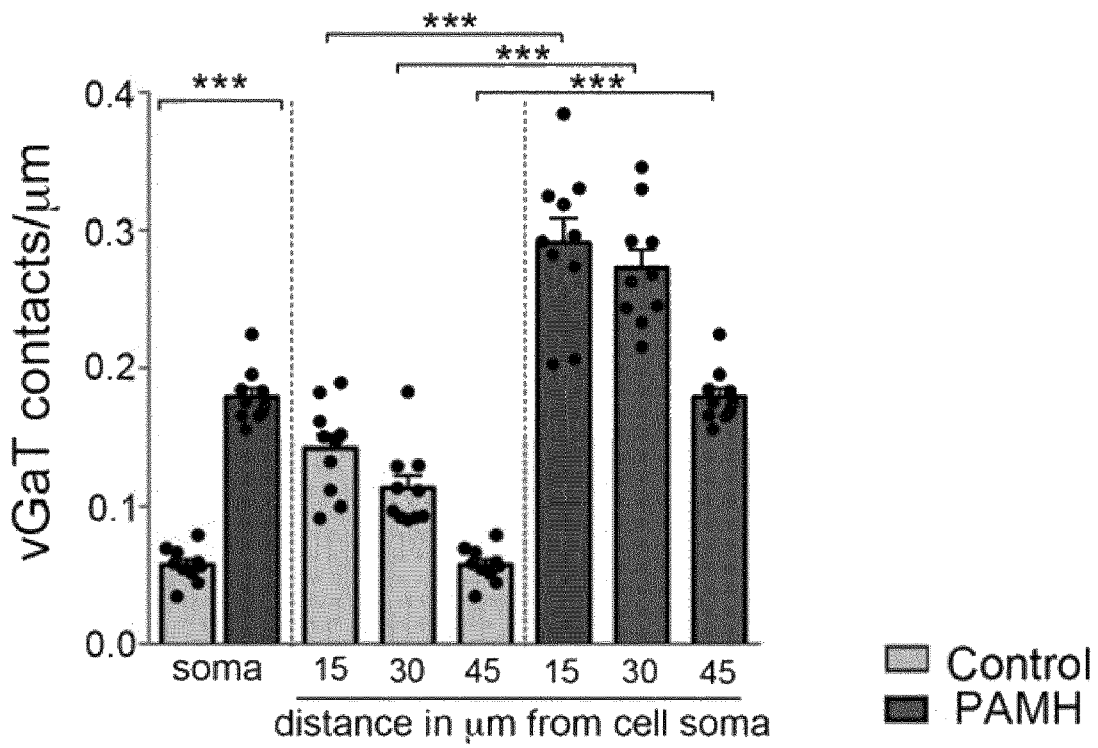

In Utero Exposure to Excess AMH Permanently Alters the GnRH Neuronal Afferent Network and the GnRH Neuronal Activity in the Offspring Given that GnRH neurons represent the final common pathway in the neural control of fertility, the next question was to determine whether the robust hormonal and morphological androgenization detected in the PAMH animals could also lead to organizational and or activational changes in GnRH neuronal morphology and activity in adulthood. Using GnRH-GFP mice and 3D-reconstruction analysis, we identified increased spine density both on the soma and along the primary dendrite (up to 45 μm) in PAMH female mice compared with controls during diestrus (FIG. 5A,). Notably, a previous study revealed greater dendritic spine density in GnRH neurons as well as increased GABAergic but not glutamatergic inputs in mice following prenatal androgen exposure (Moore et al., 2015, Proceedings of the National Academy of Sciences of the United States of America Vol. 112, 596-601). Moreover, Sullivan and Moenter showed increased GABAergic postsynaptic currents in GnRH neurons of PNA mice (Sullivan et al., 2004, Proceedings of the National Academy of Sciences of the United States of America Vol. 101, 7129-7134). We therefore examined whether the increase in spine density did correlate with increased GABAergic appositions with GnRH neurons in control and PAMH GnRH-GFP mice. We counted the number of the vescicular GABA Transporter (vGaT)-ir puncta on GnRH cell soma and proximal dendrite (up to 45 μm) and found a significant increase in the number of vGaT apposition to GnRH cells in PAMH mice compared with controls during diestrus (FIG. 5B).

Although principally recognized as an inhibitory neurotransmitter in the adult brain, there is now a consensus that GABA acts through GABAA receptors to trigger cell depolarization and activate adult GnRH neurons (Sullivan et al., 2004, Proceedings of the National Academy of Sciences of the United States of America Vol. 101, 7129-7134).; Herbison et al., 2011, Journal of neuroendocrinology Vol. 23, 557-569).

Figure 5C:
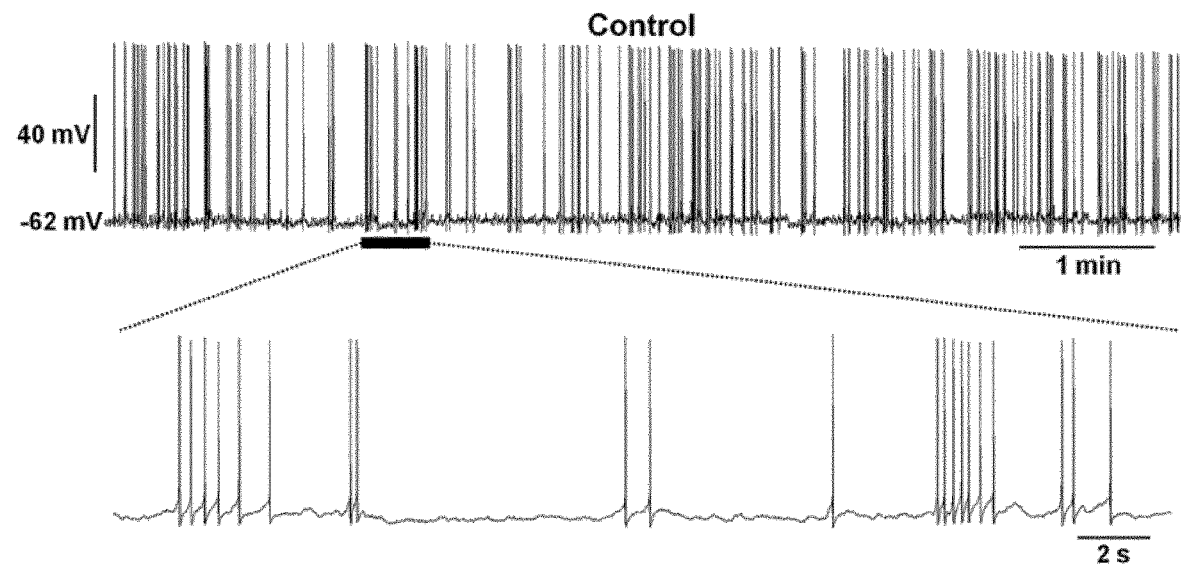
Figure 5D:
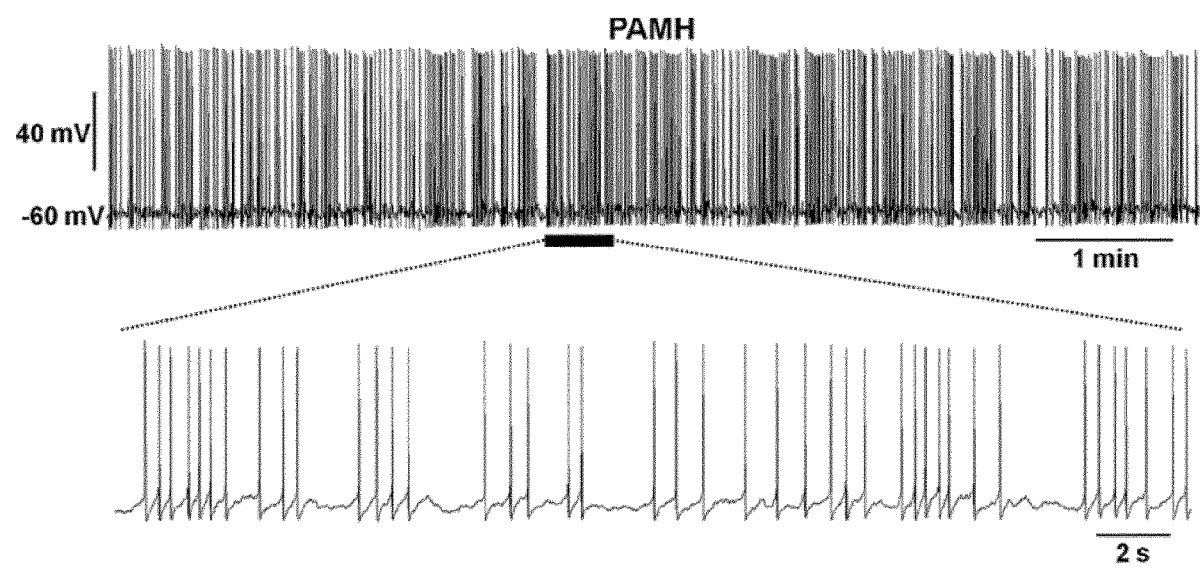
Figure 5E:
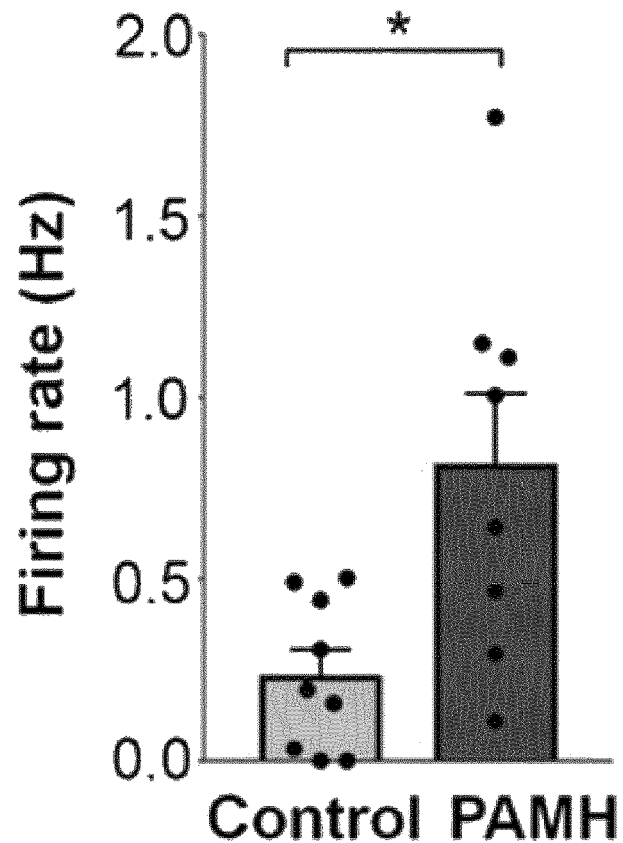

In order to test whether elevated excitatory innervation of GnRH neurons increases GnRH pulse frequency in our preclinical model of PCOS, we performed electrophysiological recordings of GnRH neurons in acute brain-slice preparations containing the POA of GnRH-GFP mice during diestrus, when GnRH secretion into the portal circulation is low (FIG. 5C to 5G). Whole-cell current-clamp recording showed a robust increase in the spontaneous burst firing of GnRH neurons of PAMH mice, with a three-fold significant increase in the average firing rate of PAMH GnRH neurons as compared with controls (FIG. 5C to 5E). The average resting membrane potential (RMP) and average input resistance (Rin) of GnRH neurons recorded was similar in control and PAMH mice (FIG. 5C to 5G), suggesting that the increase in the GnRH spontaneous firing activity observed in PAMH mice is most likely due to the increase in the hypothalamic afferent excitatory network rather than to intrinsic changes in GnRH neuronal excitability.

Environmental factors may play a role in the early stages of human development and experimental animal studies suggest that maternal hyperandrogenism at a critical fetal stage may cause permanent changes in fetal physiology that can trigger PCOS development later in life (Jayasena et al., 2014, Nature reviews. Endocrinology Vol. 10, 624-636), however the mechanisms of the elevation of androgens in PCOS remain enigmatic. Using our novel preclinical PCOS model (PAMH), we here showed that prenatal exposure to elevated AMH levels increases GnRH/LH pulsatility in pregnant mice, which drives steroidogenesis and hyperandrogenism. The maternal androgenization is further exacerbated by inhibition of aromatase expression in the placenta leading to an increase in T bioavailability. This triggers a cascade of events in the offspring, which converge into their androgenization, alteration in the wiring of the hypothalamic networks regulating reproduction, increase in the excitatory drive to GnRH neurons and a persistent rise in the GnRH neuronal firing activity in adulthood. Finally, the persistent hyperactivity of GnRH neurons in adult offspring drives ovarian androgen production and impairs folliculogenesis and ovulation, contributing to the vicious circle of PCOS (FIG. 9).

Together our results point to the prenatal GnRH antagonist treatment as a new promising potential therapeutic strategy to prevent the transgenerational transmission of the disease.

Example 6

Postnatal Treatment with GnRH Antagonist in PAMH Mice Normalizes their Neuroendocrine Phenotype Since our results uncovered a persistent hyperactivation of GnRH neurons in PAMH female animals, we reasoned that competing with natural GnRH for binding to membrane receptors on gonadotropes and thus decreasing the rate of LH and FSH release would ameliorate the PCOS-like phenotype observed in these mice.

Figure 6A:
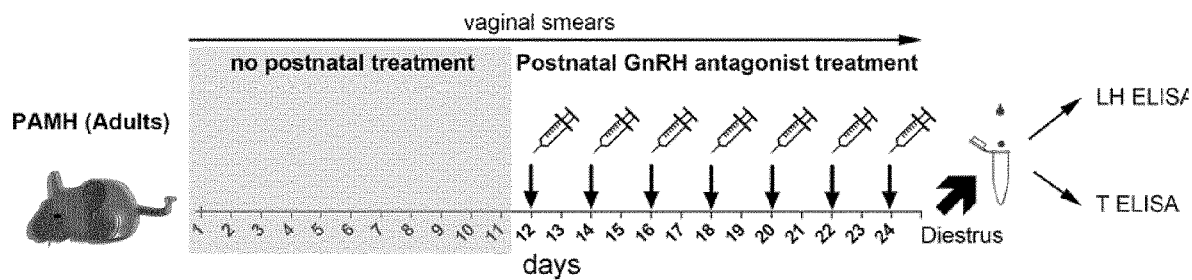
Figure 6B:
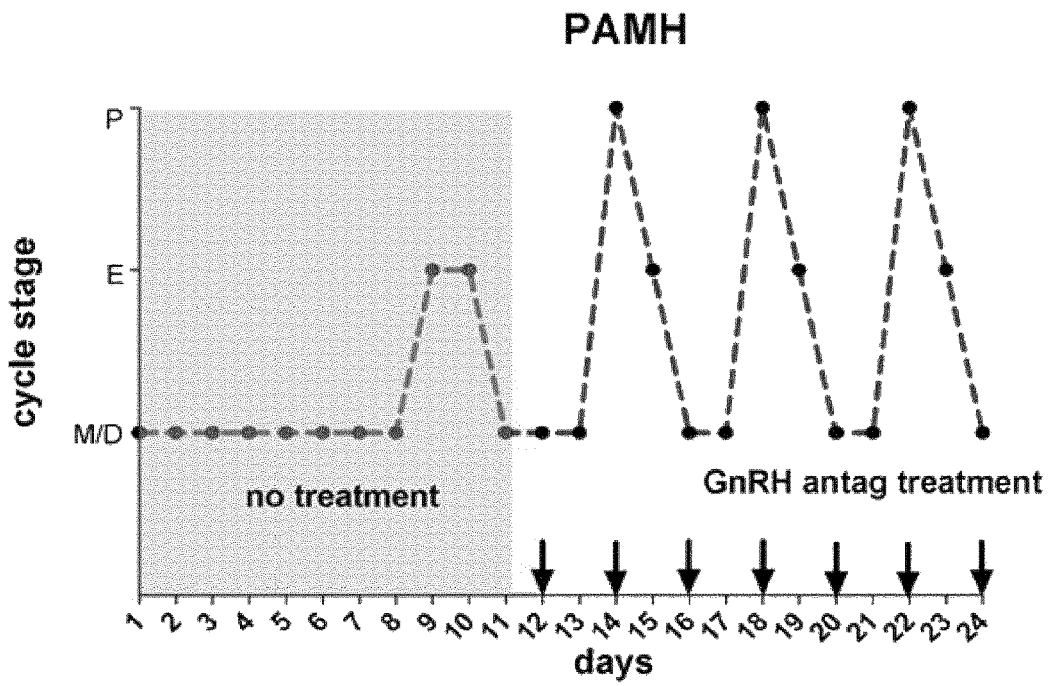
Figure 6C:
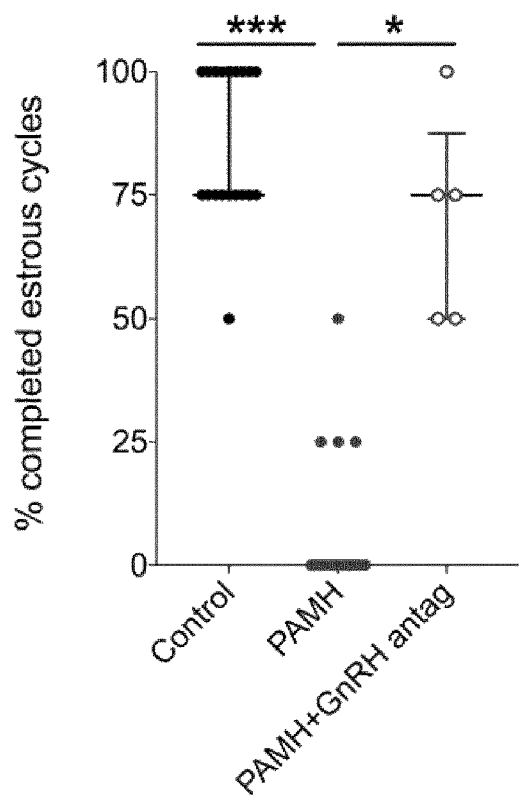
Figure 6D:
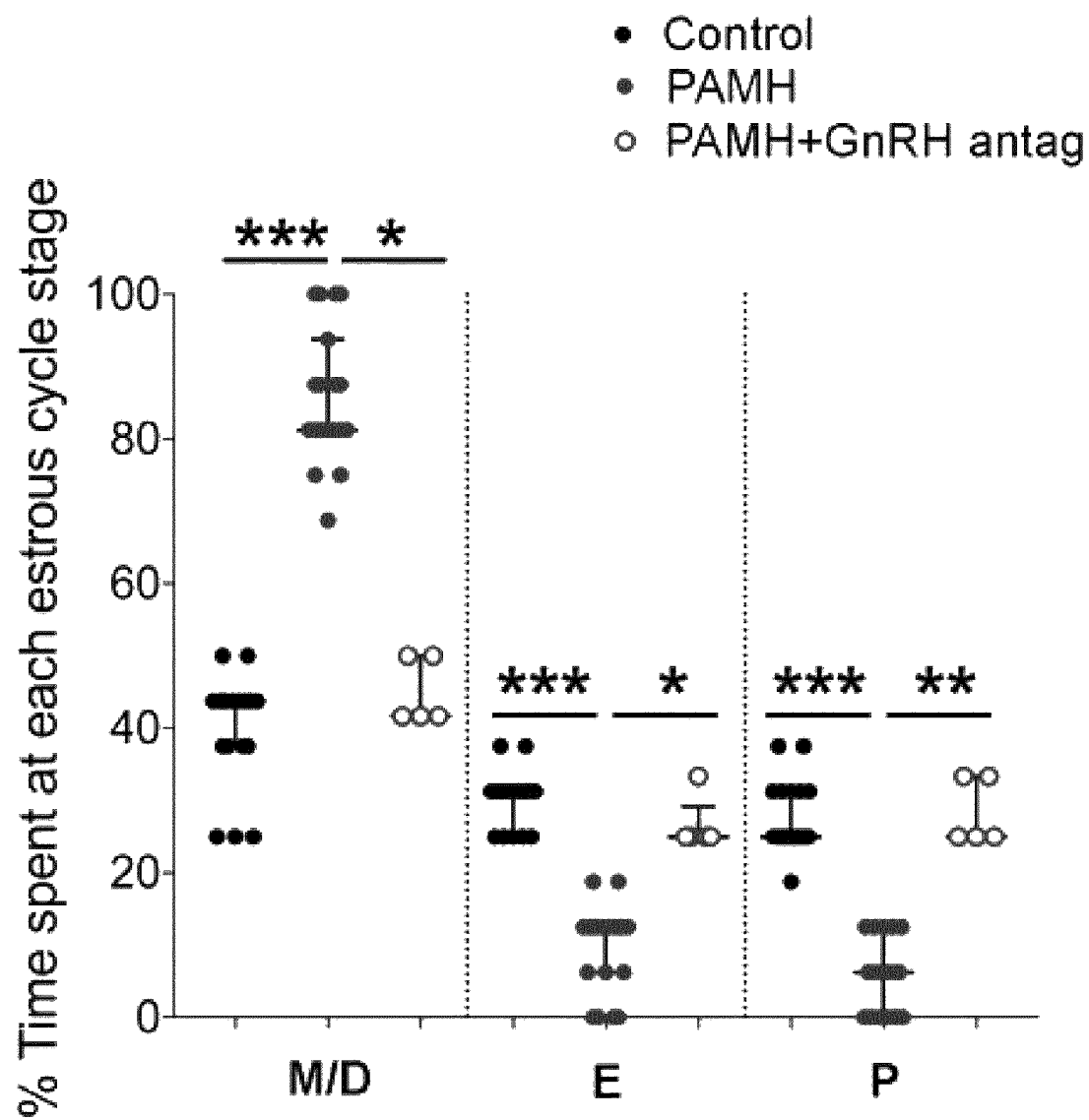
Figure 6E:
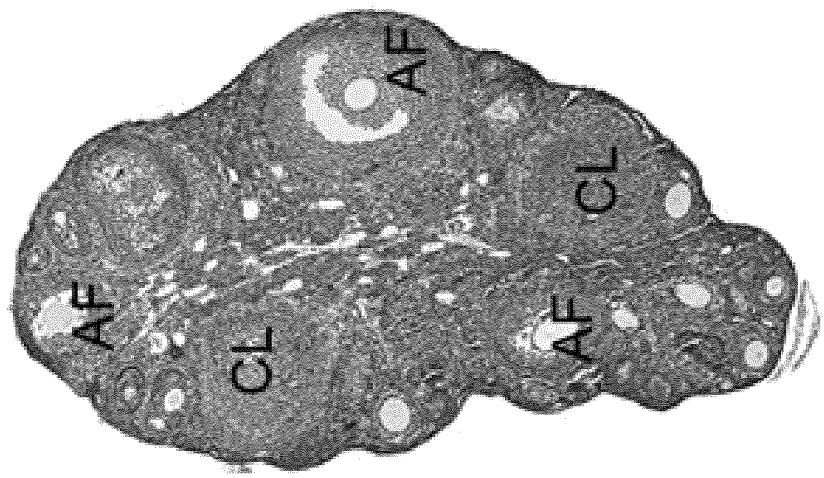
Figure 6E:
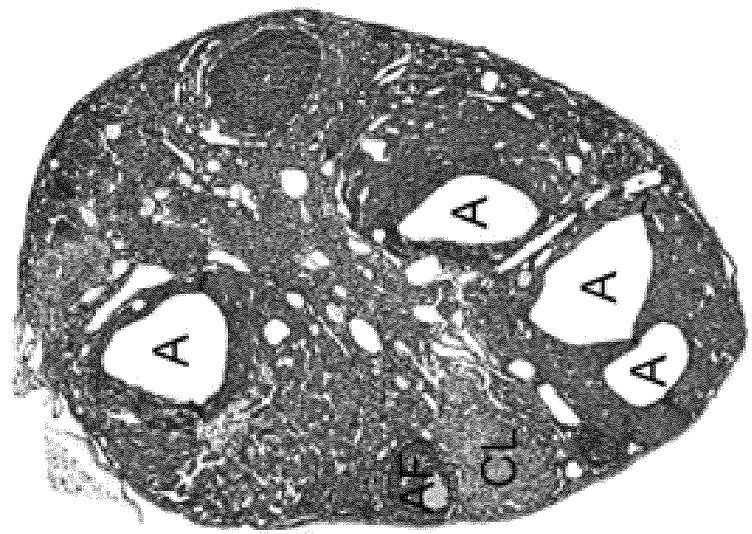
Figure 6E:
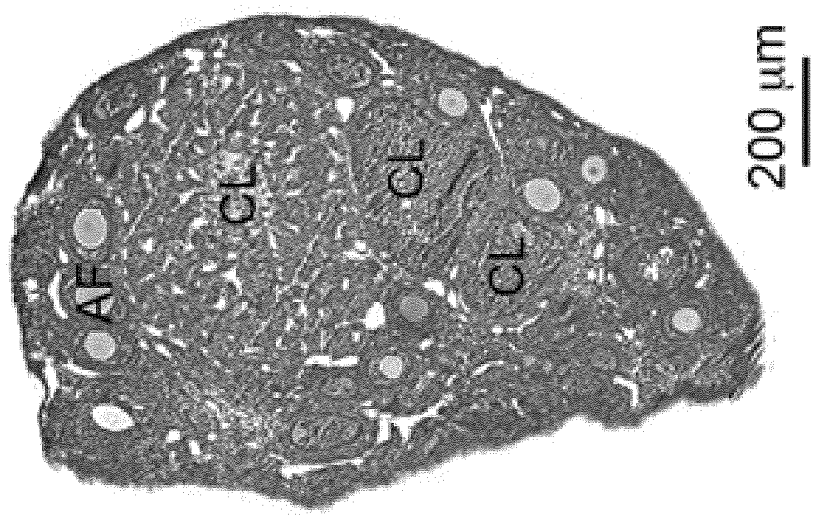
Figure 6F:
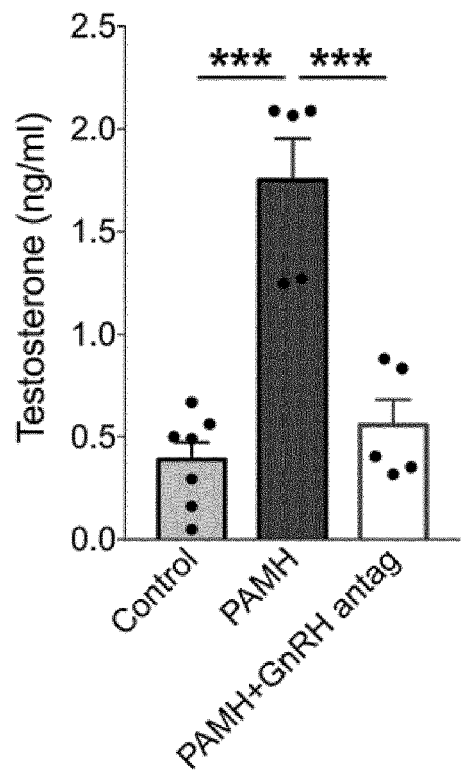
Figure 6G:
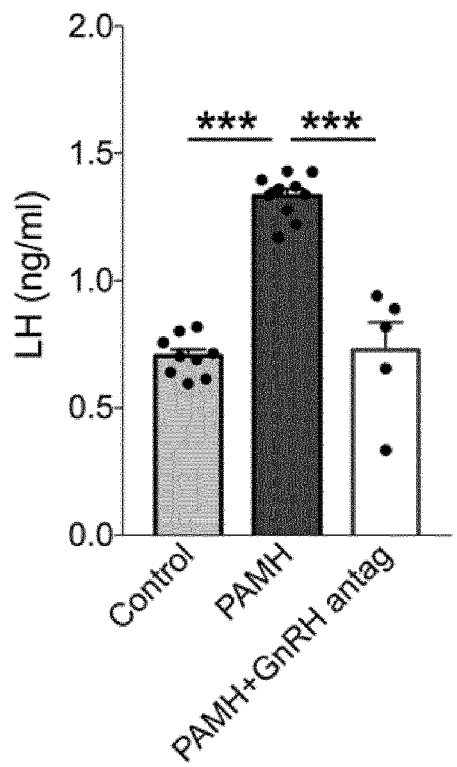

In order to assess that, we first analyzed estrous cyclicity of PAMH female mice for 12 days and subsequently treated these animals every two days with i.p. injections of GnRH antagonist (0.5 mg/Kg$^{-1}$ Cetrorelix acetate/per injection) for 12 additional days (FIG. 6A). At the end of the treatment period (at first diestrus), trunk blood was collected for LH and T measurements. As expected, PAMH mice were oligoanovulatory but estrous cyclicity was restored during the GnRH antagonist treatment (FIGS. 6B, 6C, 6D). Accordingly, the ovarian morphology of PAMH+GnRH antagonist mice was restored as compared to PAMH animals, with PAMH+GnRH antagonist ovaries displaying evident corpora lutea, antral follicles, and no trace of atretic follicles (FIG. 6E). Finally, the aberrant T and LH values observed in PAMH mice were also normalized following the GnRH antagonist treatment, which did not differ from control mice (FIGS. 6F, 6G). These data show that postnatal GnRH antagonist treatment can restore the major PCOS-like traits of PAMH mice, namely: ovulation, ovarian morphology and hormonal levels (T and LH).

Example 7

Figure 5F:
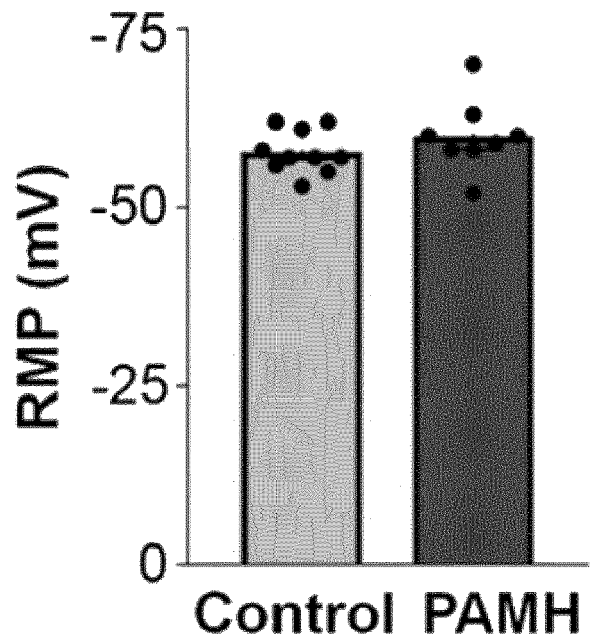
Figure 5G:
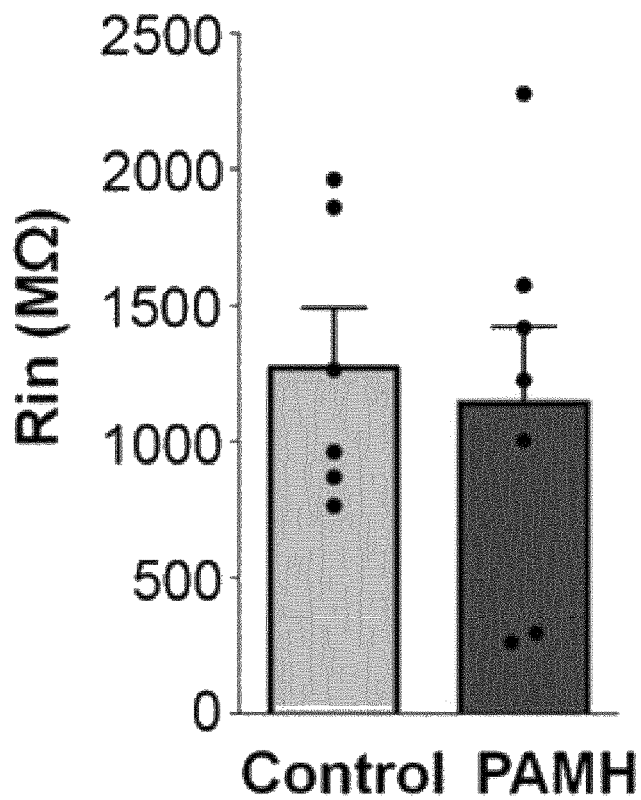

In Utero Exposure to Excess AMH Permanently Alters the GnRH Neuronal Afferent Network and the GnRH Neuronal Activity in the Offspring Given that GnRH neurons represent the final common pathway in the neural control of fertility, a crucial point was to determine whether the marked hormonal and morphological signatures of androgenization detected in the PAMH animals were accompanied by protracted changes in GnRH neuronal morphology and electrical activity during adult life. Using GnRH-GFP mice and 3D-reconstruction analysis, we identified increased spine density both on the soma and along the primary dendrite (over the proximal 45 μm distance) in PAMH female mice compared with controls during diestrus (FIG. 5A, 5B, 5C, 5D, 5E). We next analyzed whether this increased spine density was correlated with increased Glutamatergic or GABAergic appositions. By counting the number of the vesicular glutamate transporter 2 (vGluT2)-immunoreactive (ir) puncta (associated with the primary dendrite of GnRH cells), we found no significant differences in the number of appositions of vGluT2 of PAMH compared to control female mice at diestrus. However, when we counted the vesicular GABA Transporter (vGaT)-ir puncta on GnRH cell soma and proximal dendrite, we detected a significant increase in the number of vGaT appositions onto GnRH cells of PAMH compared to control, female diestrous mice (FIG. 5F, 5G, 5H). Although principally recognized as an inhibitory neurotransmitter in the adult brain, there is now a consensus that GABA is excitatory in adult GnRH neurons. In order to test whether the elevated hypothalamic excitatory appositions onto GnRH neurons in our preclinical model of PCOS effectively translates into increased neuronal activity, we performed whole-cell current-clamp recordings of GnRH-GFP neurons in acute coronal brain slices containing the preoptic area (POA). The recordings were done in animals sacrificed at diestrus, when GnRH secretion into the portal circulation is low (FIG. 5C, 5D, 5E, 5F, 5G). GnRH neurons from PAMH mice showed a robust, significant three-fold increase in their spontaneous action potential firing rate, as compared with controls (FIG. 5C, 5D, E). The average resting membrane potential (RMP) and average input resistance ($R_{in}$) of GnRH neurons were similar in control and PAMH mice (FIG. 5F, 5G). Since $R_{in}$ and the membrane capacitance ($C_m$) did not differ significantly among groups (mean±s.e.m.; Control: 41.348±5.121 pF, n=6; PAMH: 39.893±3.921 pF, n=7; Student's t-test: P=0.823, t=0.229), we can assume that the change in GnRH neuronal firing in PAMH animals compared to control animals is not due to modifications of passive electrical membrane properties.

Example 8

GnRH Antagonist Treatment of Adult PAMH Mice Normalizes their Neuroendocrine Phenotype Since our results uncovered a persistent hyperactivation of GnRH neurons in PAMH female animals, we reasoned that partially competing with natural GnRH for binding to membrane receptors on gonadotropes and thus decreasing the rate of LH and FSH release would ameliorate the PCOS-like phenotype observed in these mice.

To assess this, we analyzed estrous cyclicity of adult PAMH female mice, over 90 days, before, during and after i.p. injections of increasing doses of GnRH antagonist (0.05 mg/Kg, 0.5 mg/Kg and 5 mg/Kg Cetrorelix acetate/per injection; FIG. 10A). We monitored daily vaginal cytology of PAMH animals throughout this time: before the beginning of the treatments, during the Cetrorelix administrations and during the recovery times (discontinuation of treatment; FIG. 10A).

As shown in FIG. 2, PAMH mice display prolonged time in metestrus/diestrus as compared to the control female offspring (FIG. 10A, grey areas).

Therefore, we initially monitored estrous cyclicity and LH concentrations in PAMH mice for 12 days before the beginning of Cetrorelix treatment to ascertain that the animals included in the experimental paradigm displayed the typical PCOS-like neuroendocrine alterations. Subsequently, in order to normalize GnRH action on the pituitary (partial inhibition of GnRH receptor), we injected mice i.p. every second day with Cetrorelix acetate at 0.05 for 12 days, followed by a recovery period (no treatment) and by 12 days treatment (every second day) with Cetrorelix acetate at 0.5 mg/Kg (FIG. 10A). Tail-blood samples were collected for LH measurements twice during the GnRH antagonist treatment and once during the 10 days recovery time, that followed each administration period. To attain a complete blockade of GnRH receptor and suppression of LH secretion, we finally injected daily the same mice with 5 mg/Kg Cetrorelix acetate over 12 days (FIG. 10A).

As expected, PAMH mice were oligo-anovulatory, displaying about 25% of completed estrous cycles during 12 days as compared to control mice (FIG. 10B). Notably, normal estrous cyclicity was restored only when animals were injected with 0.5 mg/Kg of GnRH antagonist but not with the lowest or highest doses of the antagonist (0.05 mg/Kg and 5 mg/Kg Cetrorelix acetate; FIG. 10B). LH concentrations were also measured in PAMH and Control mice before the beginning of the treatments (Cetrorelix acetate for the PAMH group and PBS for the Control group), at day 2 and day 6, after the beginning of each treatment, and 4 days after the last injection (recovery time; FIG. 10C). The time-course and dose-effect experiments showed that the high mean LH values, initially observed in PAMH mice, were normalized following the GnRH antagonist treatment at the 0.5 mg/Kg dose only (FIG. 10C). Serum LH levels in PAMH mice following the injections with the lowest dose of Cetrorelix acetate (0.05 mg/Kg) were found to be significantly more elevated than in Control animals, whereas they were significantly suppressed when PAMH mice were treated with the highest dose at 5 mg/Kg (FIG. 10C). As in clinical practice, the effects of Cetrorelix on LH secretion were reversible a few days after discontinuation of treatment, independently by the dose of the injected drug (FIG. 10C).

Figure 10D:
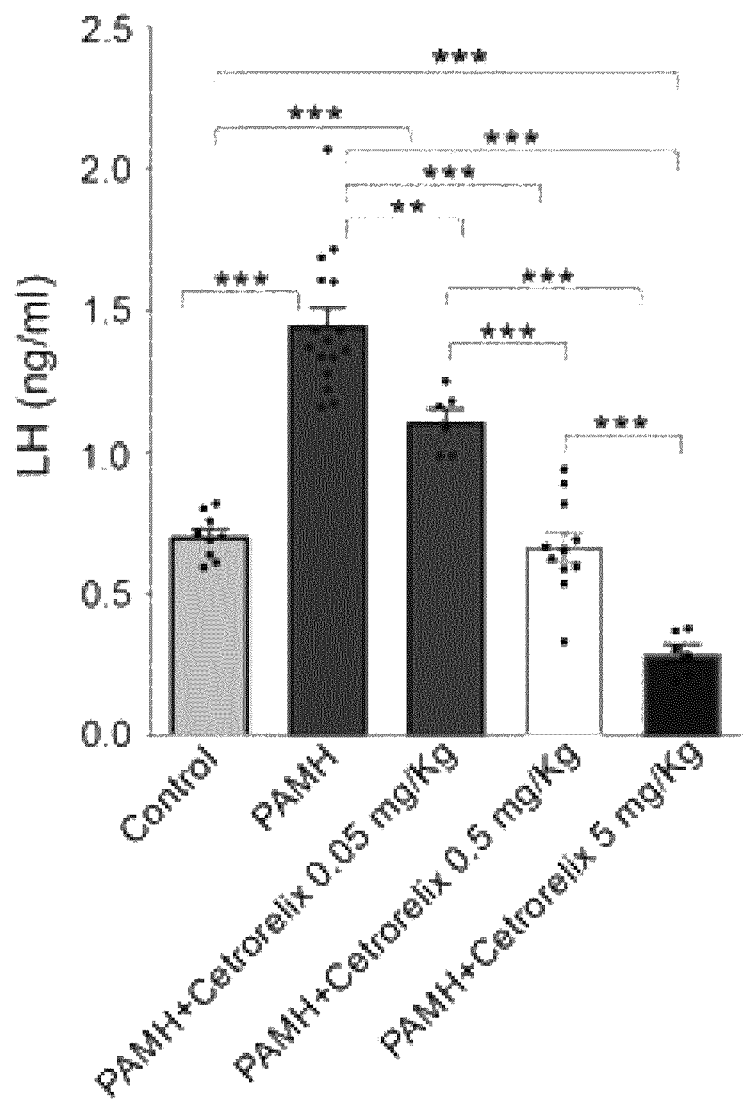
Figure 10E:
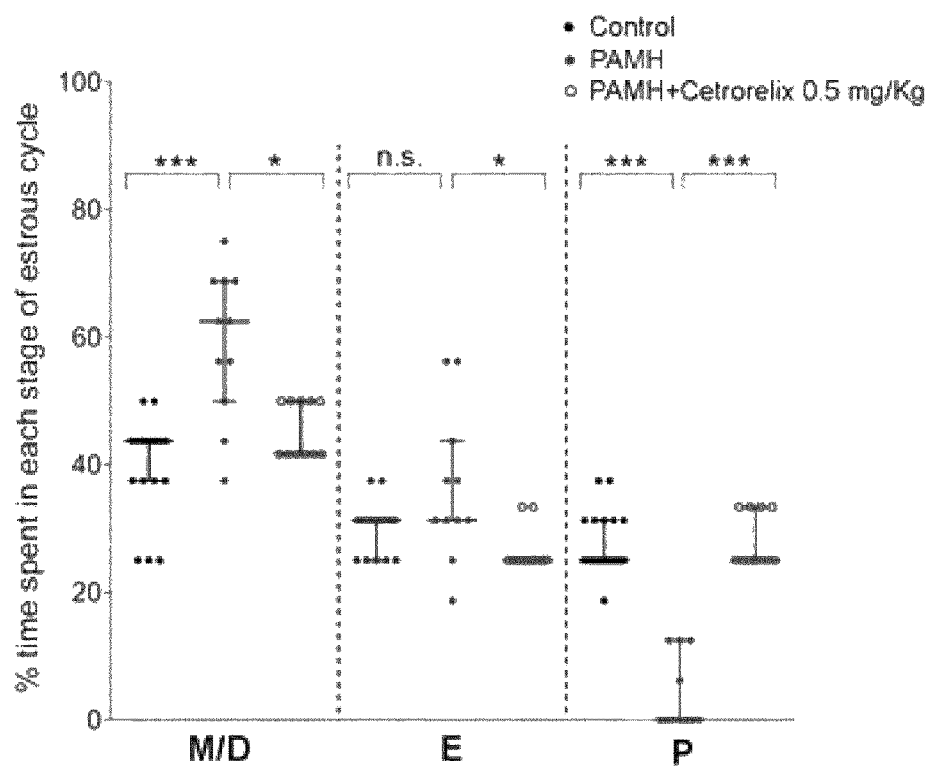
Figure 10F:
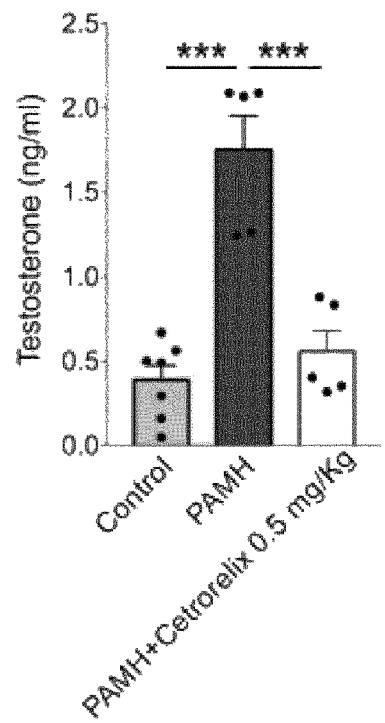
Figure 10G:
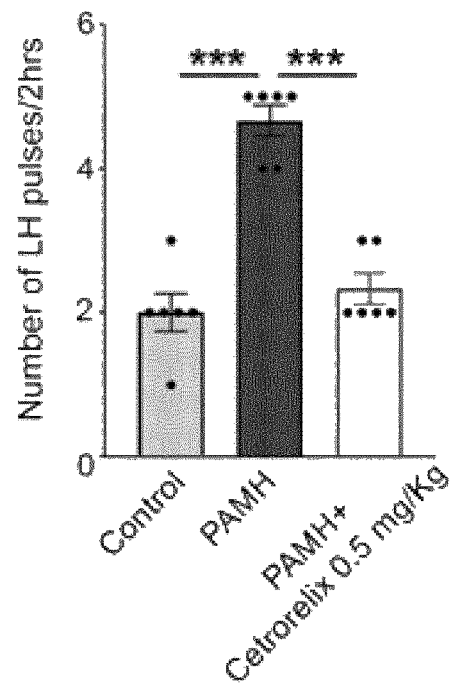
Figure 10H:
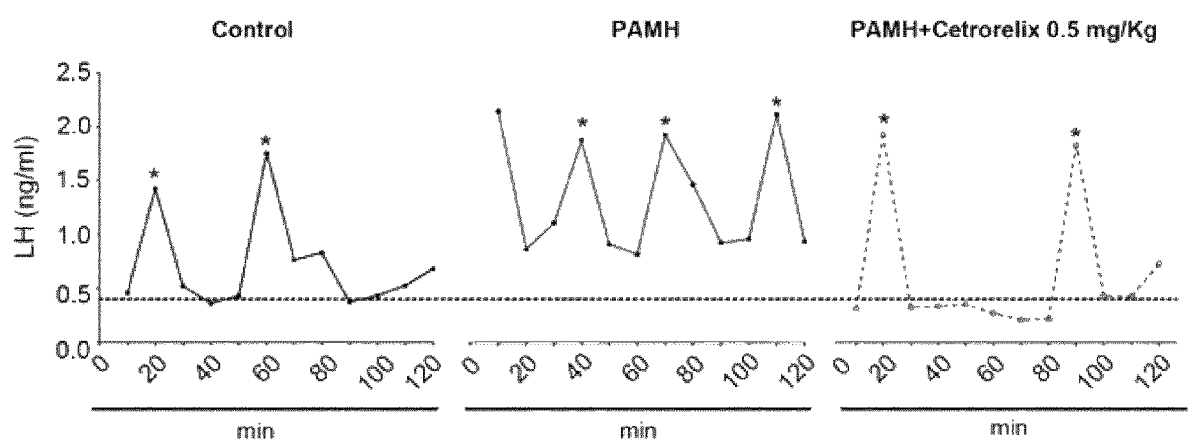

After having identified the concentration of the GnRH antagonist which corrected the serum LH levels and estrous cyclicity in adult PCOS-like animals (0.5 mg/Kg), we performed the rest of the experiments injecting PBS or Cetrorelix at 0.5 mg/Kg every second day (FIG. 10D; 10E, 10F, 10G, 10H). We monitored for 12 days the estrous cyclicity of Control, PAMH and PAMH+Cetrorelix-treated mice and analyzed the % of time that animals spent in each cycle stage (Metestrus/Diestrus, M/D; Estrus, E; Proestrus, P). We found that Cetrorelix at 0.5 mg/Kg, injected every 48 hours, restored ovulation in PAMH animals (FIG. 10D). We then measured T and LH concentrations in these groups, during diestrus, at the end of the treatment time (FIG. 10E, 10F). The aberrant T and LH concentrations observed in PAMH mice were also normalized by the Cetrorelix treatment at 0.5 mg/Kg (FIG. 10E, 10F). Finally, we studied LH pulsatility in Control, PAMH and PAMH+Cetrorelix-treated mice during diestrus, at the end of the treatment time (FIG. 10G, 10H). Also in this case, the GnRH antagonist treatment normalized the LH pulsatility in PAMH animals.

These data show that postnatal GnRH antagonist treatment can rescue the major PCOS-like traits of PAMH mice: oligo-anovulation, hyperandrogenism, increased LH concentrations and LH pulsatility.

Discussion of the Results Depicted in the Examples

In this study, we found a positive relationship between AMH levels and hyperandrogenism in pregnant lean women with PCOS but not in obese PCOS pregnant patients. We do not know whether a causal-relationship between AMH and T might exist during gestation in humans. However, our results in mice demonstrate that AMH has a programming effect leading to gestational and perinatal hyperandrogenism and subsequent changes in the HPG axis and hormone levels of both the dams and the progeny. Our data show for the first time that peripheral bioactive AMH (AMHc) can access the maternal brain, at the level of the ME, and act centrally by inducing GnRH neuronal activation, as demonstrated by the increase in $GnRH^+/Fos^+$ neurons shortly after peripheral administration of AMH. Circumventricular organs, like the ME and the OVLT, contain highly permeable, fenestrated endothelial cells, that allow the free passage of molecules below 35 kDa. Therefore, circulating AMHc can have direct access to GnRH dendrites and terminals, which express AMHR2 both in mice and humans, and that extend outside the blood-brain barrier in the OVLT and in the ME.

The AMH in blood is generally presumed to be the bioactive cleaved AMHc, although recent studies suggested that human blood might contain mainly proAMH and $AMH_{N,C}$. Whether the $AMH_{N,C}$ undergoes some further cleavage, in proximity of the ME, remains to be fully investigated. Although, the fact that peripheral administration of either proAMH or AMHc leads to overlapping phenotypes in the offspring supports the latter hypothesis.

Here, we have generated the most relevant PCOS mouse model, from a clinical perspective, since our model is based on an AMH-driven gestational hyperandrogenism, which is then responsible for the pathophysiological alterations leading to the acquisitions of PCOS cardinal defects in the offspring. This fits well with previous studies demonstrating that gestational hyperandrogenism in monkeys, either occurring naturally or induced by T treatment, induces PCOS-like reproductive and metabolic traits in adulthood.

Our findings highlight a novel pathophysiological mechanism whereby exposure to AMH excess during pregnancy leads to a cascade of alterations impacting the maternal brain, the ovaries and the placenta. This results into a strong elevation of maternal LH and T, and in a drop of P and E2. The maternal androgenization is most likely the result of a dual action of AMH on the dams: 1) a central action and exacerbation of GnRH/LH-driven ovarian steroidogenesis and 2) a peripheral action and inhibition of placental aromatase and HSD3B1 expression, leading respectively to an increase in T bioavailability and a drop of circulating P levels. The 50% reduction in P levels detected in AMH-treated dams could significantly lower the P break on LH secretion and further increases T production by theca cells.

The robust drop of plasmatic P and E2 detected in AMH-treated pregnant mice, most likely a result of compromised placental function, could explain the higher incidence of aborted fetuses observed in these animals.

Here, we also showed for the first time that the AMH-driven gestational hyperandrogenism triggers the masculinization of the brain in female offspring. In the developing male brain the appropriate exposure to androgens in utero is known to contribute to establishing sexually dimorphic brain circuitry controlling reproductive physiological processes. Interestingly, PAMH female animals exhibit a masculinization of both the neonatal T and LH surge, followed by a marked masculinization of the sexually dimorphic brain regions that regulate reproduction. Notably, the neonatal T and LH surges of PAMH female pups were corrected by prenatal GnRH antagonist administration, strongly indicating that the neonatal consequences of the gestational AMH treatments are programmed in utero and not neonatally.

Since GnRH neurons do not express androgen receptor or estrogen receptor alpha (ERα), the results described in the present disclosure suggest that steroid hormone receptor activation should occur in upstream neuronal afferents. Indeed, we provide evidence indicating that hyperandrogenism during critical periods of development leads to increased GABAergic appositions to GnRH neurons and to a persistent GnRH neuronal hyperactivity in adulthood.

Since GABAergic inputs are known to excite GnRH neurons, the results described in the present disclosure suggest that elevated excitatory innervation of GnRH neurons might be responsible for the increase in the GnRH/LH pulse frequency that we describe in PAMH adult females.

Such hyperactivation of GnRH neurons is most likely responsible for promoting the LH-driven ovarian androgen production over FSH release, which consequently leads to anovulation. Most lean women who are diagnosed with PCOS exhibit high-frequency LH secretion, which is suggestive of rapid GnRH pulsatility. This is the case for 95% of the metabolically healthy PCOS women but not for obese PCOS patients.

Management strategies aimed at treating PCOS have met only limited success and alternative and preventive therapies were therefore urgently needed, which alternative and preventive therapies are provided in the present disclosure.

Here, we showed that the prenatal co-treatment of AMH with the GnRH antagonist prevented the appearance of PCOS-like neuroendocrine traits in the offspring, suggesting a critical role for GnRH in the prenatal programming of the disease. Our Nano-HPLC-HRMS analyses demonstrated that the peripherally-injected Cetrorelix (1.4 kDa) can access the maternal as well as the fetal brain. Notably, in rodents' ovaries, the expression of functional gonadotropin receptors starts at the end of the first week of life and therefore it is not yet in place at embryonic stages during which we treated the animals with AMH+GnRH antagonist. These evidences, together with our data showing that recombinant AMH cannot cross the placental barrier, strongly suggest that the effect of the prenatal antagonist treatment on the prevention of PCOS-like traits acquisition in the offspring is most likely happening through the normalization of the maternal HPG axis.

Even more strikingly, we also showed that postnatal GnRH antagonist treatment of adult PAMH mice, at a concentration that only partially compete with endogenous GnRH for binding to membrane receptors on gonadotropes, restores their ovulation and normalizes androgen levels as well as LH secretion/pulsatility.

Given the fact that GnRH antagonists are frequently used in the clinic, with no adverse secondary effects, pharmacological antagonism aimed at tempering GnRH/LH secretion is an attractive therapeutic strategy to restore ovulation and fertility in PCOS individuals characterized by normal body mass composition and high LH levels.

The invention claimed is:

1. A method for treating polycystic ovary syndrome (PCOS) in a non-pregnant human female individual in need thereof, comprising a step of administering to the non-pregnant human female individual a gonadotropin-releasing hormone (GnRH) antagonist in an amount of from 0.01 mg to 0.1 mg, wherein:

the GnRH antagonist is selected from the group consisting of degarelix, ganirelix, cetrorelix and abarelix, the GnRH antagonist is administered by subcutaneous administration, and the amount is sufficient to restore LH pulsatility without blocking LH production in the non-pregnant human female individual.

2. The method according to claim 1, wherein the GnRH antagonist is comprised in a pharmaceutical composition adapted to its administration to a post-puberal female individual.

3. The method of claim 1, wherein the GnRH antagonist is administered as the sole active ingredient to treat PCOS in the non-pregnant human female individual.

4. The method of claim 1, wherein the non-pregnant human female individual is not obese.

5. The method of claim 1, wherein the amount is sufficient to restore ovulation, normal LH levels, and normal androgen levels.

* * * * *